US009637500B2

(12) United States Patent
Jensen et al.

(10) Patent No.: US 9,637,500 B2
(45) Date of Patent: May 2, 2017

(54) SOLID FORMS OF A MACROCYCLIC KINASE INHIBITOR

(71) Applicant: Pfizer Inc., New York, NY (US)

(72) Inventors: Andrew James Jensen, Ledyard, CT (US); Suman Luthra, Mystic, CT (US); Paul Francis Richardson, San Diego, CA (US)

(73) Assignee: Pfizer Inc., New York, NY (US)

( * ) Notice: Subject to any disclaimer, the term of this patent is extended or adjusted under 35 U.S.C. 154(b) by 20 days.

(21) Appl. No.: 14/898,582

(22) PCT Filed: Jun. 17, 2014

(86) PCT No.: PCT/IB2014/062296
§ 371 (c)(1),
(2) Date: Dec. 15, 2015

(87) PCT Pub. No.: WO2014/207606
PCT Pub. Date: Dec. 31, 2014

(65) Prior Publication Data
US 2016/0115178 A1    Apr. 28, 2016

Related U.S. Application Data

(60) Provisional application No. 61/840,703, filed on Jun. 28, 2013.

(51) Int. Cl.
*C07D 213/65* (2006.01)
*A61K 31/4439* (2006.01)
*C07D 498/18* (2006.01)

(52) U.S. Cl.
CPC .................................. *C07D 498/18* (2013.01)

(58) Field of Classification Search
CPC ............................. A61K 31/44; C07D 213/65
USPC ................................... 514/286, 326; 546/194
See application file for complete search history.

(56) References Cited

U.S. PATENT DOCUMENTS

| | | |
|---|---|---|
| 8,680,111 B2 | 3/2014 | Bailey et al. |
| 8,916,593 B2 | 12/2014 | Bunnage et al. |
| 9,133,215 B2 | 9/2015 | Bailey et al. |

FOREIGN PATENT DOCUMENTS

| | | |
|---|---|---|
| WO | 2011138751 | 11/2011 |
| WO | 20130132376 | 9/2013 |

OTHER PUBLICATIONS

Awad et al., "Acquired Resistance to Crizotinib from a Mutation in CD74-ROS1." N Engl J Med 2013; 368:2395-2401.
Birchmeier et al. "Expression and rearrangement of the ROSI gene in human glioblastoma cells." Proc Natl Acad Sci 1987; 84:9270-9274.
Birchmeier et al., "Characterization of an Activated Human ros Gene." Mol. Cell. Bio. 1986; 6(9):3109-3115.
Caren et al., "High incidence of DNA mutations and gene amplifications of the ALK gene in advanced sporadic neuroblastoma tumors." Biochem. J. 2008; 416:153-159.
Charest et al., "Fusion of FIG to the Receptor Tyrosine Kinase ROS in a Glioblastoma with an Interstitial del(6) (q21q21)." Genes Chromos. Can. 2003; 37(1): 58-71.
Choi et al., "EML4-ALK Mutations in Lung Cancer than Confer Resistance to ALK Inhibitors." N Engl J Med 2010; 363:1734-1739.
Gschwind et al., "The discovery of receptor tyrosine kinases: targets for cancer therapy." Nat. Rev. Cancer 2004; 4, 361-370.
Gu et al. "Survey of Tyrosine Kinase Signaling Reveals ROS Kinase Fusions in Human Cholangiocarcinoma." PLoS ONE 2011; 6(1): e15640.
Hanahan & Weinberg, "The hallmarks of cancer." Cell 2000; 100: 57-70.
Krause & Van Etten, "Tyrosine kinases as targets for cancer therapy." N. Engl. J. Med. 2005; 353: 172-187.
Milkiewicz & Ott, "Inhibitors of anaplastic lymphoma kinase: a patent review." Expert Opin. Ther. Patents 2010; 20:1653-1681.
Morris et al., "Fusion of a kinase gene, ALK, to a nucleolar protein gene, NPM, in non-Hodgkin's lymphoma." Science 1994; 263:1281-1284.
Nagarajan et al. "The human c-ros gene (ROS) is located at chromosome region 6ql66q22." Proc Natl Acad Sci 1986; 83:6568-6572.
Palmer et al., "Anaplastic lymphoma kinase: signaling in development and disease." Biochem. J. 2009; 420:345-361.
Pulford et al., "Anaplastic lymphoma kinase proteins in growth control and cancer." J. Cell Physiol., 2004; 199: 330-58.
Rikova et al., "Global Survey of Phosphotyrosine Signaling Identifies Oncogenic Kinases in Lung Cancer." Cell 2007; 131:1190-1203.
Rimkunas et al., "Analysis of Receptor Tyrosine Kinase ROS1-Positive Tumors in Non-Small Cell Lung Cancer: Identification of FIG-ROS1 Fusion." Clin Cancer Res 2012; 18:4449-4457.
Shaw et al. "Clinical activity of crizotinib in advanced non-small cell lung cancer (NSCLC) harboring ROS1 gene rearrangement." Presented at the Annual Meeting of the American Society of Clinical Oncology, Chicago, Jun. 1-5, 2012.
Soda et al., "Identification of the transforming EML4-ALK fusion gene in non-small cell lung cancer." Nature 2007; 448:561-566.
Soda et al., "A mouse model for EML4-ALK-positive lung cancer." Proc. Natl. Acad. Sci. U.S.A. 2008; 105:19893-19897.
Takeuchi et al., "RET, ROS1 and ALK fusions in lung cancer." Nature Medicine 2012; 18(3):378-381).
Wan et al., "Anaplastic lymphoma kinase activity is essential for the proliferation and survival of anaplastic large cell lymphoma cells." Blood, 2006; 107:1617-1623.
International Preliminary Report on Patentability dated Dec. 29, 2015 for International Publication No. WO 2014/207606.
International Search Report completed on Aug. 25, 2014 for International Publication No. WO 2014/207606.

*Primary Examiner* — Yong Chu
*Assistant Examiner* — Sonya Wright
(74) *Attorney, Agent, or Firm* — Leslie A. Robinson

(57) ABSTRACT

This invention relates to crystalline solvates of (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetradecine-3-carbonitrile, useful in the treatment of abnormal cell growth, such as cancer, in mammals. This invention also relates to pharmaceutical compositions comprising such crystalline solvates, and to methods of using such solvates and compositions in the treatment of abnormal cell growth in mammals, especially humans.

11 Claims, 16 Drawing Sheets

SOLID FORMS OF A MACROCYCLIC KINASE INHIBITOR

CROSS-REFERENCE TO RELATED APPLICATIONS

This application is the national stage filing under 35 U.S.C. 371 of Patent Cooperation Treaty Patent Application No. PCT/IB2014/062296, filed Jun. 17, 2014, which claims the benefit of U.S. Provisional Application No. 61/840,703 filed on Jun. 28, 2013, the contents of each of which are hereby incorporated by reference in their entirety.

FIELD OF THE INVENTION

This invention relates to crystalline forms of the macrocyclic kinase inhibitor, (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetradecine-3-carbonitrile, including crystalline solvates thereof, that may be useful in the treatment of abnormal cell growth, such as cancer, in mammals. The invention also relates to compositions including such crystalline forms, and to methods of using such compositions in the treatment of abnormal cell growth in mammals, especially humans.

BACKGROUND OF THE INVENTION

The compound (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetradecine-3-carbonitrile, represented by the formula (I):

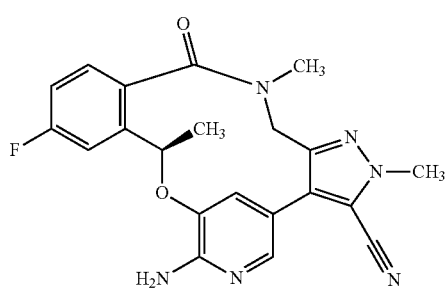

(I)

is a potent, macrocyclic inhibitor of both wild type and resistance mutant forms of anaplastic lymphoma kinase (ALK) and c-ros oncogene 1 (ROS1) receptor tyrosine kinase. Preparation of the free base compound of formula (I) as an amorphous solid is disclosed in International Patent Publication No. WO 2013/132376 and in United States Patent Publication No. 2013/0252961, the contents of which are incorporated herein by reference in their entirety.

Human cancers comprise a diverse array of diseases that collectively are one of the leading causes of death in developed countries throughout the world (American Cancer Society, Cancer Facts and FIGS. 2005. Atlanta: American Cancer Society; 2005). The progression of cancers is caused by a complex series of multiple genetic and molecular events including gene mutations, chromosomal translocations, and karyotypic abnormalities (Hanahan & Weinberg, The hallmarks of cancer. Cell 2000; 100: 57-70). Although the underlying genetic causes of cancer are both diverse and complex, each cancer type has been observed to exhibit common traits and acquired capabilities that facilitate its progression. These acquired capabilities include dysregulated cell growth, sustained ability to recruit blood vessels (i.e., angiogenesis), and ability of tumor cells to spread locally as well as metastasize to secondary organ sites (Hanahan & Weinberg 2000). Therefore, the ability to identify novel therapeutic agents that inhibit molecular targets that are altered during cancer progression or target multiple processes that are common to cancer progression in a variety of tumors presents a significant unmet need.

Receptor tyrosine kinases (RTKs) play fundamental roles in cellular processes, including cell proliferation, migration, metabolism, differentiation, and survival. RTK activity is tightly controlled in normal cells. The constitutively enhanced RTK activities from point mutation, amplification, and rearrangement of the corresponding genes have been implicated in the development and progression of many types of cancer. (Gschwind et al., The discovery of receptor tyrosine kinases: targets for cancer therapy. Nat. Rev. Cancer 2004; 4, 361-370; Krause & Van Etten, Tyrosine kinases as targets for cancer therapy. N. Engl. J. Med. 2005; 353: 172-187.)

Anaplastic lymphoma kinase (ALK) is a receptor tyrosine kinase, grouped together with leukocyte tyrosine kinase (LTK) to a subfamily within the insulin receptor (IR) superfamily. ALK was first discovered as a fusion protein with nucleophosmin (NPM) in anaplastic large cell lymphoma (ALCL) cell lines in 1994. (Morris et al., Fusion of a kinase gene, ALK, to a nucleolar protein gene, NPM, in non-Hodgkin's lymphoma. Science 1994; 263:1281-1284.) NPM-ALK, which results from a chromosomal translocation, is implicated in the pathogenesis of human anaplastic large cell lymphoma (ALCL) (Pulford et al., Anaplastic lymphoma kinase proteins in growth control and cancer. J. Cell Physiol., 2004; 199: 330-58). The roles of aberrant expression of constitutively active ALK chimeric proteins in the pathogenesis of ALCL have been defined (Wan et. al., Anaplastic lymphoma kinase activity is essential for the proliferation and survival of anaplastic large cell lymphoma cells. Blood, 2006; 107:1617-1623). Other chromosomal rearrangements resulting in ALK fusions have been subsequently detected in ALCL (50-60%), inflammatory myofibroblastic tumors (27%), and non-small-cell lung cancer (NSCLC) (2-7%). (Palmer et al., Anaplastic lymphoma kinase: signaling in development and disease. Biochem. J. 2009; 420:345-361.)

The EML4-ALK fusion gene, comprising portions of the echinoderm microtubule associated protein-like 4 (EML4) gene and the ALK gene, was first discovered in NSCLC archived clinical specimens and cell lines. (Soda et al., Identification of the transforming EML4-ALK fusion gene in non-small cell lung cancer. Nature 2007; 448:561-566; Rikova et al., Cell 2007; 131:1190-1203.) EML4-ALK fusion variants were demonstrated to transform NIH-3T3 fibroblasts and cause lung adenocarcinoma when expressed in transgenic mice, confirming the potent oncogenic activity of the EML4-ALK fusion kinase. (Soda et al., A mouse model for EML4-ALK-positive lung cancer. Proc. Natl. Acad. Sci. U.S.A. 2008; 105:19893-19897.) Oncogenic mutations of ALK in both familial and sporadic cases of neuroblastoma have also been reported. (Caren et al., High incidence of DNA mutations and gene amplifications of the ALK gene in advanced sporadic neuroblastoma tumors. Biochem. J. 2008; 416:153-159.)

ROS1 is a proto-oncogene receptor tyrosine kinase that belongs to the insulin receptor subfamily, and is involved in cell proliferation and differentiation processes. (Nagarajan et al. Proc Natl Acad Sci 1986; 83:6568-6572). ROS is expressed, in humans, in epithelial cells of a variety of different tissues. Defects in ROS expression and/or activation have been found in glioblastoma, as well as tumors of the central nervous system (Charest et al., Genes Chromos. Can. 2003; 37(1): 58-71). Genetic alterations involving ROS that result in aberrant fusion proteins of ROS kinase have been described, including the FIG-ROS deletion translocation in glioblastoma (Charest et al. (2003); Birchmeier et al. Proc Natl Acad Sci 1987; 84:9270-9274; and NSCLC (Rimkunas et al., Analysis of Receptor Tyrosine Kinase ROS1-Positive Tumors in Non-Small Cell Lung Cancer: Identification of FIG-ROS1 Fusion, Clin Cancer Res 2012; 18:4449-4457), the SLC34A2-ROS translocation in NSCLC (Rikova et al. Cell 2007; 131:1190-1203), the CD74-ROS translocation in NSCLC (Rikova et al. (2007)) and cholangiocarcinoma (Gu et al. PLoS ONE 2011; 6(1): e15640), and a truncated, active form of ROS known to drive tumor growth in mice (Birchmeier et al. Mol. Cell. Bio. 1986; 6(9):3109-3115). Additional fusions, including TPM3-ROS1, SDC4-ROS1, EZR-ROS1 and LRIG3-ROS1, have been reported in lung cancer patient tumor samples (Takeuchi et al., RET, ROS1 and ALK fusions in lung cancer, Nature Medicine 2012; 18(3):378-381).

The dual ALK/c-MET inhibitor crizotinib was approved in 2011 for the treatment of patients with locally advanced or metastatic NSCLC that is ALK-positive as detected by an FDA-approved test. Crizotinib has also shown efficacy in treatment of NSCLC with ROS1 translocations. (Shaw et al. Clinical activity of crizotinib in advanced non-small cell lung cancer (NSCLC) harboring ROS1 gene rearrangement. Presented at the Annual Meeting of the American Society of Clinical Oncology, Chicago, Jun. 1-5, 2012.) As observed clinically for other tyrosine kinase inhibitors, mutations in ALK and ROS1 that confer resistance to ALK inhibitors have been described (Choi et al., EML4-ALK Mutations in Lung Cancer than Confer Resistance to ALK Inhibitors, N Eng J Med 2010; 363:1734-1739; Awed et al., Acquired Resistance to Crizotinib from a Mutation in CD74-ROS1, N Engl J Med 2013; 368:2395-2401).

Thus, ALK and ROS1 are attractive molecular targets for cancer therapeutic intervention. There remains a need to identify compounds having novel activity profiles against wild-type and mutant forms of ALK and ROS1.

The present invention provides crystalline forms of the free base of (10R)-7-amino-12-fluoro-2,10,16-trimethyl-15-oxo-10,15,16,17-tetrahydro-2H-8,4-(metheno)pyrazolo[4,3-h][2,5,11]-benzoxadiazacyclotetradecine-3-carbonitrile having improved properties, such as improved crystallinity, dissolution properties, decreased hygroscopicity, improved mechanical properties, improved purity, and/or improved stability, while maintaining chemical and enantiomeric stability.

SUMMARY OF THE INVENTION

In one aspect, the invention provides a crystalline form of (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetradecine-3-carbonitrile. The crystalline forms of (10R)-7-amino-12-fluoro-2,10,16-trimethyl-15-oxo-10,15,16,17-tetrahydro-2H-8,4-(metheno)pyrazolo-[4,3-h][2,5,11]benzoxadiazacyclotetradecine-3-carbonitrile described herein are crystalline forms of the free base.

In specific aspects, the crystalline form of (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetradecine-3-carbonitrile is a crystalline solvate. In a preferred embodiment, the crystalline solvate is a crystalline acetic acid solvate. In some such embodiments, the crystalline acetic acid solvate comprises about one molecule of acetic acid per molecule of (10R)-7-amino-12-fluoro-2, 10,16-trimethyl-15-oxo-10,15,16,17-tetrahydro-2H-8,4-(metheno)pyrazolo[4,3-h][2,5,11]benzoxadiazacyclotetradecine-3-carbonitrile. In a specific embodiment, the crystalline solvate is the acetic acid solvate Form 3 disclosed herein. In another preferred embodiment, the crystalline solvate is a hydrate. In specific embodiments, the crystalline hydrate is the hydrate Form 1 or the hydrate Form 2 disclosed herein.

In another aspect, the invention provides a crystalline solvate of (10R)-7-amino-12-fluoro-2,10,16-trimethyl-15-oxo-10,15,16,17-tetrahydro-2H-8,4-(metheno)pyrazolo[4, 3-h][2,5,11]benzoxadiazacyclotetradecine-3-carbonitrile. In particular embodiments, the crystalline solvate is a crystalline acetic acid solvate, including the solvate Form 3 herein. In other embodiments, the crystalline solvate is a crystalline hydrate, including the hydrates Form 1 and Form 2 herein.

In particular embodiments of each of the aspects of the invention, the crystalline form of (10R)-7-amino-12-fluoro-2,10,16-trimethyl-15-oxo-10,15,16,17-tetrahydro-2H-8,4-(metheno)-pyrazolo[4,3-h][2,5,11]benzoxadiazacyclotetradecine-3-carbonitrile is characterized by one or more of the following methods: (1) powder X-ray diffraction (PXRD) (2θ); (2) Raman spectroscopy (cm$^{-1}$); (3)$^{13}$C solid state NMR spectroscopy (ppm); or (4)$^{19}$F solid state NMR spectroscopy (ppm).

In a first preferred aspect, the invention provides a crystalline hydrate of (10R)-7-amino-12-fluoro-2,10,16-trimethyl-15-oxo-10,15,16,17-tetrahydro-2H-8,4-(metheno) pyrazolo[4,3-h][2,5,11]benzoxadiazacyclotetradecine-3-carbonitrile (Form 1), which is characterized by having:

(1) a powder X-ray diffraction (PXRD) pattern (2θ) comprising: (a) one, two, three, four, five, or more than five peaks selected from the group consisting of the peaks in Table 1 in °2θ±0.2 °2θ; (b) one, two or three peaks selected from the group consisting of the peaks in Table 2 in °2θ±0.2 °2θ; or (c) peaks at 2θ values essentially the same as shown in FIG. 1; or (2) a Raman spectrum comprising: (a) one, two, three, four, five, or more than five wavenumber (cm$^{-1}$) values selected from the group consisting of the values in Table 3 in cm$^{-1}$±2 cm$^{-1}$; (b) one, two, three, four, five, or more than five wavenumber (cm$^{-1}$) values selected from the group consisting of the values in Table 4 in cm$^{-1}$±2 cm$^{-1}$; or (c) wavenumber (cm$^{-1}$) values essentially the same as shown in FIG. 4; or (3) a $^{13}$C solid state NMR spectrum (ppm) comprising: (a) one, two, three, four, five, or more than five resonance (ppm) values selected from the group consisting of the values in Table 5 in ppm±0.2 ppm; (b) one, two or three resonance (ppm) values selected from the group consisting of the values in Table 6 in ppm±0.2 ppm; or (c) resonance (ppm) values essentially the same as shown in FIG. 7; or (4) a $^{19}$F solid state NMR spectrum (ppm) comprising: (a) one, two, three, four or five resonance (ppm) values selected from the group consisting of the values in Table 7 in ppm±0.2 ppm; (b) one or two resonance (ppm) values in Table 8 in ppm±0.2 ppm; or (c) resonance (ppm) values essentially the same as shown in FIG. 10;

or a combination of any two, three or four of the foregoing embodiments (1)(a)-(c), (2)(a)-(c), (3)(a)-(c), or (4)(a)-(c), provided they are not inconsistent with each other.

In a second preferred aspect, the invention provides a crystalline hydrate of (10R)-7-amino-12-fluoro-2,10,16- trimethyl-15-oxo-10,15,16,17-tetrahydro-2H-8,4-(metheno) pyrazolo[4,3-h][2,5,11]benzoxadiazacyclotetradecine-3-carbonitrile (Form 2), which is characterized by having:

(1) a powder X-ray diffraction (PXRD) pattern (2θ) comprising: (a) one, two, three, four, five, or more than five peaks selected from the group consisting of the peaks in Table 9 in °2θ±0.2 °2θ; (b) one, two, three, four or five peaks selected from the group consisting of the peaks in Table 10 in °2θ±0.2 °2θ; or (c) peaks at 2θ values essentially the same as shown in FIG. 2; or (2) a Raman spectrum comprising: (a) one, two, three, four, five, or more than five wavenumber (cm$^{-1}$) values selected from the group consisting of the values in Table 11 in cm$^{-1}$±2 cm$^{-1}$; (b) one, two, three, four, five, or more than five wavenumber (cm$^{-1}$) values selected from the group consisting of the values in Table 12 in cm$^{-1}$±2 cm$^{-1}$; or (c) wavenumber (cm$^{-1}$) values essentially the same as shown in FIG. 5; or (3) a $^{13}$C solid state NMR spectrum (ppm) comprising: (a) one, two, three, four, five, or more than five resonance (ppm) values selected from the group consisting of the values in Table 13 in ppm±0.2 ppm; (b) one, two or three resonance (ppm) values selected from the group consisting of the values in Table 14 in ppm±0.2 ppm; or (c) resonance (ppm) values essentially the same as shown in FIG. 8; or (4) a $^{19}$F solid state NMR spectrum (ppm) comprising: (a) one, two or three resonance (ppm) values selected from the group consisting of the values in Table 15 in ppm±0.2 ppm; (b) the resonance (ppm) value in Table 16 in ppm±0.2 ppm; or (c) resonance (ppm) values essentially the same as shown in FIG. 11;

or a combination of any two, three or four of the foregoing embodiments (1)(a)-(c), (2)(a)-(c), (3)(a)-(c), or (4)(a)-(c), provided they are not inconsistent with each other.

In a third preferred aspect, the invention provides a crystalline acetic acid solvate of (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetradecine-3-carbonitrile (Form 3), which is characterized by having:

(1) a powder X-ray diffraction (PXRD) pattern (2θ) comprising: (a) one, two, three, four, five, or more than five peaks selected from the group consisting of the peaks in Table 17 in °2θ±0.2 °2θ; (b) one, two, three, four, or five peaks selected from the group consisting of the peaks in Table 18 in °2θ±0.2 °2θ; or (c) peaks at 2θ values essentially the same as shown in FIG. 3; or (2) a Raman spectrum comprising: (a) one, two, three, four, five, or more than five wavenumber (cm$^{-1}$) values selected from the group consisting of the values in Table 19 in cm$^{-1}$±2 cm$^{-1}$; (b) one, two, three, four, five, or more than five wavenumber (cm$^{-1}$) values selected from the group consisting of the values in Table 20 in cm$^{-1}$±2 cm$^{-1}$; (c) one, two, three, or four wavenumber (cm$^{-1}$) values selected from the group consisting of the values in Table 21 in cm$^{-1}$±2 cm$^{-1}$; or (d) wavenumber (cm$^{-1}$) values essentially the same as shown in FIG. 6; or (3) a $^{13}$C solid state NMR spectrum (ppm) comprising: (a) one, two, three, four, five, or more than five resonance (ppm) values selected from the group consisting of the values in Table 22 in ppm±0.2 ppm; (b) one, two, or three resonance (ppm) values selected from the group consisting of the values in Table 23 in ppm±0.2 ppm; or (c) resonance (ppm) values essentially the same as shown in FIG. 9; or (4) a $^{19}$F solid state NMR spectrum (ppm) comprising: (a) the resonance (ppm) value in Table 24 in ppm±0.2 ppm; or (b) resonance (ppm) values essentially the same as shown in FIG. 12;

or a combination of any two, three or four of the foregoing embodiments (1)(a)-(c), (2)(a)-(d), (3)(a)-(c), or (4)(a)-(b), provided they are not inconsistent with each other.

In another aspect, the invention further provides a pharmaceutical composition comprising a crystalline solvate of (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetradecine-3-carbonitrile, according to any of the aspects or embodiments described herein, and a pharmaceutically acceptable excipient. In a particular embodiment, the invention provides a pharmaceutical composition comprising a crystalline acetic acid solvate of (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetradecine-3-carbonitrile, and a pharmaceutically acceptable excipient. In specific embodiments, the crystalline acetic acid solvate is the solvate Form 3 described herein. In other embodiments, the invention provides a pharmaceutical composition comprising a crystalline hydrate of (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetradecine-3-carbonitrile, and a pharmaceutically acceptable excipient. In specific embodiments, the crystalline hydrate is the hydrate Form 1 or Form 2 described herein.

In another aspect, the invention provides a method of treating abnormal cell growth in a mammal, including a human, comprising administering to the mammal a therapeutically effective amount of crystalline solvate of (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetradecine-3-carbonitrile. In particular embodiments, the solvate is the acetic acid solvate Form 3 or the hydrate Form 1 or Form 2 described herein.

In another aspect, the invention provides a method of treating abnormal cell growth in a mammal, including a human, comprising administering to the mammal a therapeutically effective amount of a pharmaceutical composition of the present invention, such composition comprising a crystalline solvate of (10R)-7-amino-12-fluoro-2,10,16-trimethyl-15-oxo-10,15,16,17-tetrahydro-2H-8,4-(metheno) pyrazolo[4,3-h][2,5,11]benzoxadiazacyclotetradecine-3-carbonitrile, according to any of the aspects or embodiments described herein.

In specific embodiments, the method of treating abnormal cell growth in a mammal, including a human, comprises administering a crystalline acetic acid solvate of (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetradecine-3-carbonitrile, in particular the solvate Form 3 described herein, or a pharmaceutical composition comprising such a solvate. In other embodiments, the method comprises administering a crystalline hydrate of (10R)-7-amino-12-fluoro-2,10,16-trimethyl-15-oxo-10,15, 16,17-tetrahydro-2H-8,4-(metheno)pyrazolo[4,3-h][2,5,11] benzoxadiazacyclotetradecine-3-carbonitrile, in particular the hydrate Form 1 or Form 2 described herein, or a pharmaceutical composition comprising such a hydrate.

In frequent embodiments, the abnormal cell growth is cancer. In one embodiment, the abnormal cell growth is mediated by ALK or ROS1. In another embodiment, the abnormal cell growth is mediated by ALK. In another embodiment, the abnormal cell growth is mediated by ROS1. In further embodiments, the abnormal cell growth is mediated by at least one genetically altered tyrosine kinase, such as a genetically altered ALK or a genetically altered ROS1 kinase. In frequent embodiments of each of the foregoing, the abnormal cell growth is a cancer.

In some such embodiments, the cancer is selected from lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, or pituitary adenoma, and combinations thereof.

In other such embodiments, the cancer is selected from the group consisting of non-small cell lung cancer (NSCLC), squamous cell carcinoma, hormone-refractory prostate cancer, papillary renal cell carcinoma, colorectal adenocarcinoma, neuroblastoma, anaplastic large cell lymphoma (ALCL) and gastric cancer. In specific embodiments, the cancer is non-small cell lung cancer (NSCLC). In particular embodiments, the cancer is NSCLC mediated by ALK or ROS1, in particular by a genetically altered ALK or ROS1.

DETAILED DESCRIPTION OF THE INVENTION

Figure 1:
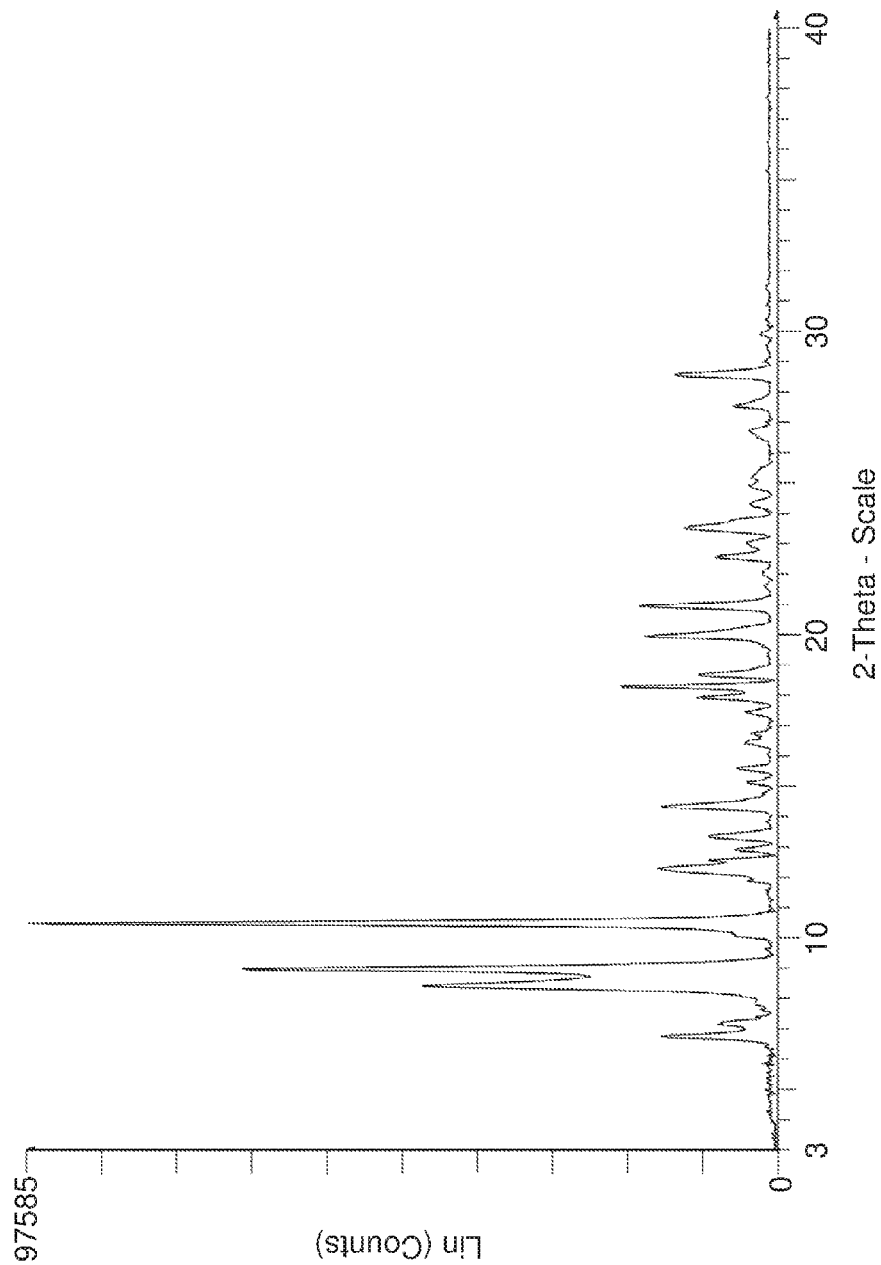
FIG. 1: PXRD pattern of crystalline hydrate of (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetradecine-3-carbonitrile (Form 1).

The present invention may be understood more readily by reference to the following detailed description of the embodiments of the invention and the Examples included herein. It is to be understood that the terminology used herein is for the purpose of describing specific embodiments only and is not intended to be limiting. It is further to be understood that unless specifically defined herein, the terminology used herein is to be given its traditional meaning as known in the relevant art.

As used herein, the singular form "a", "an", and "the" include plural references unless indicated otherwise. For example, "a" substituent includes one or more substituents.

As used herein, unless otherwise indicated, the term "abnormal cell growth" refers to cell growth that is independent of normal regulatory mechanisms (e.g., loss of contact inhibition).

As used herein, unless otherwise indicated, the term "treat" or "treating" means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above.

The term "about" means having a value falling within an accepted standard of error of the mean, when considered by one of ordinary skill in the art.

As used herein, the term "essentially the same" means that variability typical for a particular method is taken into account. For example, with reference to X-ray diffraction peak positions, the term "essentially the same" means that typical variability in peak position and intensity are taken into account. One skilled in the art will appreciate that the peak positions (2θ) will show some variability, typically as much as ±0.2°. Further, one skilled in the art will appreciate that relative peak intensities will show inter-apparatus variability as well as variability due to degree of crystallinity, preferred orientation, prepared sample surface, and other factors known to those skilled in the art, and should be taken as qualitative measures only. Similarly, Raman spectrum wavenumber ($cm^{-1}$) values show variability, typically as much as ±2 $cm^{-1}$, while $^{13}C$ and $^{19}F$ solid state NMR spectrum (ppm) show variability, typically as much as ±0.2 ppm.

The term "crystalline" as used herein, means having a regularly repeating arrangement of molecules or external face planes. Crystalline forms may differ with respect to thermodynamic stability, physical parameters, x-ray structure and preparation processes.

The term "solvate," as used herein, means having on a surface, in a lattice or on a surface and in a lattice, a solvent such as water, acetic acid, methanol, etc., or mixtures thereof.

The term "amorphous" refers to a disordered solid state.

The invention described herein suitably may be practiced in the absence of any element(s) not specifically disclosed herein. Thus, for example, in each instance herein any of the terms "comprising", "consisting essentially of", and "consisting of" may be replaced with either of the other two terms.

In one aspect, the invention provides a crystalline form of (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetradecine-3-carbonitrile. In some embodiments, the crystalline form is a crystalline solvate, in particular a crystalline acetic acid solvate or a crystalline hydrate of (10R)-7-amino-12-fluoro-2,10,16-trimethyl-15-oxo-10,15,16,17-tetrahydro-2H-8,4-(metheno)pyrazolo-[4,3-h][2,5,11]benzoxadiazacyclotetradecine-3-carbonitrile.

In another aspect, the invention provides a crystalline solvate of (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetradecine-3-carbonitrile. In some embodiments, the crystalline solvate is a crystalline acetic acid solvate. In some such embodiments, the crystalline acetic acid solvate comprises about one molecule of acetic acid per molecule of (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetradecine-3-carbonitrile. In a specific embodiment, the crystalline acetic acid solvate is the crystalline solvate Form 3 disclosed herein. In other embodiments, the crystalline solvate is a crystalline hydrate. In particular embodiments, the crystalline hydrate comprises about 0.5 molecules of water per molecule (i.e., hemihydrate), about 1 molecule of water (i.e., monohydrate), or about 0.75 molecule of water per molecule of (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetradecine-3-carbonitrile. In some such embodiments, the crystalline hydrate further comprises methanol or another solvent. In specific embodiments, the crystalline hydrate is the hydrate Form 1 or the hydrate Form 2 disclosed herein.

In some embodiments of each of the aspects of the invention, the crystalline form of (10R)-7-amino-12-fluoro-2,10,16-trimethyl-15-oxo-10,15,16,17-tetrahydro-2H-8,4-(metheno)-pyrazolo[4,3-h][2,5,11]benzoxadiazacyclotetradecine-3-carbonitrile is characterized by its powder X-ray diffraction (PXRD) pattern. In other embodiments of each of the aspects of the invention, the crystalline form of (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetradecine-3-carbonitrile is characterized by its Raman spectrum. In other embodiments of each of the aspects of the invention, the crystalline form of (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetradecine-3-carbonitrile is characterized by its $^{13}C$ solid state NMR spectrum. In still other embodiments of each of the aspects of the invention, the crystalline form of (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetradecine-3-carbonitrile is characterized by its $^{19}F$ solid state NMR spectrum.

In further embodiments, the crystalline form is characterized by a combination of two, three or four of these methods. Exemplary combinations including two or more of the following are provided herein: powder X-ray diffraction (PXRD) pattern (2θ); Raman spectrum wavenumber values ($cm^{-1}$); $^{13}C$ solid state NMR spectrum (ppm); or $^{19}F$ solid state NMR spectrum (ppm). It will be understood that other combinations of two, three or four techniques may be used to uniquely characterize the crystalline forms of the invention, including the crystalline hydrate Form 1, hydrate Form 2 and acetic acid solvate Form 3 disclosed herein.

It will be understood that references to crystalline form described herein encompass a crystalline solvate of (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetradecine-3-carbonitrile, and in particular a crystalline acetic acid solvate or a crystalline hydrate thereof, including the crystalline acetic acid solvate Form 3 and the crystalline hydrates Form 1 and Form 2.

Crystalline Hydrate Form 1

In a first preferred aspect, the invention provides a crystalline hydrate (Form 1) of (10R)-7-amino-12-fluoro-2,10,16-trimethyl-15-oxo-10,15,16,17-tetrahydro-2H-8,4-(metheno)pyrazolo-[4,3-h][2,5,11]benzoxadiazacyclotetradecine-3-carbonitrile.

In one embodiment, the hydrate Form 1 has a PXRD pattern comprising peaks at 2θ values of: 8.9 °2θ±0.2 °2θ. In another embodiment, the hydrate Form 1 has a PXRD pattern comprising peaks at 2θ values of: 8.4 °2θ±0.2 °2θ. In another embodiment, the hydrate Form 1 has a PXRD pattern comprising peaks at 2θ values of: 10.4 °2θ±0.2 °2θ. In another embodiment, the hydrate Form 1 has a PXRD pattern comprising peaks at 2θ values of: 8.9 and 10.4

°2θ±0.2 °2θ. In another embodiment, the hydrate Form 1 has a PXRD pattern comprising peaks at 2θ values of: 8.4 and 8.9 °2θ±0.2 °2θ. In yet another embodiment, the hydrate Form 1 has a PXRD pattern comprising peaks at 2θ values of: 8.4, 8.9 and 10.4 °2θ±0.2 °2θ. In some such embodiments, the PXRD pattern further comprises one or more additional peaks at 2θ values selected from the group consisting of the peaks listed in Table 1.

In specific embodiments, the hydrate Form 1 has a PXRD pattern comprising: (a) one, two, three, four, five, or more than five peaks selected from the group consisting of the peaks in Table 1 in °2θ±0.2 °2θ; (b) one, two or three peaks selected from the group consisting of the peaks in Table 2 in °2θ±0.2 °2θ; or (c) peaks at 2θ values essentially the same as shown in FIG. 1.

In one embodiment, the hydrate Form 1 has a Raman spectrum comprising wavenumber (cm$^{-1}$) values of: 2228 cm$^{-1}$±2 cm$^{-1}$. In another embodiment, the hydrate Form 1 has a Raman spectrum comprising wavenumber (cm$^{-1}$) values of: 1554 cm$^{-1}$±2 cm$^{-1}$. In other embodiments, the hydrate Form 1 has a Raman spectrum comprising wavenumber (cm$^{-1}$) values of: 1554 and 2228 cm$^{-1}$±2 cm$^{-1}$. In another embodiment, the hydrate Form 1 has a Raman spectrum comprising wavenumber (cm$^{-1}$) values of: 805, 1554 and 2228 cm$^{-1}$±2 cm$^{-1}$. In another embodiment, the hydrate Form 1 has a Raman spectrum comprising wavenumber (cm$^{-1}$) values of: 1554, 2228 and 3063 cm$^{-1}$±2 cm$^{-1}$. In another embodiment, the hydrate Form 1 has a Raman spectrum comprising wavenumber (cm$^{-1}$) values of: 805, 1554, 2228 and 3063 cm$^{-1}$±2 cm$^{-1}$.

Figure 4:
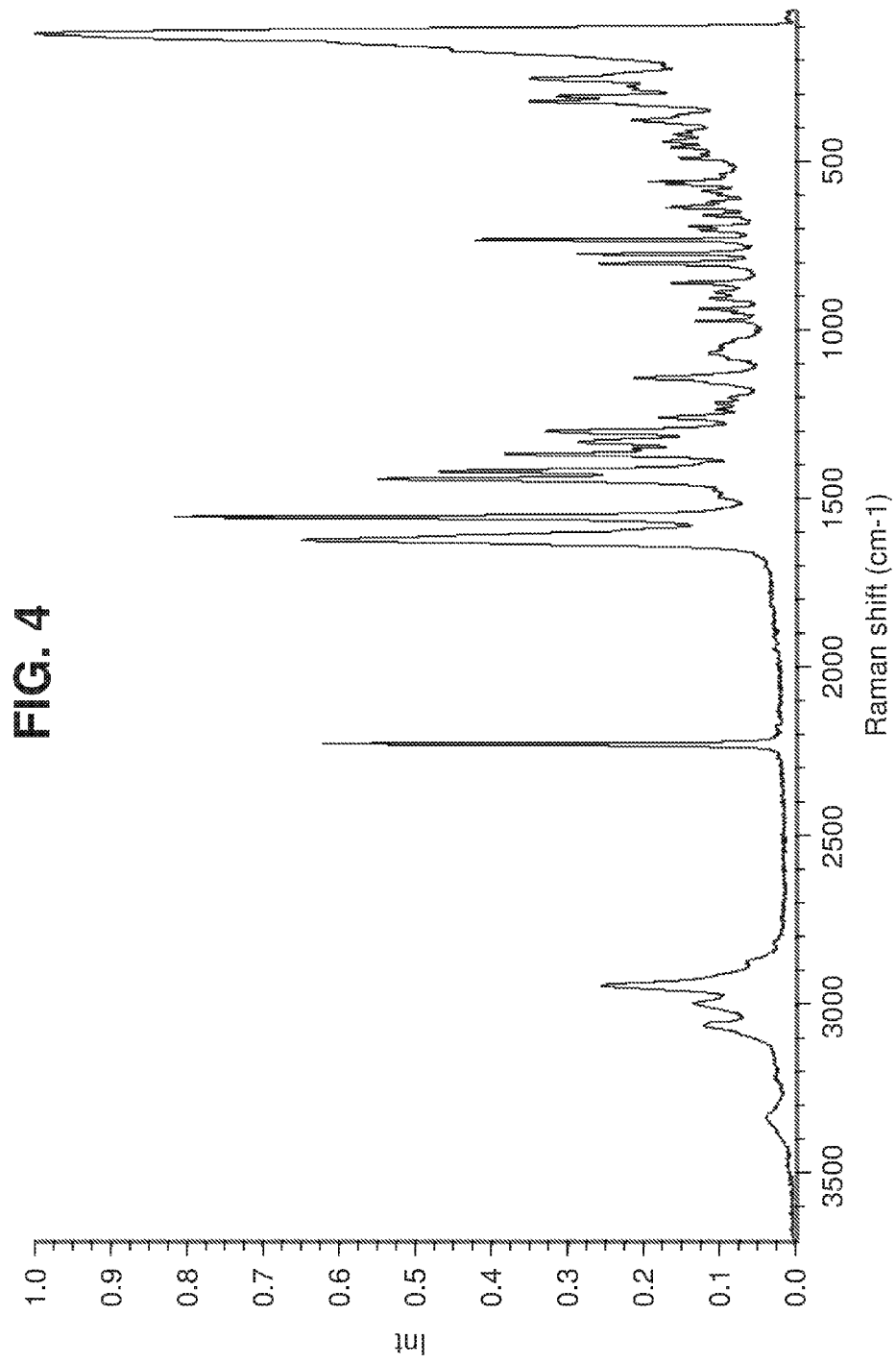
FIG. 4. FT-Raman pattern of crystalline hydrate of (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetradecine-3-carbonitrile (Form 1).

In specific embodiments, the hydrate Form 1 has a Raman spectrum comprising: (a) one, two, three, four, five, or more than five wavenumber (cm$^{-1}$) values selected from the group consisting of the values in Table 3 in cm$^{-1}$±2 cm$^{-1}$; (b) one, two, three, four, five, or more than five wavenumber (cm$^{-1}$) values selected from the group consisting of the values in Table 4 in cm$^{-1}$±2 cm$^{-1}$; or (c) wavenumber (cm$^{-1}$) values essentially the same as shown in FIG. 4.

In some embodiments, the hydrate Form 1 has a $^{13}$C solid state NMR spectrum comprising the resonance (ppm) values of: 113.6 ppm±0.2 ppm. In another embodiment, the hydrate Form 1 has a $^{13}$C solid state NMR spectrum comprising the resonance (ppm) values of: 133.6 ppm±0.2 ppm. In another embodiment, the hydrate Form 1 has a $^{13}$C solid state NMR spectrum comprising the resonance (ppm) values of: 47.3, 113.6 and 133.6 ppm±0.2 ppm.

Figure 7:
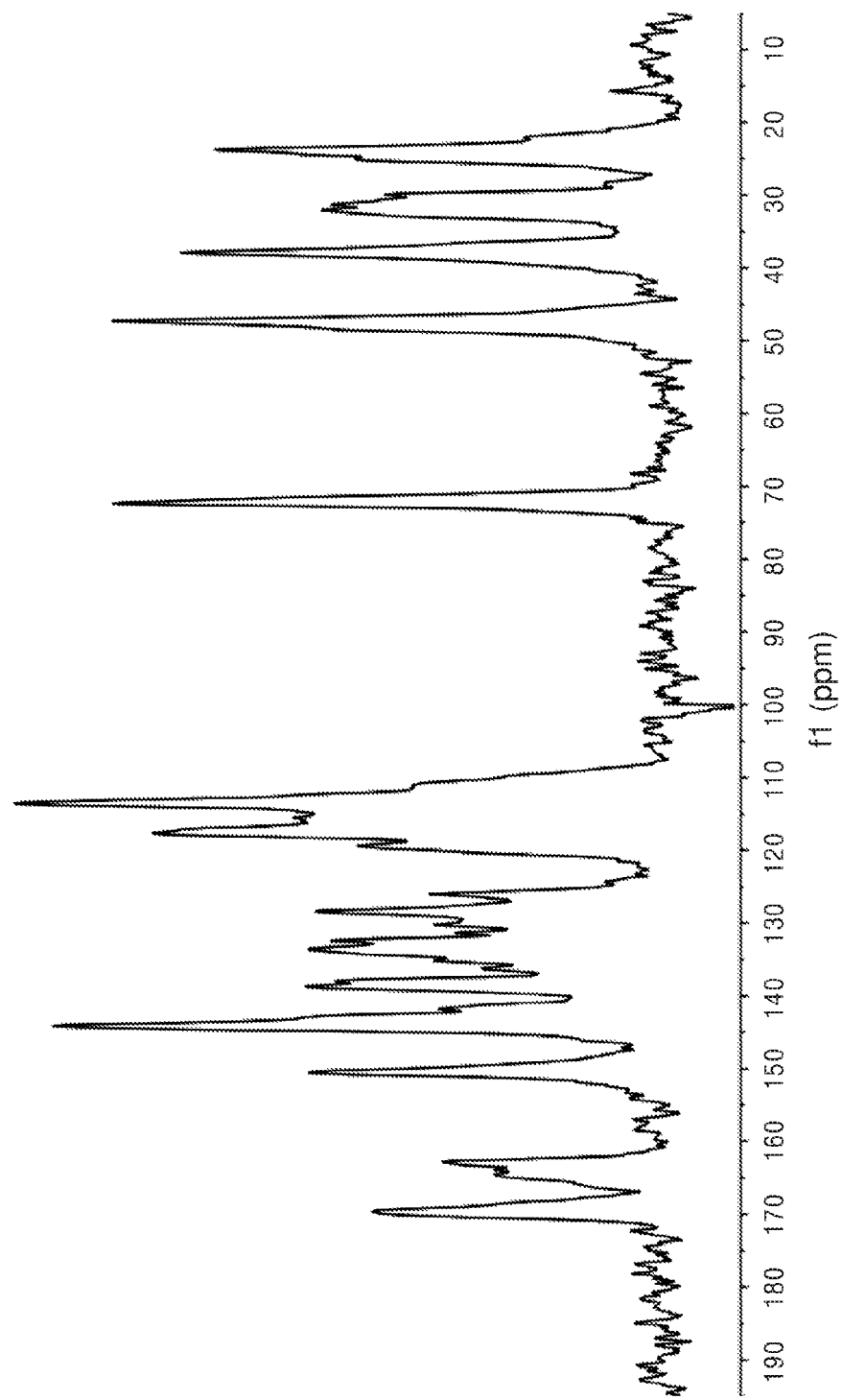
FIG. 7. Carbon CPMAS spectrum of crystalline hydrate of (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetradecine-3-carbonitrile (Form 1).

In specific embodiments, the hydrate Form 1 has a $^{13}$C solid state NMR spectrum (ppm) comprising: (a) one, two, three, four, five, or more than five resonance (ppm) values selected from the group consisting of the values in Table 5 in ppm±0.2 ppm; (b) one, two or three resonance (ppm) values selected from the group consisting of the values in Table 6 in ppm±0.2 ppm; or (c) resonance (ppm) values essentially the same as shown in FIG. 7.

Figure 10:
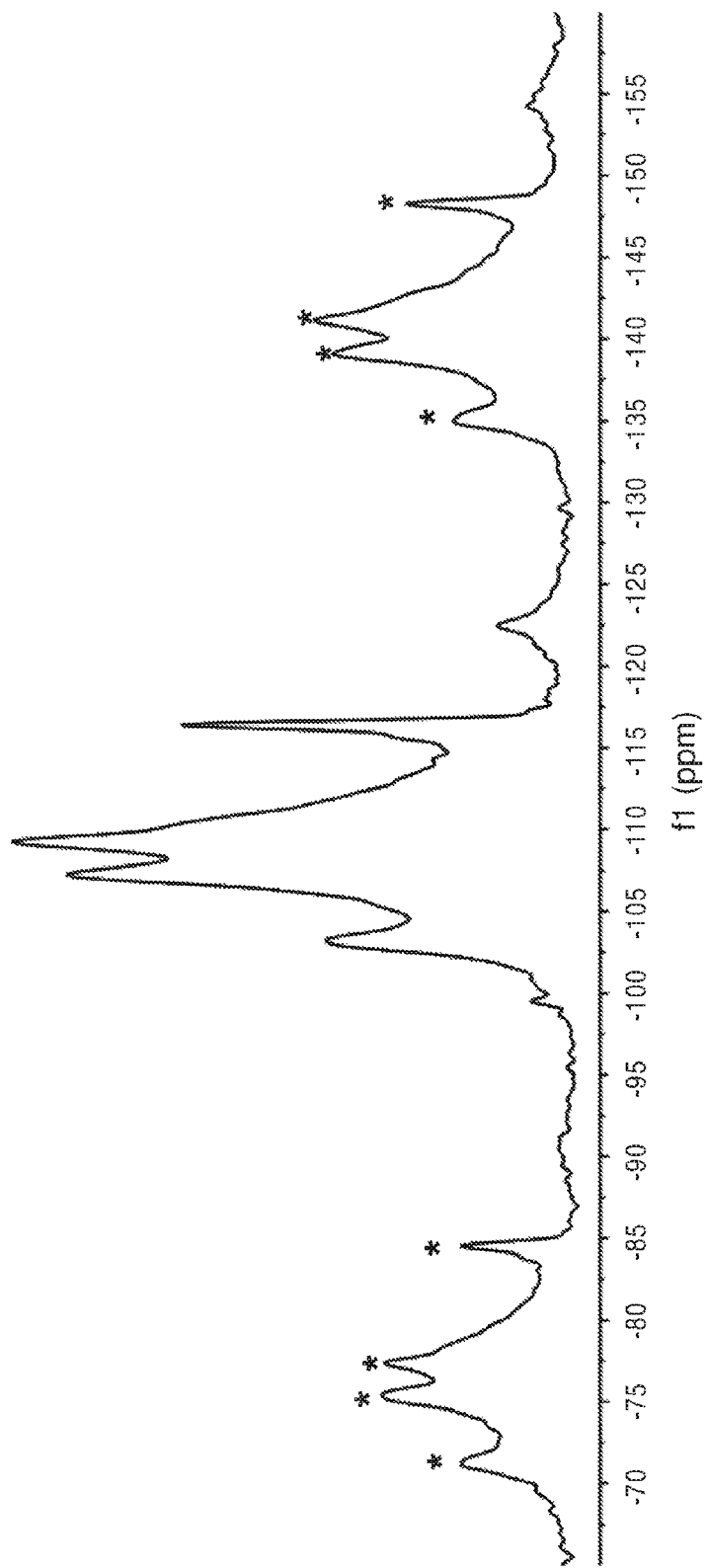
FIG. 10. Fluorine MAS spectrum of crystalline hydrate of (10R)-7-amino-12-fluoro-2,10,16-trimethyl-15-oxo-10,15, 16,17-tetrahydro-2H-8,4-(metheno)pyrazolo[4,3-h][2,5,11]benzoxadiazacyclotetradecine-3-carbonitrile (Form 1). The peaks marked by asterisks are spinning sidebands.

In other embodiments, the hydrate Form 1 has a $^{19}$F solid state NMR spectrum comprising a resonance (ppm) value of: −109.2 ppm±0.2 ppm. In another embodiment, the hydrate Form 1 has a $^{19}$F solid state NMR spectrum (ppm) comprising a resonance (ppm) value of: −116.4 ppm±0.2 ppm. In another embodiment, the hydrate Form 1 has a $^{19}$F solid state NMR spectrum comprising resonance (ppm) values of: −109.2 and −116.4 ppm±0.2 ppm. In another embodiment, the hydrate Form 1 has a $^{19}$F solid state NMR spectrum (ppm) comprising: (a) one, two, three, four or five resonance (ppm) values in Table 7 in ppm±0.2 ppm; (b) one or two resonance (ppm) values in Table 8 in ppm±0.2 ppm; or (c) resonance (ppm) values essentially the same as shown in FIG. 10.

In further embodiments, the hydrate Form 1 is characterized by a combination of two, three or four of the embodiments described above with respect to Form 1 that are not inconsistent with each other. Exemplary embodiments that may be used to uniquely characterize the hydrate Form 1 are provided below.

In one embodiment, the hydrate Form 1 has a powder X-ray diffraction pattern comprising a peak at a 2θ value of: 8.4, 8.9 and 10.4 °2θ±0.2 °2θ.

In one embodiment, the hydrate Form 1 has: (a) a powder X-ray diffraction pattern comprising a peak at a 2θ value of: 8.9 °2θ±0.2 °2θ; and (b) a Raman spectrum comprising wavenumber (cm$^{-1}$) values of: 1554 and 2228 cm$^{-1}$±2 cm$^{-1}$.

In another embodiment, the hydrate Form 1 has: (a) a powder X-ray diffraction pattern comprising a peak at a 2θ value of: 8.9 °2θ±0.2 °2θ; (b) a $^{13}$C solid state NMR spectrum comprising a resonance (ppm) value of: 113.6 ppm±0.2 ppm; and (c) a $^{19}$F solid state NMR spectrum comprising the resonance (ppm) value of: −109.2 ppm±0.2 ppm.

In another embodiment, the hydrate Form 1 has: (a) a Raman spectrum comprising wavenumber (cm$^{-1}$) values of: 1554 and 2228 cm$^{-1}$±2 cm$^{-1}$; (b) a $^{13}$C solid state NMR spectrum comprising a resonance (ppm) value of: 113.6 ppm±0.2 ppm; and (c) a $^{19}$F solid state NMR spectrum comprising the resonance (ppm) value of: −109.2 ppm±0.2 ppm.

In another embodiment, the hydrate Form 1 has: (a) a Raman spectrum comprising wavenumber (cm$^{-1}$) values of: 1554 and 2228 cm$^{-1}$±2 cm$^{-1}$; and (b) a $^{13}$C solid state NMR spectrum comprising a resonance (ppm) value of: 113.6 ppm±0.2 ppm.

In another embodiment, the hydrate Form 1 has: (a) a powder X-ray diffraction pattern comprising a peak at a 2θ value of: 8.9 °2θ±0.2 °2θ; (b) a Raman spectrum comprising wavenumber (cm$^{-1}$) values of: 1554 and 2228 cm$^{-1}$±2 cm$^{-1}$; and (c) a $^{13}$C solid state NMR spectrum comprising a resonance (ppm) value of: 113.6 ppm±0.2 ppm.

In another embodiment, the hydrate Form 1 has a Raman spectrum comprising wavenumber (cm$^{-1}$) values of: 805, 1554, 2228 and 3063 cm$^{-1}$+2 cm$^{-1}$.

In another embodiment, the hydrate Form 1 has a $^{19}$F solid state NMR spectrum comprising the resonance (ppm) value of: −116.4 and −109.2 ppm±0.2 ppm.

In another embodiment, the hydrate Form 1 has a $^{13}$C solid state NMR spectrum comprising resonance (ppm) values of: 47.3, 113.6 and 133.6 ppm±0.2 ppm.

Crystalline Hydrate Form 2

In a second preferred aspect, the invention provides a crystalline hydrate (Form 2) of (10R)-7-amino-12-fluoro-2,10,16-trimethyl-15-oxo-10,15,16,17-tetrahydro-2H-8,4-(metheno)-pyrazolo[4,3-h][2,5,11]benzoxadiazacyclotetradecine-3-carbonitrile.

In one such embodiment, the hydrate Form 2 has a PXRD pattern comprising peaks at 2θ values of: 7.6 °2θ±0.2 °2θ. In one such embodiment, the hydrate Form 2 has a PXRD pattern comprising peaks at 2θ values of: 10.2 °2θ±0.2 °2θ. In another embodiment, the hydrate Form 2 has a PXRD pattern comprising peaks at 2θ values of: 7.6 and 10.2 °2θ±0.2 °2θ. In another embodiment, the hydrate Form 2 has a PXRD pattern comprising peaks at 2θ values of: 7.6. 9.5 and 10.2 °2θ±0.2 °2θ. In another embodiment, the hydrate Form 2 has a PXRD pattern comprising peaks at 2θ values of: 5.6, 7.6, 9.5 and 10.2 °2θ±0.2 °2θ. In yet another embodiment, the hydrate Form 2 has a PXRD pattern comprising peaks at 2θ values of: 5.6, 7.6, 9.5, 10.2 and 13.6 °2θ±0.2 °2θ.

Figure 2:
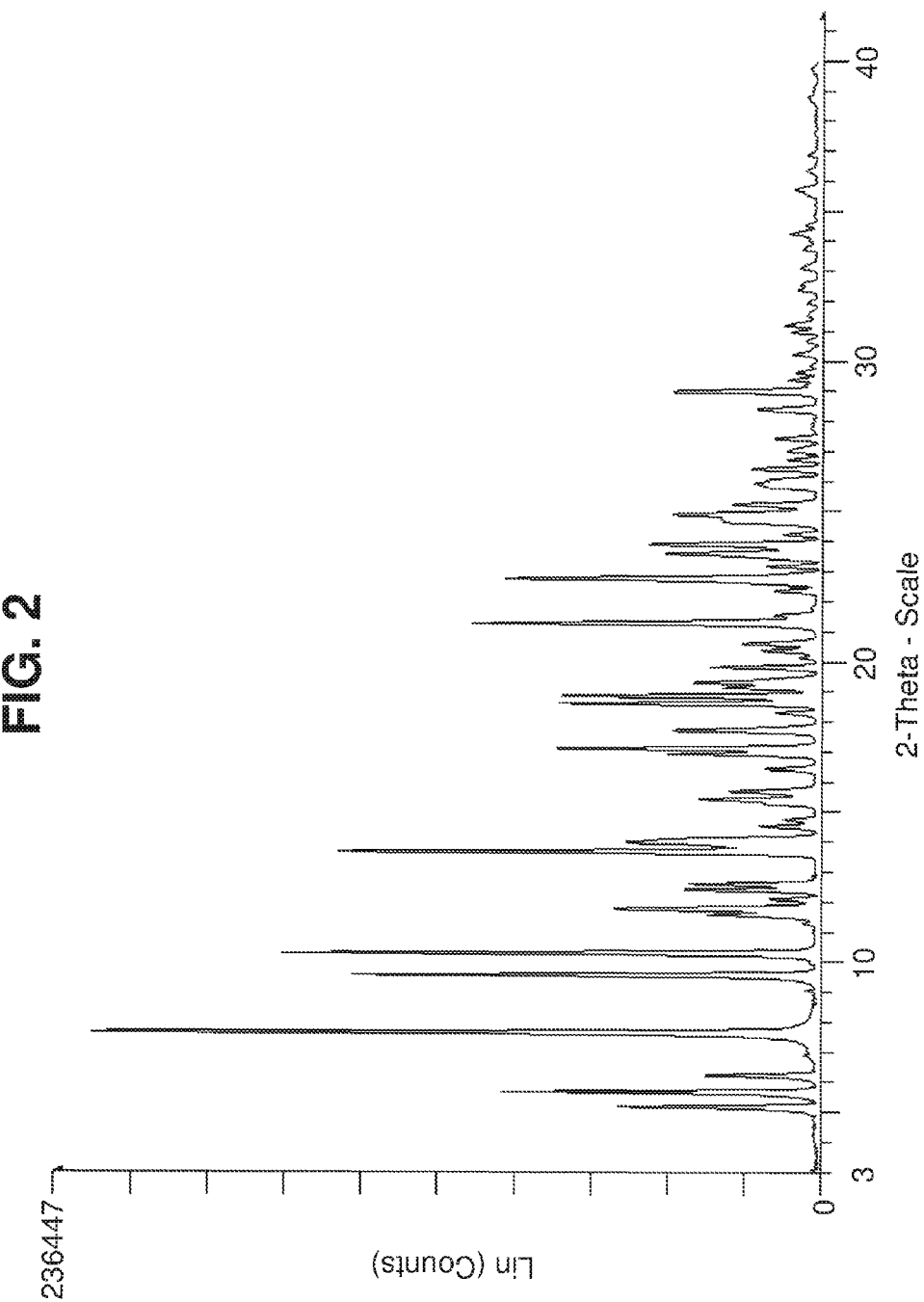
FIG. 2: PXRD pattern of crystalline hydrate of (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetradecine-3-carbonitrile (Form 2).

In specific embodiments, the hydrate Form 2 has a PXRD pattern comprising: (a) one, two, three, four, five, or more than five peaks selected from the group consisting of the peaks in Table 9 in °2θ±0.2 °2θ; (b) one, two, three, four or five peaks selected from the group consisting of the peaks in Table 10 in °2θ±0.2 °2θ; or (c) peaks at 2θ values essentially the same as shown in FIG. 2.

In some embodiments, the hydrate Form 2 has a Raman spectrum comprising wavenumber ($cm^{-1}$) values of: 1611 $cm^{-1}$±2 $cm^{-1}$. In other embodiments, the hydrate Form 2 has a Raman spectrum comprising wavenumber ($cm^{-1}$) values of: 2229 $cm^{-1}$±2 $cm^{-1}$. In other embodiments, the hydrate Form 2 has a Raman spectrum comprising wavenumber ($cm^{-1}$) values of: 1611 and 2229 $cm^{-1}$±2 $cm^{-1}$. In another embodiment, the hydrate Form 2 has a Raman spectrum comprising wavenumber ($cm^{-1}$) values of: 804, 2229 and 3061 $cm^{-1}$±2 $cm^{-1}$. In another embodiment, the hydrate Form 2 has a Raman spectrum comprising wavenumber ($cm^{-1}$) values of: 804, 1611, 2229 and 3061 $cm^{-1}$±2 $cm^{-1}$.

Figure 5:
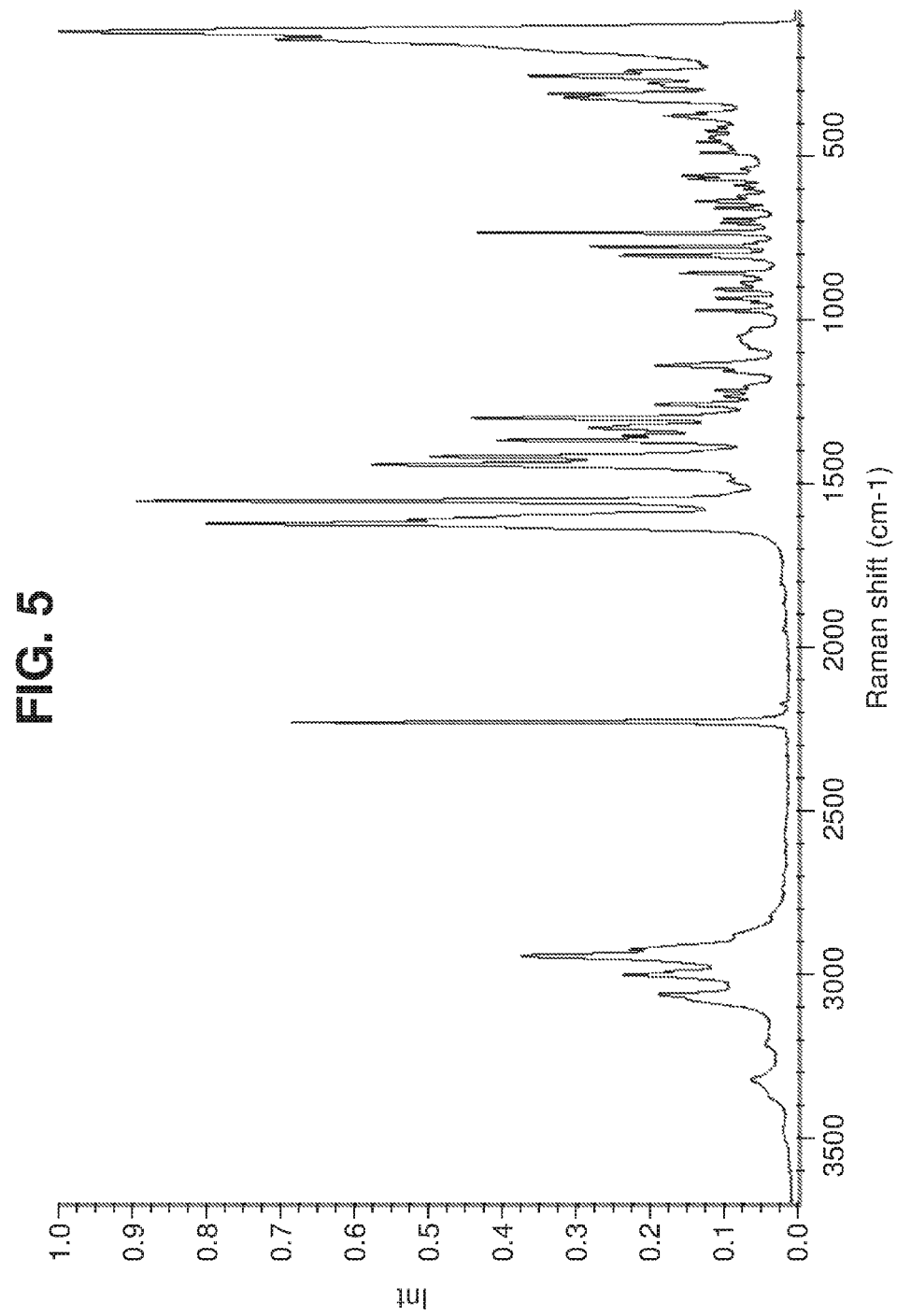
FIG. 5. FT-Raman pattern of crystalline hydrate of (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetradecine-3-carbonitrile (Form 2).

In specific embodiments, the hydrate Form 2 has a Raman spectrum comprising: (a) one, two, three, four, five, or more than five wavenumber ($cm^{-1}$) values selected from the group consisting of the values in Table 11 in $cm^{-1}$±2 $cm^{-1}$; (b) one, two, three, four, five, or more than five wavenumber ($cm^{-1}$) values selected from the group consisting of the values in Table 12 in $cm^{-1}$±2 $cm^{-1}$; or (c) wavenumber ($cm^{-1}$) values essentially the same as shown in FIG. 5.

In some embodiments, the hydrate Form 2 has a $^{13}C$ solid state NMR spectrum comprising the resonance (ppm) values of: 118.9 ppm±0.2 ppm. In another embodiment, the hydrate Form 2 has a $^{13}C$ solid state NMR spectrum comprising the resonance (ppm) values of: 168.2 ppm±0.2 ppm. In another embodiment, the hydrate Form 2 has a $^{13}C$ solid state NMR spectrum comprising the resonance (ppm) values of: 48.3 ppm±0.2 ppm. In another embodiment, the hydrate Form 2 has a $^{13}C$ solid state NMR spectrum comprising the resonance (ppm) values of: 118.9 and 168.2 ppm±0.2 ppm. In a further embodiment the hydrate Form 2 has a $^{13}C$ solid state NMR spectrum comprising the resonance (ppm) values of: 48.3, 118.9 and 168.2 ppm±0.2 ppm.

Figure 8:
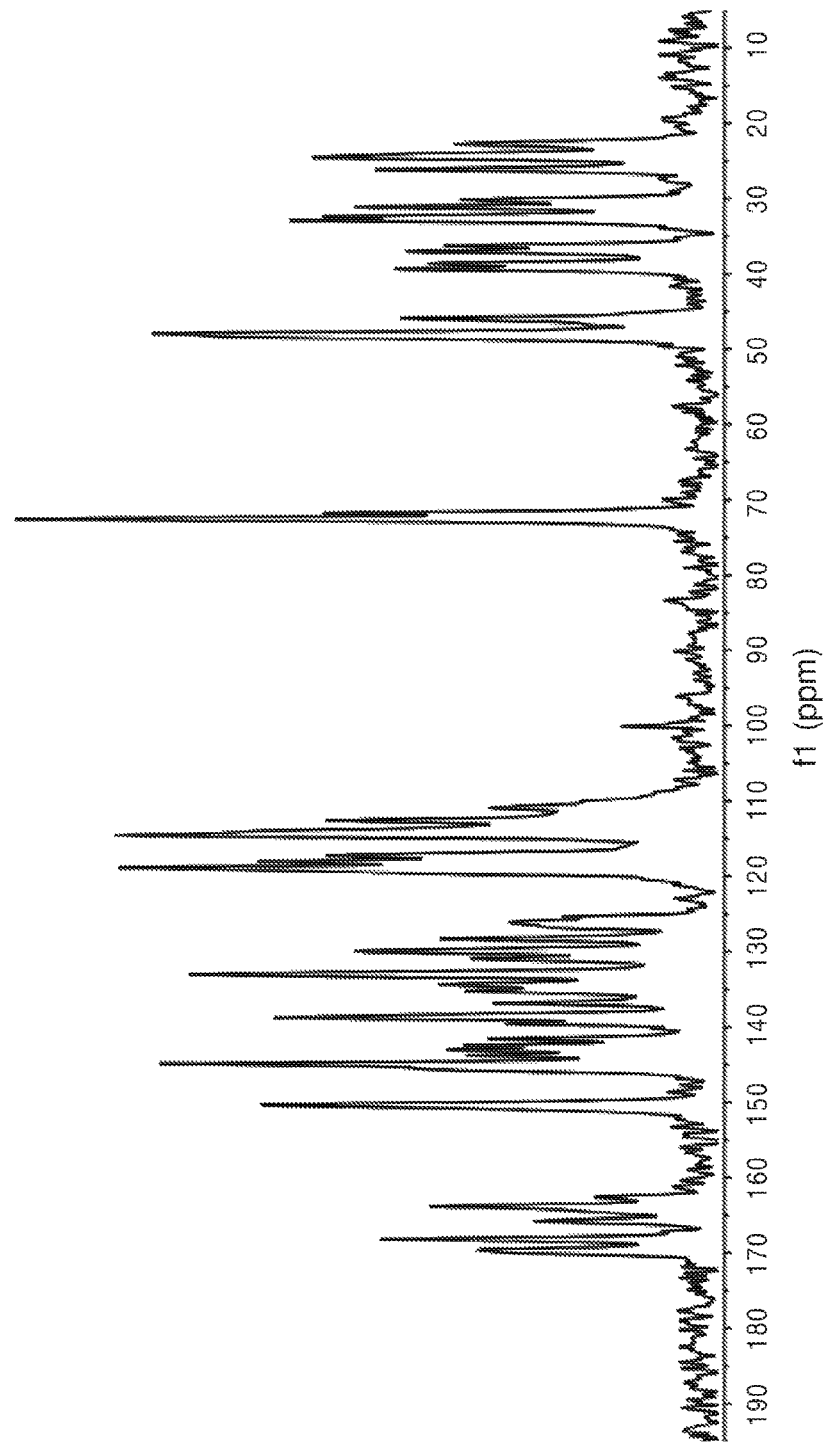
FIG. 8. Carbon CPMAS spectrum of crystalline hydrate of (10R)-7-amino-12-fluoro-2,10,16-trimethyl-15-oxo-10, 15,16,17-tetrahydro-2H-8,4-(metheno)pyrazolo[4,3-h][2,5,11]benzoxadiazacyclotetradecine-3-carbonitrile (Form 2).

In specific embodiments, the hydrate Form 2 has a $^{13}C$ solid state NMR spectrum (ppm) comprising: (a) one, two, three, four, five, or more than five resonance (ppm) values selected from the group consisting of the values in Table 13 in ppm±0.2 ppm; (b) one, two or three resonance (ppm) values selected from the group consisting of the values in Table 14 in ppm±0.2 ppm; or (c) resonance (ppm) values essentially the same as shown in FIG. 8.

Figure 11:
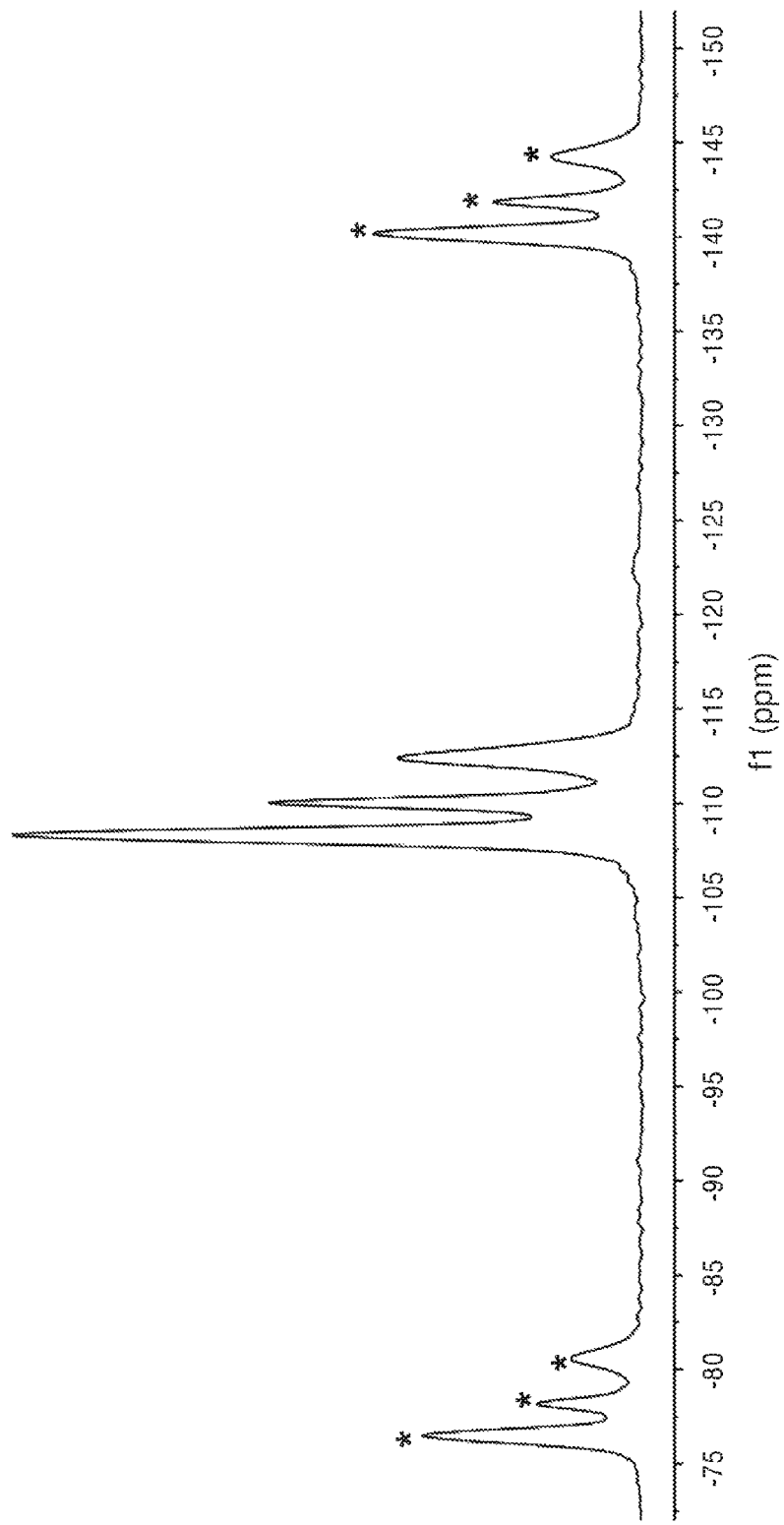
FIG. 11. Fluorine MAS spectrum of crystalline hydrate of (10R)-7-amino-12-fluoro-2,10,16-trimethyl-15-oxo-10,15, 16,17-tetrahydro-2H-8,4-(metheno)pyrazolo[4,3-h][2,5,11]benzoadiazacyclotetradecine-3-carbonitrile (Form 2). The peaks marked by asterisks are spinning sidebands.

In other embodiments, the hydrate Form 2 has a $^{19}F$ solid state NMR spectrum comprising a resonance (ppm) value of: −108.3 ppm±0.2 ppm. In another embodiment, the hydrate Form 2 has a $^{19}F$ solid state NMR spectrum (ppm) comprising: (a) one, two or three resonance (ppm) values in Table 15 in ppm±0.2 ppm; (b) the resonance (ppm) value in Table 16 in ppm±0.2 ppm; or (c) resonance (ppm) values essentially the same as shown in FIG. 11.

In further embodiments, the hydrate Form 2 is characterized by a combination of two, three or four of the embodiments described above with respect to Form 2 that are not inconsistent with each other. Exemplary embodiments that may be used to uniquely characterize the hydrate Form 2 are provided below.

In one embodiment, the hydrate Form 2 has a powder X-ray diffraction pattern comprising a peak at a 2θ value of: 5.6, 7.6, 9.5 and 10.2 °2θ±0.2 °2θ.

In one embodiment, the hydrate Form 2 has: (a) a powder X-ray diffraction pattern comprising a peak at a 2θ value of: 7.6 °2θ±0.2 °2θ; and (b) a Raman spectrum comprising wavenumber ($cm^{-1}$) values of: 1611 and 2229 $cm^{-1}$±2 $cm^{-1}$.

In one embodiment, the hydrate Form 2 has: (a) a powder X-ray diffraction pattern comprising a peak at a 2θ value of: 7.6 °2θ±0.2 °2θ; and (b) a $^{13}C$ solid state NMR spectrum comprising a resonance (ppm) value of: 118.9 ppm±0.2 ppm.

In one embodiment, the hydrate Form 2 has: (a) a powder X-ray diffraction pattern comprising a peak at a 2θ value of: 7.6 °2θ±0.2 °2θ; and (b) a $^{19}F$ solid state NMR spectrum comprising the resonance (ppm) value of: −108.3 ppm±0.2 ppm.

In one embodiment, the hydrate Form 2 has: (a) a powder X-ray diffraction pattern comprising a peak at a 2θ value of: 7.6 °2θ±0.2 °2θ; (b) a $^{13}C$ solid state NMR spectrum comprising a resonance (ppm) value of: 118.9 ppm±0.2 ppm; and (c) a $^{19}F$ solid state NMR spectrum comprising the resonance (ppm) value of: −108.3 ppm±0.2 ppm.

In another embodiment, the hydrate Form 2 has: (a) a Raman spectrum comprising a wavenumber ($cm^{-1}$) value of: 1611 $cm^{-1}$±2 $cm^{-1}$; and (b) a $^{13}C$ solid state NMR spectrum comprising a resonance (ppm) value of: 118.9 ppm±0.2 ppm.

In another embodiment, the hydrate Form 2 has: (a) a Raman spectrum comprising a wavenumber ($cm^{-1}$) value of: 1611 $cm^{-1}$±2 $cm^{-1}$; and (b) a $^{19}F$ solid state NMR spectrum comprising the resonance (ppm) value of: −108.3 ppm±0.2 ppm.

In another embodiment, the hydrate Form 2 has: (a) a Raman spectrum comprising a wavenumber ($cm^{-1}$) value of: 1611 $cm^{-1}$±2 $cm^{-1}$; and (b) a $^{13}C$ solid state NMR spectrum comprising a resonance (ppm) value of: 118.9 ppm±0.2 ppm; and (c) a $^{19}F$ solid state NMR spectrum comprising the resonance (ppm) value of: −108.3 ppm±0.2 ppm.

In another embodiment, the hydrate Form 2 has: (a) a Raman spectrum comprising wavenumber ($cm^{-1}$) values of: 1611 and 2229 $cm^{-1}$±2 $cm^{-1}$; and (b) a $^{13}C$ solid state NMR spectrum comprising a resonance (ppm) value of: 118.9 ppm±0.2 ppm.

In another embodiment, the hydrate Form 2 has: (a) a Raman spectrum comprising wavenumber ($cm^{-1}$) values of: 1611 and 2229 $cm^{-1}$±2 $cm^{-1}$; and (b) a $^{19}F$ solid state NMR spectrum comprising the resonance (ppm) value of: −108.3 ppm±0.2 ppm.

In another embodiment, the hydrate Form 2 has: (a) a Raman spectrum comprising wavenumber ($cm^{-1}$) values of: 1611 and 2229 $cm^{-1}$±2 $cm^{-1}$; (b) a $^{13}C$ solid state NMR spectrum comprising a resonance (ppm) value of: 118.9 ppm±0.2 ppm; and (c) a $^{19}F$ solid state NMR spectrum comprising the resonance (ppm) value of: −108.3 ppm±0.2 ppm.

In another embodiment, the hydrate Form 2 has a Raman spectrum comprising wavenumber ($cm^{-1}$) values of: 804, 2229 and 3061 $cm^{-1}$±2 $cm^{-1}$.

In another embodiment, the hydrate Form 2 has: (a) a powder X-ray diffraction pattern comprising a peak at a 2θ value of: 7.6 °2θ±0.2 °2θ; (b) a Raman spectrum comprising wavenumber ($cm^{-1}$) values of: 1611 $cm^{-1}$±2 $cm^{-1}$; and (c) a $^{13}C$ solid state NMR spectrum comprising a resonance (ppm) value of: 118.9 ppm±0.2 ppm.

In another embodiment, the hydrate Form 2 has: (a) a powder X-ray diffraction pattern comprising a peak at a 2θ value of: 7.6 °2θ±0.2 °2θ; (b) a Raman spectrum comprising a wavenumber (cm$^{-1}$) value of: 1611 cm$^{-1}$±2 cm$^{-1}$; and (c) a $^{19}$F solid state NMR spectrum comprising the resonance (ppm) value of: −108.3 ppm±0.2 ppm.

In another embodiment, the hydrate Form 2 has: (a) a powder X-ray diffraction pattern comprising a peak at a 2θ value of: 7.6 °2θ±0.2 °2θ; (b) a Raman spectrum comprising wavenumber (cm$^{-1}$) values of: 1611 cm$^{-1}$±2 cm$^{-1}$; (c) a $^{13}$C solid state NMR spectrum comprising a resonance (ppm) value of: 118.9 ppm±0.2 ppm; and (d) a $^{19}$F solid state NMR spectrum comprising the resonance (ppm) value of: −108.3 ppm±0.2 ppm.

In another embodiment, the hydrate Form 2 has a $^{19}$F solid state NMR spectrum comprising the resonance (ppm) value of: −108.3 ppm±0.2 ppm.

In another embodiment, the hydrate Form 2 has a $^{13}$C solid state NMR spectrum comprising resonance (ppm) values of: 48.3, 118.9 and 168.2 ppm±0.2 ppm.

In yet another embodiment, the hydrate Form 2 has: (a) a $^{19}$F solid state NMR spectrum comprising the resonance (ppm) value of: −108.3 ppm±0.2 ppm; and (b) a $^{13}$C solid state NMR spectrum comprising resonance (ppm) values of: 48.3, 118.9 and 168.2 ppm±0.2 ppm.

Crystalline Acetic Acid Solvate Form 3

In a third preferred aspect, the invention provides a crystalline acetic acid solvate (Form 3) of (10R)-7-amino-12-fluoro-2,10,16-trimethyl-15-oxo-10,15,16,17-tetrahydro-2H-8,4-(metheno)-pyrazolo[4,3-h][2,5,11]benzoxadiazacyclotetradecine-3-carbonitrile.

In one such embodiment, the acetic acid solvate Form 3 has a PXRD pattern comprising a peak at 2θ value of: 10.5 °2θ±0.2 °2θ. In another embodiment, the acetic acid solvate Form 3 has a PXRD pattern comprising a peak at 2θ value of: 11.4 °2θ±0.2 °2θ. In another embodiment, the acetic acid solvate Form 3 has a PXRD pattern comprising a peak at 2θ value of: 12.9 °2θ±0.2 °2θ. In another embodiment, the acetic acid solvate Form 3 has a PXRD pattern comprising a peak at 2θ value of: 14.5 °2θ±0.2 °2θ. In another embodiment, the acetic acid solvate Form 3 has a PXRD pattern comprising peaks at 2θ values of: 12.9 and 14.5 °2θ±0.2 °2θ. In another embodiment, the acetic acid solvate Form 3 has a PXRD pattern comprising peaks at 2θ values of: 10.5 and 12.9 °2θ±0.2 °2θ. In another embodiment, the acetic acid solvate Form 3 has a PXRD pattern comprising peaks at 2θ values of: 11.4 and 12.9 °2θ±0.2 °2θ. In another embodiment, the acetic acid solvate Form 3 has a PXRD pattern comprising peaks at 2θ values of: 10.5 and 11.4 °2θ±0.2 °2θ. In yet another embodiment, the acetic acid solvate Form 3 has a PXRD pattern comprising peaks at 2θ values of: 10.5, 11.4 and 12.9 °2θ±0.2 °2θ. In still another embodiment, the acetic acid solvate Form 3 has a PXRD pattern comprising peaks at 2θ values of: 10.5, 11.4, 12.9 and 14.5 °2θ±0.2 °2θ. In yet another embodiment, the acetic acid solvate Form 3 has a PXRD pattern comprising peaks at 2θ values of: 10.5, 11.4, 12.9, 14.5 and 15.3 °2θ±0.2 °2θ.

In some such embodiments, the PXRD pattern further comprises one or more peaks at 2θ values selected from the group consisting of: 17.9, 21.1, 22.5, 23.1 and 25.9 °2θ±0.2 °2θ. In specific embodiments, the acetic acid solvate Form 3 has a PXRD pattern comprising three or more peaks at 2θ values selected from the group consisting of: 10.5, 11.4, 12.9, 14.5, 15.3, 17.9, 21.1, 22.5, 23.1 and 25.9 °2θ±0.2 °2θ.

Figure 3:
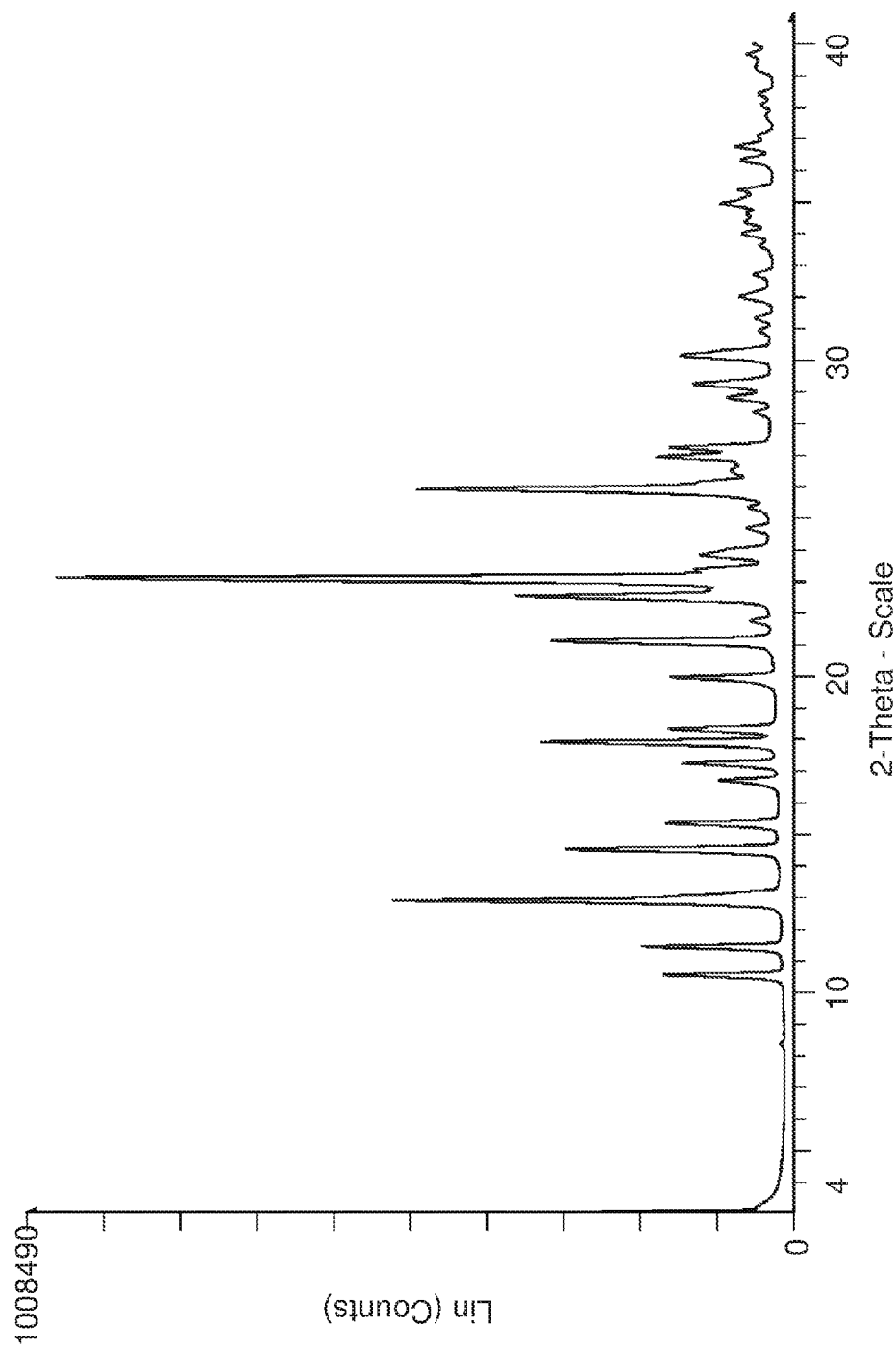
FIG. 3. PXRD pattern of crystalline acetic acid solvate of (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetradecine-3-carbonitrile (Form 3).

In specific embodiments, acetic acid solvate Form 3 has a PXRD pattern comprising: (a) one, two, three, four, five, or more than five peaks selected from the group consisting of the peaks in Table 17 in °2θ±0.2 °2θ; (b) one, two, three, four, or five peaks selected from the group consisting of the peaks in Table 18 in °2θ±0.2 °2θ; or (c) peaks at 2θ values essentially the same as shown in FIG. 3.

In some embodiments, the acetic acid solvate Form 3 has a Raman spectrum comprising wavenumber (cm$^{-1}$) values of: 2234 cm$^{-1}$±2 cm$^{-1}$. In other embodiments, the crystalline form has a Raman spectrum comprising wavenumber (cm$^{-1}$) values of: 1613 and 2234 cm$^{-1}$±2 cm$^{-1}$. In another embodiment, the acetic acid solvate Form 3 has a Raman spectrum comprising wavenumber (cm$^{-1}$) values of: 1552, 1613 and 2234 cm$^{-1}$±2 cm$^{-1}$. In another embodiment, the acetic acid solvate Form 3 has a Raman spectrum comprising wavenumber (cm$^{-1}$) values of: 1552, 1613, 1643, and 2234 cm$^{-1}$±2 cm$^{-1}$. In other embodiments, the acetic acid solvate Form 3 has a Raman spectrum comprising wavenumber (cm$^{-1}$) values of: 809 and 2234 cm$^{-1}$±2 cm$^{-1}$. In further embodiments, the acetic acid solvate Form 3 has a Raman spectrum comprising wavenumber (cm$^{-1}$) values of: 809, 2234 and 3055 cm$^{-1}$±2 cm$^{-1}$.

Figure 6:
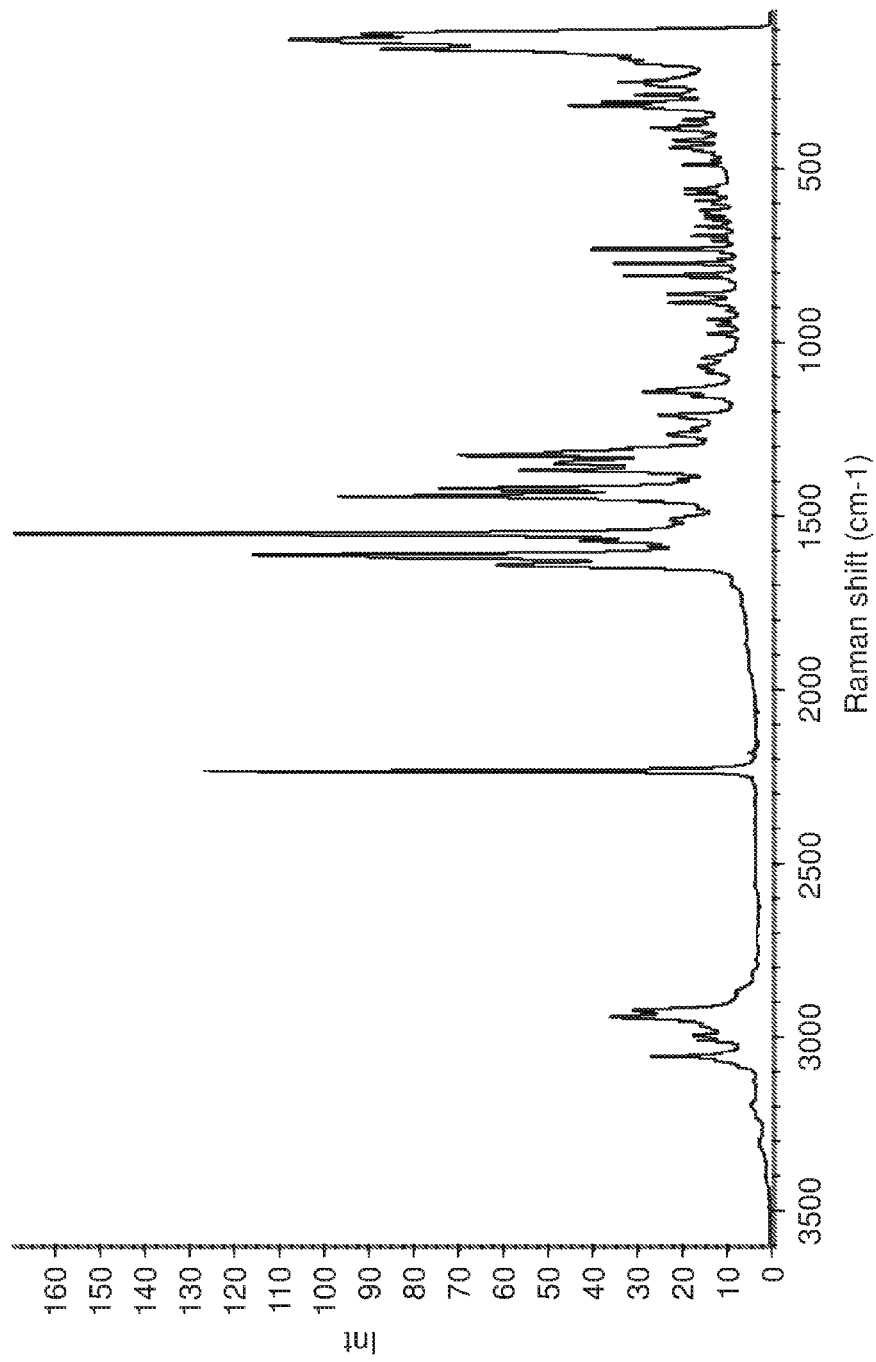
FIG. 6. FT-Raman pattern of crystalline acetic acid solvate of (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetradecine-3-carbonitrile (Form 3).

In specific embodiments, acetic acid solvate Form 3 has a Raman spectrum comprising: (a) one, two, three, four, five, or more than five wavenumber (cm$^{-1}$) values selected from the group consisting of the values in Table 19 in cm$^{-1}$±2 cm$^{-1}$; (b) one, two, three, four, five, or more than five wavenumber (cm$^{-1}$) values selected from the group consisting of the values in Table 20 in cm$^{-1}$±2 cm$^{-1}$; (c) one, two, three or four wavenumber (cm$^{-1}$) values selected from the group consisting of the values in Table 21 in cm$^{-1}$±2 cm$^{-1}$; or (d) wavenumber (cm$^{-1}$) values essentially the same as shown in FIG. 6.

In some embodiments, the acetic acid solvate Form 3 has a $^{13}$C solid state NMR spectrum comprising the resonance (ppm) values of: 22.8 ppm±0.2 ppm. In another embodiment, the acetic acid solvate Form 3 has a $^{13}$C solid state NMR spectrum comprising the resonance (ppm) values of: 140.7 ppm±0.2 ppm. In another embodiment, the acetic acid solvate Form 3 has a $^{13}$C solid state NMR spectrum comprising the resonance (ppm) values of: 170.3 ppm±0.2 ppm. In another embodiment, the acetic acid solvate Form 3 has a $^{13}$C solid state NMR spectrum comprising the resonance (ppm) values of: 22.8 and 140.7 ppm±0.2 ppm. In another embodiment, the acetic acid solvate Form 3 has a $^{13}$C solid state NMR spectrum comprising the resonance (ppm) values of: 140.7 and 170.3 ppm±0.2 ppm. In a further embodiment, the acetic acid solvate Form 3 has a $^{13}$C solid state NMR spectrum comprising the resonance (ppm) values of: 22.8, 140.7 and 170.3 ppm±0.2 ppm.

Figure 9:
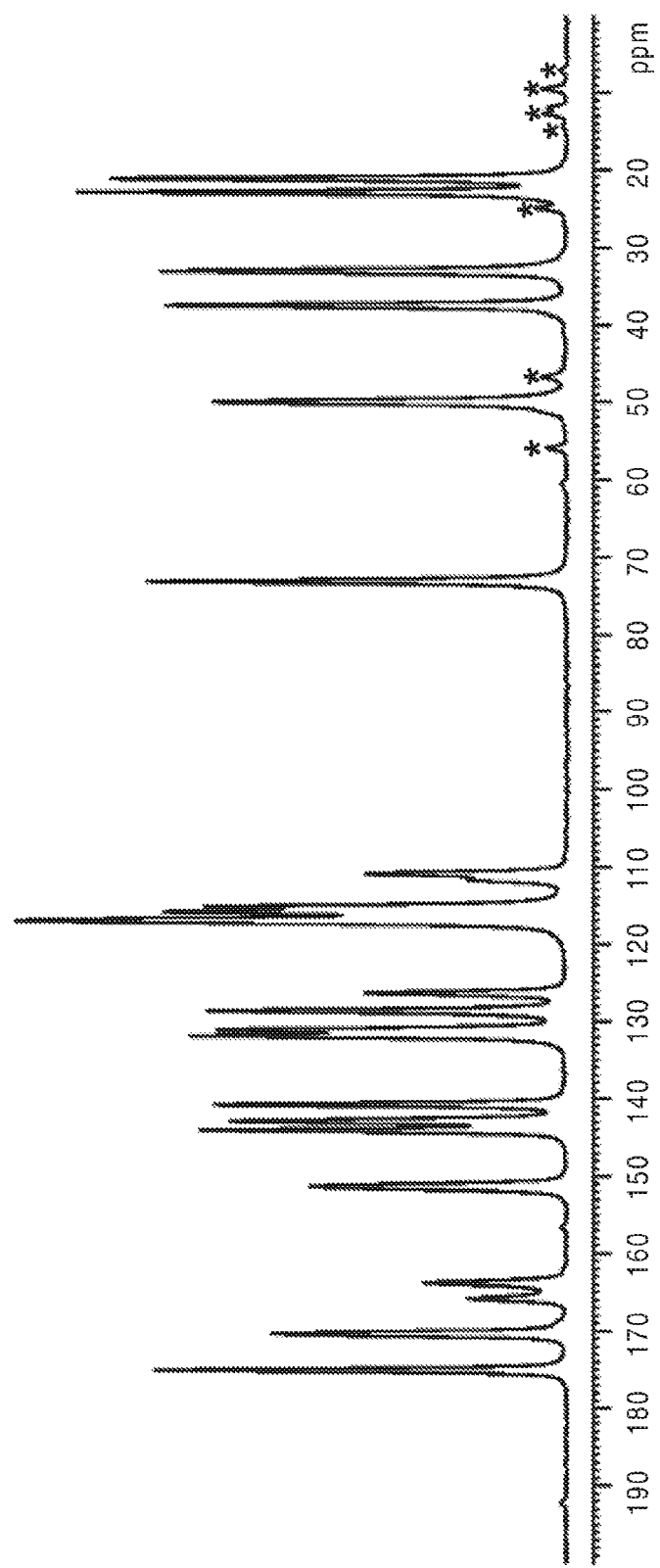
FIG. 9. Carbon CPMAS spectrum of crystalline acetic acid solvate of (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetradecine-3-carbonitrile (Form 3). The peaks marked by asterisks are spinning sidebands.

In specific embodiments, the acetic acid solvate Form 3 has a $^{13}$C solid state NMR spectrum (ppm) comprising: (a) one, two, three, four, five, or more than five resonance (ppm) values selected from the group consisting of the values in Table 22 in ppm±0.2 ppm; (b) one, two or three resonance (ppm) values selected from the group consisting of the values in Table 23 in ppm±0.2 ppm; or (c) resonance (ppm) values essentially the same as shown in FIG. 9.

Figure 12:
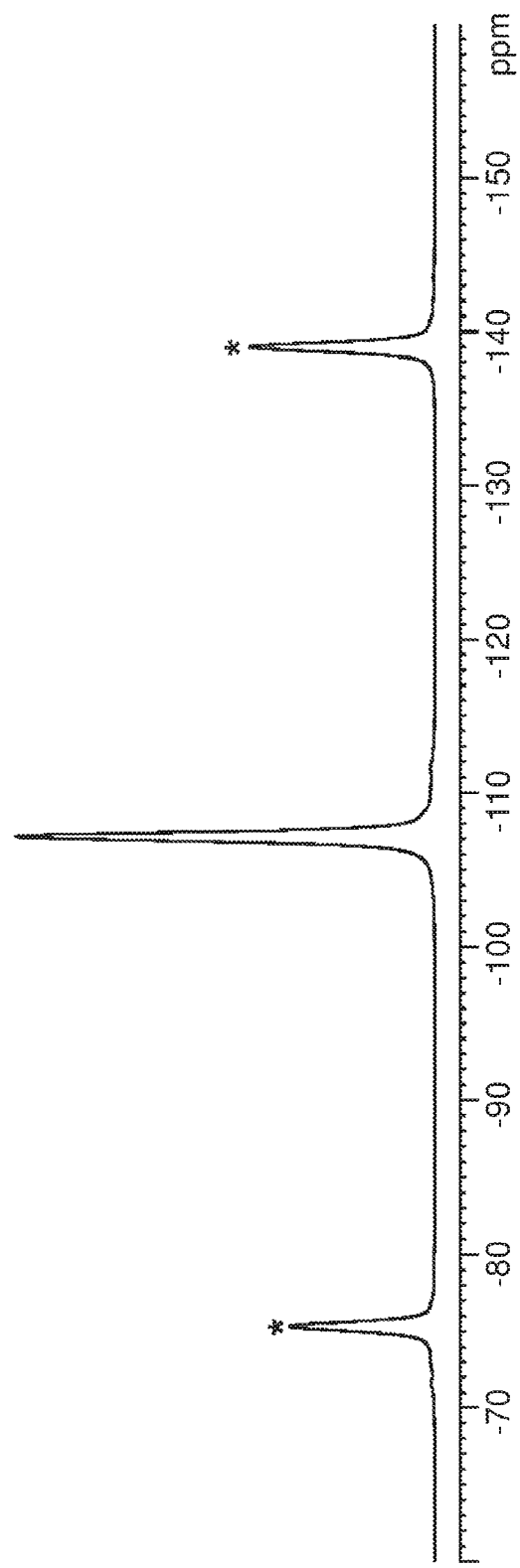
FIG. 12. Fluorine MAS spectrum of crystalline acetic acid solvate of (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetradecine-3-carbonitrile (Form 3). The peaks marked by asterisks are spinning sidebands.

In other embodiments of Form 3, the acetic acid solvate Form 3 has a $^{19}$F solid state NMR spectrum comprising a resonance (ppm) value of: −107.2 ppm±0.2 ppm. In another embodiment, the acetic acid solvate Form 3 has a $^{19}$F solid state NMR spectrum (ppm) comprising: (a) the resonance (ppm) value in Table 24 in ppm±0.2 ppm; or (b) resonance (ppm) values essentially the same as shown in FIG. 12.

In further embodiments, the acetic acid solvate Form 3 is characterized by a combination of two, three or four of the embodiments described above with respect to Form 3 that are not inconsistent with each other. Exemplary embodiments that may be used to uniquely characterize the crystalline acetic acid solvate Form 3 are provided below.

In one embodiment, the acetic acid solvate Form 3 has a powder X-ray diffraction pattern comprising a peak at a 2θ value of: 10.5, 11.4, 12.9, 14.5 and 15.3 °2θ±0.2 °2θ.

In one embodiment, the acetic acid solvate Form 3 has: (a) a powder X-ray diffraction pattern comprising a peak at a 2θ value of: 12.9 °2θ±0.2 °2θ; and (b) a Raman spectrum comprising wavenumber (cm$^{-1}$) values of: 809 and 2234 cm$^{-1}$±2 cm$^{-1}$.

In another embodiment, the acetic acid solvate Form 3 has: (a) a powder X-ray diffraction pattern comprising a peak at a 2θ value of: 12.9 °2θ±0.2 °2θ; (b) a $^{13}$C solid state NMR spectrum comprising a resonance (ppm) value of: 140.7 ppm±0.2 ppm; and (c) a $^{19}$F solid state NMR spectrum comprising the resonance (ppm) value of: −107.2 ppm±0.2 ppm.

In another embodiment, the acetic acid solvate Form 3 has: (a) a Raman spectrum comprising a wavenumber (cm$^{-1}$) value of: 2234 cm$^{-1}$±2 cm$^{-1}$; (b) a $^{13}$C solid state NMR spectrum comprising a resonance (ppm) value of: 140.7 ppm±0.2 ppm; and (c) a $^{19}$F solid state NMR spectrum comprising the resonance (ppm) value of: −107.2 ppm±0.2 ppm.

In another embodiment, the acetic acid solvate Form 3 has: (a) a powder X-ray diffraction pattern comprising a peak at a 2θ value of: 12.9 °2θ±0.2 °2θ; (b) a Raman spectrum comprising wavenumber (cm$^{-1}$) values of: 809 and 2234 cm$^{-1}$±2 cm$^{-1}$; (c) a $^{13}$C solid state NMR spectrum comprising a resonance (ppm) value of: 140.7 ppm±0.2 ppm; and (d) a $^{19}$F solid state NMR spectrum comprising the resonance (ppm) value of: −107.2 ppm±0.2 ppm.

In another embodiment, the acetic acid solvate Form 3 has a $^{13}$C solid state NMR spectrum comprising resonance (ppm) values of: 22.8, 140.7 and 170.3 ppm±0.2 ppm.

Additional combinations are described below. In one such embodiment, the crystalline acetic acid solvate Form 3 has a powder X-ray diffraction pattern comprising peaks at 2θ values of: (a) 10.5 °2θ±0.2 °2θ; (b) 11.4 °2θ±0.2 °2θ; (c) 10.5 and 11.4 °2θ±0.2 °2θ; (d) 10.5, 11.4 and 12.9 °2θ±0.2 °2θ; (e) 10.5, 11.4, 12.9 and 14.5 °2θ±0.2 °2θ; or (f) 10.5, 11.4, 12.9, 14.5 and 15.3 °2θ±0.2 °2θ; and a $^{13}$C solid state NMR spectrum comprising the resonance (ppm) values of: (a) 22.8 ppm±0.2 ppm; (b) 140.7 ppm±0.2 ppm; (c) 22.8 and 140.7 ppm±0.2 ppm; or (d) 22.8, 140.7 and 170.3 ppm±0.2 ppm.

In another embodiment, the crystalline acetic acid solvate Form 3 has a powder X-ray diffraction pattern comprising peaks at 2θ values of: (a) 10.5 °2θ±0.2 °2θ; (b) 11.4 °2θ±0.2 °2θ; (c) 10.5 and 11.4 °2θ±0.2 °2θ; (d) 10.5, 11.4 and 12.9 °2θ±0.2 °2θ; (e) 10.5, 11.4, 12.9 and 14.5 °2θ±0.2 °2θ; or (f) 10.5, 11.4, 12.9, 14.5 and 15.3 °2θ±0.2 °2θ; and a $^{19}$F solid state NMR spectrum comprising the resonance (ppm) value of: −107.2 ppm±0.2 ppm.

In another embodiment, the crystalline acetic acid solvate Form 3 has a powder X-ray diffraction pattern comprising peaks at 2θ values of: (a) 10.5 °2θ±0.2 °2θ; (b) 11.4 °2θ±0.2 °2θ; (c) 10.5 and 11.4 °2θ±0.2 °2θ; (d) 10.5, 11.4 and 12.9 °2θ±0.2 °2θ; (e) 10.5, 11.4, 12.9 and 14.5 °2θ±0.2 °2θ; or (f) 10.5, 11.4, 12.9, 14.5 and 15.3 °2θ±0.2 °2θ; and a Raman spectrum comprising wavenumber (cm$^{-1}$) values of: (a) 2234 cm$^{-1}$±2 cm$^{-1}$; (b) 2234 and 1613 cm$^{-1}$±2 cm$^{-1}$; (c) 2234, 1613 and 1552 cm$^{-1}$±2 cm$^{-1}$; or (d) 2234, 1613, 1643, and 1552 cm$^{-1}$±2 cm$^{-1}$; and In one embodiment, the crystalline acetic acid solvate Form 3 has a Raman spectrum comprising wavenumber (cm$^{-1}$) values of: (a) 2234 cm$^{-1}$±2 cm$^{-1}$; (b) 2234 and 1613 cm$^{-1}$±2 cm$^{-1}$; (c) 2234, 1613 and 1552 cm$^{-1}$±2 cm$^{-1}$; or (d) 2234, 1613, 1643, and 1552 cm$^{-1}$±2 cm$^{-1}$; and a powder X-ray diffraction pattern comprising peaks at 2θ values of: (a) 10.5 °2θ±0.2 °2θ; (b) 11.4 °2θ±0.2 °2θ; (c) 10.5 and 11.4 °2θ±0.2 °2θ; (d) 10.5, 11.4 and 12.9 °2θ±0.2 °2θ; (e) 10.5, 11.4, 12.9 and 14.5 °2θ±0.2 °2θ; or (f) 10.5, 11.4, 12.9, 14.5 and 15.3 °2θ±0.2 °2θ.

In another embodiment, the crystalline acetic acid solvate Form 3 has a Raman spectrum comprising wavenumber (cm$^{-1}$) values of: (a) 2234 cm$^{-1}$±2 cm$^{-1}$; (b) 2234 and 1613 cm$^{-1}$±2 cm$^{-1}$; (c) 2234, 1613 and 1552 cm$^{-1}$±2 cm$^{-1}$; or (d) 2234, 1613, 1643, and 1552 cm$^{-1}$±2 cm$^{-1}$; and a $^{13}$C solid state NMR spectrum comprising the resonance (ppm) values of: (a) 22.8 ppm±0.2 ppm; (b) 140.7 ppm±0.2 ppm; (c) 22.8 and 140.7 ppm±0.2 ppm; or (d) 22.8, 140.7 and 170.3 ppm±0.2 ppm.

In another embodiment, the crystalline acetic acid solvate Form 3 has a Raman spectrum comprising wavenumber (cm$^{-1}$) values of: (a) 2234 cm$^{-1}$±2 cm$^{-1}$; (b) 2234 and 1613 cm$^{-1}$±2 cm$^{-1}$; (c) 2234, 1613 and 1552 cm$^{-1}$±2 cm$^{-1}$; or (d) 2234, 1613, 1643, and 1552 cm$^{-1}$±2 cm$^{-1}$; and a $^{19}$F solid state NMR spectrum comprising the resonance (ppm) value of: −107.2 ppm±0.2 ppm.

In yet another embodiment, the crystalline acetic acid solvate Form 3 has a $^{13}$C solid state NMR spectrum comprising the resonance (ppm) values of: (a) 22.8 ppm±0.2 ppm; (b) 140.7 ppm±0.2 ppm; (c) 22.8 and 140.7 ppm±0.2 ppm; or (d) 22.8, 140.7 and 170.3 ppm±0.2 ppm; and a powder X-ray diffraction pattern comprising peaks at 2θ values of: (a) 10.5 °2θ±0.2 °2θ; (b) 11.4 °2θ±0.2 °2θ; (c) 10.5 and 11.4 °2θ±0.2 °2θ; (d) 10.5, 11.4 and 12.9 °2θ±0.2 °2θ; (e) 10.5, 11.4, 12.9 and 14.5 °2θ±0.2 °2θ; or (f) 10.5, 11.4, 12.9, 14.5 and 15.3 °2θ±0.2 °2θ.

In a further embodiment, the crystalline acetic acid solvate Form 3 has a $^{13}$C solid state NMR spectrum comprising the resonance (ppm) values of: (a) 22.8 ppm±0.2 ppm; (b) 140.7 ppm±0.2 ppm; (c) 22.8 and 140.7 ppm±0.2 ppm; or (d) 22.8, 140.7 and 170.3 ppm±0.2 ppm; and a $^{19}$F solid state NMR spectrum comprising the resonance (ppm) value of: −107.2 ppm±0.2 ppm.

In another embodiment, the crystalline acetic acid solvate Form 3 has a $^{13}$C solid state NMR spectrum comprising the resonance (ppm) values of: (a) 22.8 ppm±0.2 ppm; (b) 140.7 ppm±0.2 ppm; (c) 22.8 and 140.7 ppm±0.2 ppm; or (d) 22.8, 140.7 and 170.3 ppm±0.2 ppm; and a Raman spectrum comprising wavenumber (cm$^{-1}$) values of: (a) 2234 cm$^{-1}$±2 cm$^{-1}$; (b) 2234 and 1613 cm$^{-1}$±2 cm$^{-1}$; (c) 2234, 1613 and 1552 cm$^{-1}$±2 cm$^{-1}$; or (d) 2234, 1613, 1643, and 1552 cm$^{-1}$+2 cm$^{-1}$.

In one embodiment, the crystalline acetic acid solvate Form 3 has a $^{19}$F solid state NMR spectrum comprising the resonance (ppm) value of: −107.2 ppm±0.2 ppm; and a powder X-ray diffraction pattern comprising peaks at 2θ values of: (a) 10.5 °2θ±0.2 °2θ; (b) 11.4 °2θ±0.2 °2θ; (c) 10.5 and 11.4 °2θ±0.2 °2θ; (d) 10.5, 11.4 and 12.9 °2θ±0.2 °2θ; (e) 10.5, 11.4, 12.9 and 14.5 °2θ±0.2 °2θ; or (f) 10.5, 11.4, 12.9, 14.5 and 15.3 °2θ±0.2 °2θ.

In another embodiment, the crystalline acetic acid solvate Form 3 has a $^{19}$F solid state NMR spectrum comprising the resonance (ppm) value of: −107.2 ppm±0.2 ppm; and a $^{13}$C solid state NMR spectrum comprising the resonance (ppm) values of: (a) 22.8 ppm±0.2 ppm; (b) 140.7 ppm±0.2 ppm; (c) 22.8 and 140.7 ppm±0.2 ppm; or (d) 22.8, 140.7 and 170.3 ppm±0.2 ppm.

In another embodiment, the crystalline acetic acid solvate Form 3 has a $^{19}$F solid state NMR spectrum comprising the resonance (ppm) value of: −107.2 ppm±0.2 ppm; and a Raman spectrum comprising wavenumber (cm$^{-1}$) values of: (a) 2234 cm$^{-1}$±2 cm$^{-1}$; (b) 2234 and 1613 cm$^{-1}$±2 cm⁻¹; (c) 2234, 1613 and 1552 cm⁻¹±2 cm⁻¹; or (d) 2234, 1613, 1643, and 1552 cm⁻¹±2 cm⁻¹.

In a further embodiment, the crystalline acetic acid solvate Form 3 of (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetradecine-3-carbonitrile, is characterized by one, two, three or four of the following: a powder X-ray diffraction pattern comprising peaks at 2θ values of: 10.5 and 11.4 °2θ±0.2 °2θ; a Raman spectrum comprising wavenumber (cm⁻¹) values of: 2234 and 1613 cm⁻¹±2 cm⁻¹; a ¹³C solid state NMR spectrum comprising the resonance (ppm) values of: 22.8 and 140.7 ppm±0.2 ppm; or a ¹⁹F solid state NMR spectrum comprising the resonance (ppm) value of: −107.2 ppm±0.2 ppm.

In another embodiment, the crystalline acetic acid solvate Form 3 of (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetradecine-3-carbonitrile, is characterized by one, two, three or four of the following: a powder X-ray diffraction pattern comprising peaks at 2θ values of: about 10.5, 11.4, and 12.9 °2θ±0.2 °2θ; a Raman spectrum comprising wavenumber (cm⁻¹) values of: about 2234, 1613, 1643, and 1552 cm⁻¹±2 cm⁻¹; a ¹³C solid state NMR spectrum comprising the resonance (ppm) values of: 22.8, 140.7, and 170.3 ppm±0.2 ppm; or a ¹⁹F solid state NMR spectrum comprising the resonance (ppm) value of: −107.2 ppm±0.2 ppm.

In a further embodiment, the crystalline acetic acid solvate Form 3 is characterized by one, two, three or four of the following: a powder X-ray diffraction pattern comprising peaks at 2θ values of: about 10.5 and 11.4 °2θ±0.2 °2θ; a Raman spectrum comprising wavenumber (cm⁻¹) values of: about 2234 and 1613 cm⁻¹±2 cm⁻¹; a ¹³C solid state NMR spectrum comprising the resonance (ppm) values of: 22.8 and 140.7 ppm±0.2 ppm; or a ¹⁹F solid state NMR spectrum comprising the resonance (ppm) value of: −107.2 ppm±0.2 ppm.

In another embodiment, the crystalline acetic acid solvate is characterized by one, two, three or four of the following: a powder X-ray diffraction pattern comprising peaks at 2θ values of: about 10.5, 11.4 and 12.9 °2θ±0.2 °2θ; a Raman spectrum comprising wavenumber (cm⁻¹) values of: about 2234, 1613, 1643 and 1552 cm⁻¹±2 cm⁻¹; a ¹³C solid state NMR spectrum comprising the resonance (ppm) values of: 22.8, 140.7 and 170.3 ppm±0.2 ppm; or a ¹⁹F solid state NMR spectrum comprising the resonance (ppm) value of: −107.2 ppm±0.2 ppm.

In another aspect, the invention provides a pharmaceutical composition comprising a crystalline form of (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetradecine-3-carbonitrile according to any of the aspects or embodiments described herein, and a pharmaceutically acceptable excipient. In some embodiments, the pharmaceutical composition comprises a crystalline acetic acid solvate or a crystalline hydrate of (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetradecine-3-carbonitrile, and a pharmaceutically acceptable excipient. In a particular embodiment, the pharmaceutical composition comprises a crystalline acetic acid solvate of (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetradecine-3-carbonitrile, and a pharmaceutically acceptable excipient. In a specific embodiment, the crystalline acetic acid solvate is the solvate Form 3 disclosed herein. In another embodiment, the pharmaceutical composition comprises a crystalline hydrate of (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetradecine-3-carbonitrile, and a pharmaceutically acceptable excipient. In specific embodiments, the crystalline hydrate is the hydrate Form 1 or Form 2 disclosed herein.

In another aspect, the invention provides method of treating abnormal cell growth in a mammal, preferably a human, comprising administering to the mammal a therapeutically effective amount of a pharmaceutical composition of the invention. In some embodiments, the abnormal cell growth is mediated by an anaplastic lymphoma kinase (ALK). In some such embodiments, the ALK is a genetically altered ALK. In other embodiments, the abnormal cell growth is mediated by ROS1 kinase. In some such embodiments, the ROS1 kinase is a genetically altered ROS1 kinase. In frequent embodiments, the abnormal cell growth is cancer, in particular NSCLC. In some such embodiments, the NSCLC is mediated by genetically altered ALK or genetically altered ROS1.

Pharmaceutical compositions of the present invention may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Tablets typically contain from 1-30% of (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetradecine-3-carbonitrile on a w/w basis. Microcrystalline cellulose and dibasic calcium phosphate may be used as tablet fillers, and sodium starch glycolate may be used as a disintegrant. Magnesium stearate may be used as a lubricant and can be incorporated into the tablet or added externally during compression.

Methods of preparing various pharmaceutical compositions with a specific amount of active compound are known, or will be apparent, to those skilled in this art. For examples, see *Remington's Pharmaceutical Sciences*, Mack Publishing Company, Easter, Pa., 15th Edition (1975).

EXAMPLES

The examples and preparations provided below further illustrate and exemplify particular aspects and embodiments of the invention. It is to be understood that the scope of the present invention is not limited by the scope of the following examples.

General Method 1. Powder X-Ray Diffraction (PXRD)

The PXRD data in FIGS. 1, 2, 3 and 13 were collected according to the following general protocol.

Instrument Method:

The powder X-ray diffraction (PXRD) pattern was obtained using a Bruker-AXS Ltd. D4 powder X-ray diffractometer fitted with an automatic sample changer, a theta-theta goniometer, automatic beam divergence slit, and a LynxEye detector. The sample was prepared for analysis by mounting on a low background cavity silicon wafer specimen mount. The specimen was rotated whilst being irradiated with copper K-alpha$_1$ X-rays (wavelength=1.5406 Ångstroms) with the X-ray tube operated at 40 kV/40 mA. The analyses were performed with the goniometer running in continuous mode set for a 12 second count per 0.040° step over a two theta (2θ) range of 3° to 40°. Data were collected at ambient conditions.

Peak picking method: Data were analyzed using Bruker DIFFRAC Plus software (Release 2003). PXRD data files (.raw) for Forms 1 and 2 were background corrected prior to peak searching. Generally, a Threshold value of 1 and a Width value of 0.3 were used to make preliminary peak assignments. The output of automated assignments was visually checked to ensure validity and adjustments manually made if necessary.

To perform an X-ray diffraction measurement on a Bragg-Brentano instrument like the Bruker system used for measurements reported herein, the sample is typically placed into a holder which has a cavity or zero background holders. The sample holder is then placed into the instrument. The incident X-ray beam is directed at the sample, initially at a small angle relative to the plane of the holder, and then moved through an arc that continuously increases the angle between the incident beam and the plane of the holder. Measurement differences associated with such X-ray powder analyses result from a variety of factors including: (a) errors in sample preparation (e.g., sample height), (b) instrument errors (e.g. flat sample errors), (c) calibration errors, (d) operator errors (including those errors present when determining the peak locations), and (e) the nature of the material (e.g. preferred orientation and transparency errors). Calibration errors and sample height errors often result in a shift of all the peaks in the same direction. Small differences in sample height when using a flat holder will lead to large displacements in PXRD peak positions. A systematic study showed that, using a Shimadzu XRD-6000 in the typical Bragg-Brentano configuration, sample height difference of 1 mm lead to peak shifts as high as 1 °2θ (Chen et al.; J Pharmaceutical and Biomedical Analysis, 2001; 26,63). These shifts can be identified from the X-ray Diffractogram and can be eliminated by compensating for the shift (applying a systematic correction factor to all peak position values) or recalibrating the instrument. As mentioned above, it is possible to rectify measurements from the various machines by applying a systematic correction factor to bring the peak positions into agreement. In general, this correction factor will bring the measured peak positions from the Bruker into agreement with the expected peak positions and may be in the range of 0 to 0.2 °2θ.

Measurements using a different wavelength will result in different shifts according to the Bragg equation—nλ=2d sin θ. Such further PXRD patterns generated by use of alternative wavelengths are considered to be alternative representations of the PXRD patterns of the crystalline materials of the present invention and as such are within the scope of the present invention.

General Method 2. Raman Spectroscopy: Nicolet NXR FT-Raman

The Raman spectral data in FIGS. 4, 5, 6 and 14 were collected according to the following general protocol.

Instrument Method:

Raman spectra were collected using a Nicolet NXR FT-Raman accessory attached to the FT-IR bench. The spectrometer is equipped with a 1064 nm Nd: YVO4 laser and a liquid nitrogen cooled Germanium detector or a room temperature InGaAs detector. Prior to data acquisition, instrument performance and calibration verifications were conducted using polystyrene. Samples were analyzed in glass NMR tubes that were spun during spectral collection. The spectra were collected using 0.5 W of laser power and 512 co-added scans. The collection range was 3700-50 cm$^{-1}$. All spectra were recorded using 2 cm$^{-1}$ resolution and Happ-Genzel apodization.

Peak Picking Method:

The intensity was normalized to 1 prior to peak picking. Peaks were manually identified using the Thermo Nicolet Omnic 7.3 software. Peak position was picked at the peak maximum, and peaks were only identified as such, if there was a slope on each side; shoulders on peaks were not included. The peak position has been rounded to the nearest whole number using standard practice (0.5 rounds up, 0.4 rounds down). Peaks with normalized peak intensity between (1-0.75), (0.74-0.3), (0.29-0) were labeled as strong, medium and weak respectively.

General Method 3. Solid State NMR (ssNMR) Spectroscopy:

The carbon CPMAS and fluorine MAS ssNMR data in FIGS. 7, 8, 9, 10, 11, 12, 15 and 16 were collected according to the following general protocol.

Instrument Method: ssNMR spectra were collected at a temperature set point of 0° C. (Forms 1 and 2) or at ambient conditions (Form 3) on a Bruker-Biospin 2.5 mm CPMAS probe positioned into a wide-bore Bruker-Biospin Avance III 500 MHz (1H frequency) NMR spectrometer. The packed rotor was oriented at the magic angle and spun at 15.0 kHz. The carbon solid state spectra were collected using a proton decoupled cross-polarization magic angle spinning (CPMAS) experiment. The cross-polarization contact time was set to 2.0 ms. Phase modulated proton decoupling at approximately 100 kHz was applied during acquisition. The carbon spectra were referenced using an external standard of crystalline adamantane, setting its upfield resonance to 29.5 ppm. The fluorine solid state spectra were collected using a proton decoupled magic angle spinning (MAS) experiment. Phase modulated proton decoupling at approximately 100 kHz was applied during acquisition. The fluorine spectra were referenced using an external standard of trifluoroacetic acid (50% V/V in H2O), setting its resonance to −76.54 ppm.

Peak Picking Method:

Automatic peak picking was performed using Bruker-BioSpin TopSpin version 3.1 software. Generally, a threshold value of 5% relative intensity was used to preliminary select peaks. The output of the automated peak picking was visually checked to ensure validity and adjustments manually made if necessary. Although specific $^{13}$C and $^{19}$F solid state NMR peak values are reported herein there does exist a range for these peak values due to differences in instruments, samples, and sample preparation. This is common practice in the art of solid state NMR because of the variation inherent in peak values. A typical variability for a $^{13}$C or $^{19}$F chemical shift (ppm) x-axis value is on the order of plus or minus 0.2 ppm for a crystalline solid.

Preparation of Synthetic Intermediates

Preparation of (R)-methyl 2-(1-((2-amino-5-bromopyridin-3-yl)oxy)ethyl)-4-fluorobenzoate (7)

in MTBE (methyl tertiary-butyl ether) (200 ml). A solution of diethanolamine (31 g, 296 mmol) in ethanol/THF (15 ml/30 ml) was added via addition funnel, to the reaction mixture under an ice bath. The formation of a white precipitate was observed. The suspension was heated at reflux for 2 hours then cooled to room temperature, filtered and the mother liquids concentrated in vacuo. The residue was suspended in heptane/EtOAc (7:3, 200 ml) and again filtered. This procedure was repeated until no more solids could be observed after the liquids were concentrated. The final yellow oil was purified by column chromatography (eluent: cyclohexane/EtOAc 99:1 to 96:4). The resulting colorless oil was further purified by recrystallization from heptanes, to give alcohol compound 2 (25 g, 80% yield, 99% purity and 96% ee) as white crystals. $^1$H NMR (400 MHz, CDCl$_3$) δ 7.73 (dd, 1H), 7.32 (dd, 1H), 6.74 (ddd, 1H), 4.99-5.04 (m, 1H), 2.01 (d, 1H), 1.44 (d, 3H). LCMS-ES: No ionization, Purity 99%. Chiral GC (column CP-Chirasil-DexnCB): 96% ee; Rt (minor) 17.7 minutes and Rt (major) 19.4 minutes.

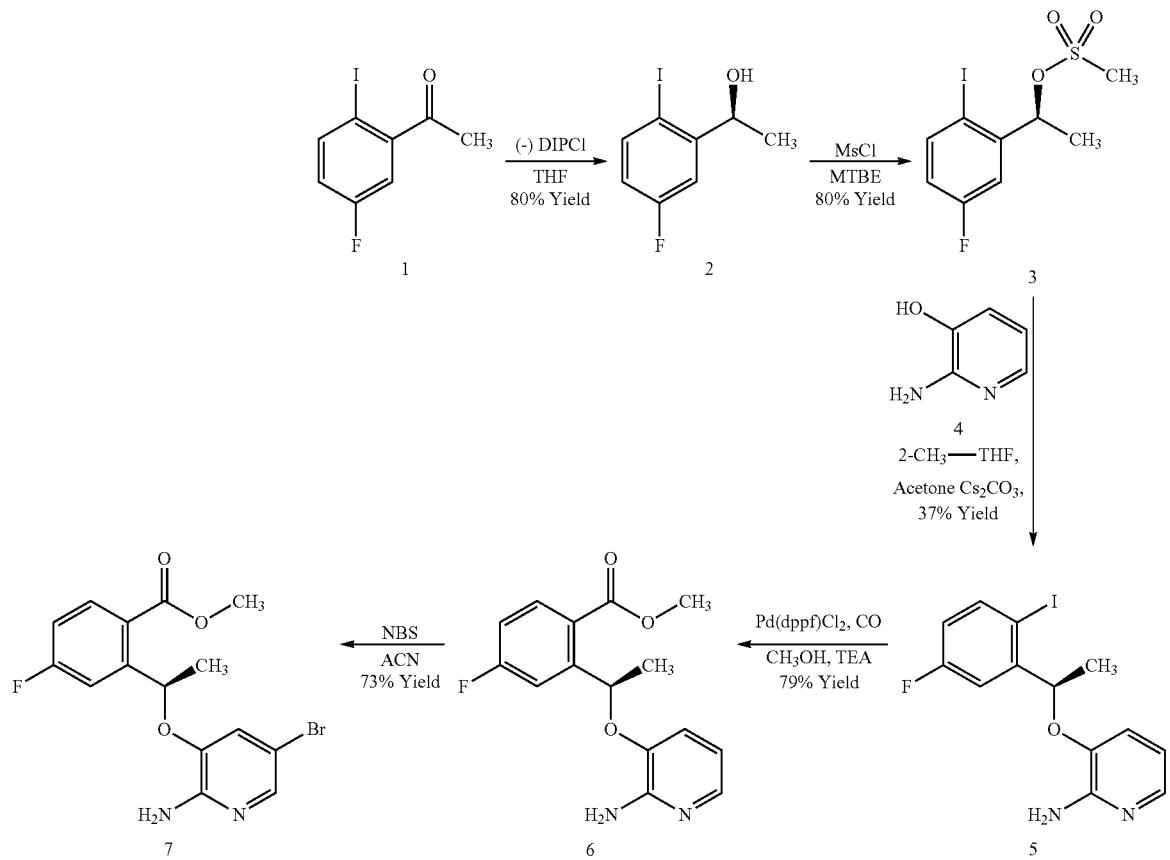

Step 1:

A solution of (−)-DIPCl ((−)-B-chlorodiisopinocampheylborane) (57.1 g, 178 mmol) in THF (tetrahydrofuran) (100 ml) was cooled to −20 to −30° C. A solution of compound 1 (31.3 g, 119 mmol) in THF (100 ml) was then added dropwise, via addition funnel (30 min addition). The reaction was left to warm up to room temperature (RT). After 2 h, the reaction was cooled to −30° C. and another portion of (−)-DIPCl (38.0 g, 119 mmol) was added. After 30 min, the reaction was allowed to warm to RT and after 1 h, the solvents were removed in vacuo and the residue re-dissolved Step 2:

A solution of compound 2 (22 g, 83 mmol) in MTBE (350 mL) was cooled under an ice bath and triethylamine (23 mL, 166 mmol) followed by mesyl chloride (9.6 mL, 124 mmol) were added drop-wise. The reaction was then warmed to RT and stirred for 3 h. The reaction mixture was filtered and the solids washed with EtOAc. The mother liquids were concentrated in vacuo to give compound 3 (35 g, 80% yield) as a pale yellow oil. This material was taken into the following step without further purification. $^1$H NMR (400 MHz, CDCl$_3$) δ 7.78 (dd, 1H), 7.24 (dd, 1H), 6.82 (ddd, 1H), 2.92 (s, 3H), 1.64 (d, 3H). LCMS-ES no ionization.

Step 3:

A suspension of Cs$_2$CO$_3$ (65 g, 201 mmol) and compound 4 (13.3 g, 121 mmol) in 2-CH$_3$-THF (2-methyltetrahydrofuran) (600 mL) and acetone (300 mL) was stirred at RT for 30 minutes then heated at 40° C. before drop-wise addition of a solution of compound 3 (34.4 g, 80 mmol) in 2-CH$_3$-THF (300 mL) via addition funnel. The resulting mixture was left stirring at 75-80° C. for 24 h. The reaction was then filtered through CELITE® with MTBE, the solvents removed in vacuo and the residue purified by column chromatography over silica gel which was eluted with cyclohexane/EtOAc (9:1 to 1:1) to give compound 5 (14.3 g, 39% yield, 90% ee) as a white solid. The solids were then recrystallized from heptane/EtOAc to give compound 5 (10.8 g, 37% yield, 95% ee). $^1$H NMR (400 MHz, CDCl$_3$) δ 7.38 (dd, 1H), 7.62 (dd, 1H), 7.10 (dd, 1H), 6.75 (ddd, 1H), 6.44-6.51 (m, 2H), 5.34-5.39 (m, 1H), 4.73 (br s, 2H), 1.61 (d, 3H). LCMS-ES m/z 359 [M+H]$^+$. HPLC (Chiralpak IC 4.6×250 mm): 95% ee; Rt (minor) 10.4 minutes; Rt (major) 14.7 minutes; eluent: Heptane 80%/IPA 20% with 0.2% DEA, 0.7 mL/min.

Step 4:

Compound 5 (20 g, 57 mmol) was dissolved in methanol (300 mL), and sequentially treated with triethylamine (TEA) (15.4 mL, 113 mmol) and PdCl$_2$(dppf) (1,1'-bis(diphenylphosphino)ferrocene]dichloropalladium(II)) (4.1 g, 5.7 mmol). This mixture was heated at 100° C. for 16 hours, under a 100 psi carbon monoxide atmosphere. LCMS indicated consumption of starting material. The reaction mixture was filtered through a pad of CELITE®, and the filtrate evaporated to a brown oil. The crude product was purified by flash chromatography over silica gel which was eluted with 50% to 75% ethyl acetate in cyclohexane, affording the pure product 6 as a brick-red solid (13.0 g, 79% yield). $^1$H NMR (400 MHz, CDCl$_3$) δ 1.65 (d, 3H), 3.94 (s, 3H), 4.75 (br s, 2H), 6.32 (q, 1H), 6.42 (dd, 1H), 6.61 (dd, 1H), 7.00 (ddd, 1H), 7.28 (dd, 1H), 7.60 (dd, 1H), 8.03 (dd, 1H). LCMS ES m/z 291 for [M+H]$^+$.

Step 5:

Compound 6 (13.0 g, 45 mmol) was dissolved in acetonitrile (195 mL), and cooled to <10° C. in an ice water bath. NBS (N-bromosuccinimide) (7.9 g, 45 mmol) was added drop-wise to the cooled reaction mixture as a solution in acetonitrile (195 mL), monitoring the internal temperature to ensure it did not rise above 10° C. After addition was complete, the mixture was stirred for 15 minutes. Thin layer chromatography (TLC) (1:1 cyclohexane/ethyl acetate) showed consumption of starting material. The reaction mixture was evaporated, and the residue redissolved in ethyl acetate (400 mL), and washed with 2M aqueous NaOH (2×300 mL), and 10% aqueous sodium thiosulfate solution (300 mL). The organic extracts were dried over MgSO$_4$, and evaporated to a red oil (17.6 g). The crude product was purified over silica gel, which was eluted with 10% to 50% ethyl acetate in cyclohexane, which gave compound 7 (12.0 g, 73% yield). $^1$H NMR (400 MHz, CDCl$_3$) δ 1.65 (d, 3H), 3.96 (s, 3H), 4.74-4.81 (br s, 2H), 6.33 (q, 1H), 6.75 (d, 1H), 7.03 (ddd, 1H), 7.25 (dd, 1H), 7.66 (d, 1H), 8.06 (dd, 1H). LCMS ES m/z 369/371 [M+H]$^+$. A Chiralpak AD-H (4.6× 100 mm, 5 micron) column was eluted with 10% MeOH (0.1% DEA) in CO$_2$ at 120 bar. A flow rate of 5.0 mL/min gave the minor isomer Rt 0.6 minutes and the major isomer Rt 0.8 minutes (99% ee). Optical rotation: [α]$_d^{20}$=−92.4 deg (c=1.5, MeOH).

Preparation of (R)-methyl 2-(1-((N,N-di-Boc-2-amino-5-bromopyridin-3-yl)oxy)ethyl)-4-fluorobenzoic acid (9)

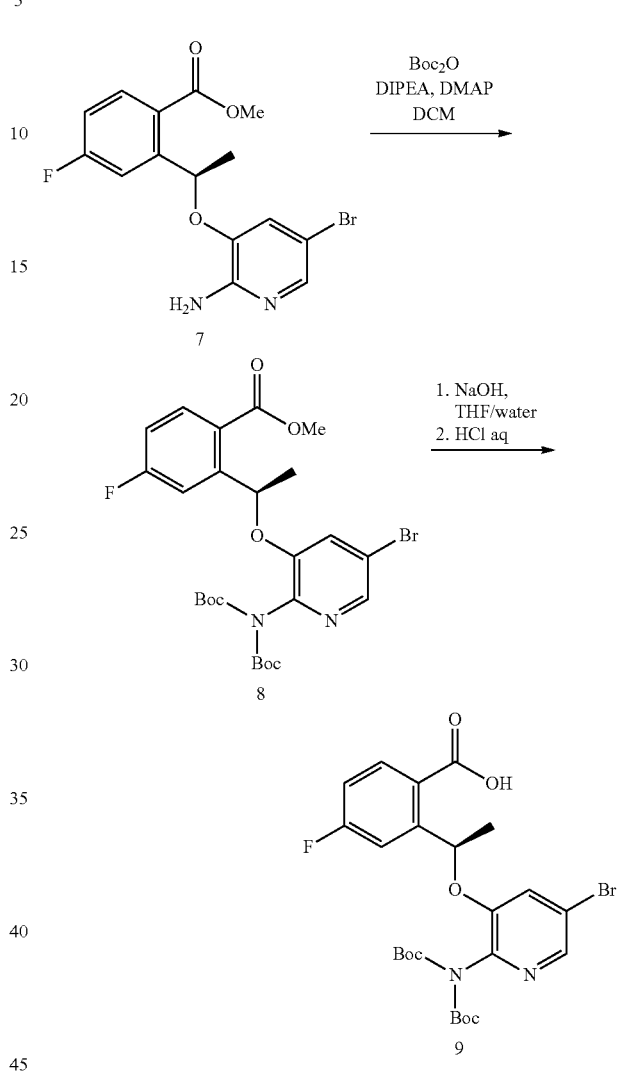

Step 1:

To a solution of compound 7 (2000 g, 5.4 mol) in dry DCM (dichloromethane) (32000 mL) was added DIPEA (N,N-diisopropylethylamine) (2100 g, 16.28 mol) and DMAP (4-dimethylaminopyridine) (132 g, 1.08 mol). Then Boc$_2$O (di-tert-butyl-dicarbonate) (3552 g, 16.28 mol) was added to the mixture in portions. The reaction was stirred at RT for overnight. TLC (petroleum ether/EtOAc=5:1) show the reaction was complete, the mixture was washed with sat. NH$_4$Cl (15 L) two times, then dried over Na$_2$SO$_4$ and concentrated to give a crude product which was purified by column (silica gel, petroleum ether/EtOAc from 20:1 to 10:1) to give compound 8 (2300 g, 75%) as a white solid.

Step 2:

Compound 8 (50 g, 87.81 mmol, 100 mass %) was charged to a round bottom flask (RBF) containing tetrahydrofuran (12.25 mol/L) in Water (5 mL/g, 3060 mmol, 12.25 mol/L) and sodium hydroxide (1 mol/L) in Water (1.5 equiv., 131.7 mmol, 1 mol/L). The biphasic mixture was stirred at RT for 14 hours. 1N HCl was added to adjust pH to <2. THF was then removed by vacuum distillation. The product precipitated out was collected by filtration. The filter cake was rinsed with water, pulled dried then dried in vacuum oven to constant weight (48 h, 55° C., 25 mbar). 48.3 g isolated, 99% yield. ¹H NMR (CDCl₃, 400 MHz) δ 8.24 (1H, dd, 1H, J=5.76 and 3.0 Hz), 8.16 (1H, d, J=2.0 Hz), 7.37 (1H, dd, J=2.5 and 9.8 Hz), 7.19 (1H, d, J=2 Hz), 7.14-7.06 (1H, m), 6.50 (1H, q, J=6.3 Hz), 1.67 (3H, d, J=8.4 Hz), 1.48 (18H, s). ¹³C NMR (CDCl₃, 100 MHz), δ 170.1, 169.2, 167.6, 165.1, 150.6, 149.2, 148.6, 141.4, 140.7, 135.2, 135.1, 124.2, 122.2, 122.1, 119.9, 115.4, 115.1, 113.4, 113.2, 100.0, 83.4, 73.3, 27.9, 23.9. LCMS (M⁺+1) 557.2, 555.3, 457.1, 455.1, 401, 0, 399.0.

Preparation of tert-butyl((4-bromo-5-cyano-1-methyl-1H-pyrazol-3-yl)methyl)(N-methyl)carbamate (15)

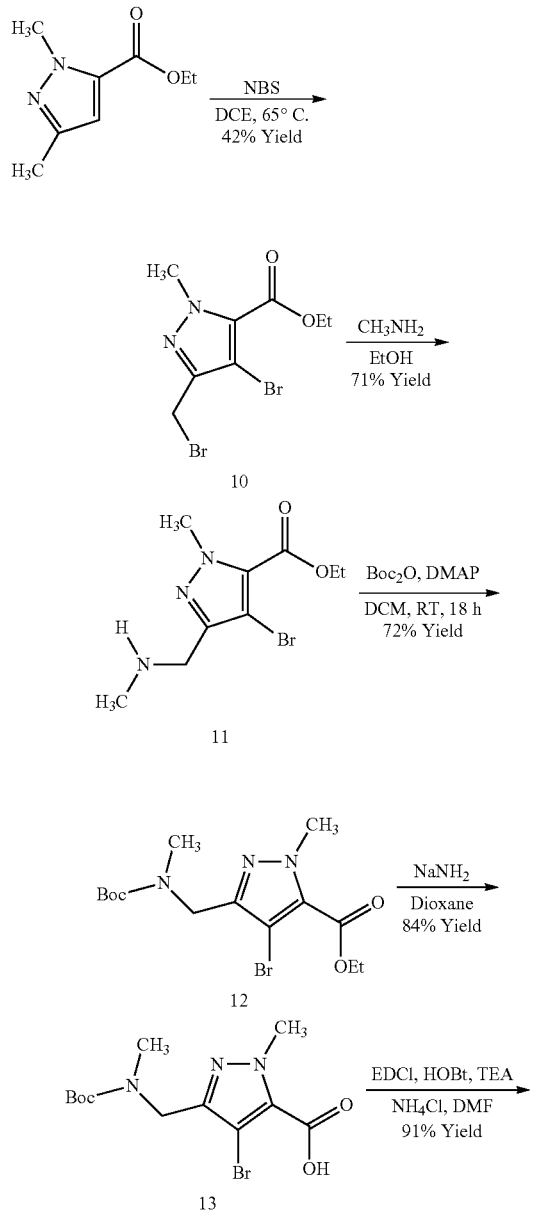

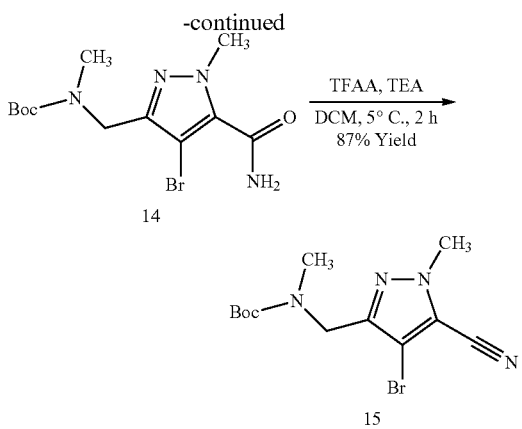

Step 1:
Ethyl 1,3-dimethylpyrazole-5-carboxylate (5.0 g, 30 mmol) was dissolved in 1,2-dichloroethane (200 mL), followed by addition of NBS (5.3 g, 30 mmol) and dibenzoyl peroxide (727 mg, 3.0 mmol), in small portions and stirred at 85° C. for 2 hours. The mixture was allowed to cool, diluted to 400 mL with dichloromethane, and washed with water (2×200 mL). The organic layer was dried over MgSO₄, and evaporated to give compound 10 (4.1 g, 42% yield). TLC (EtOAc/Cyclohexane; 1:10; KMnO₄): Rf~0.3. ¹H NMR (400 MHz, CDCl₃) δ 4.47 (s, 2H), 4.41 (q, 2H), 4.15 (s, 3H), 1.42 (t, 3H). LCMS ES m/z 324/326/328 [M+H]⁺.

Step 2:
Compound 10 (3.0 g, 9.2 mmol) was dissolved in methylamine solution (33% solution in ethanol, 70 mL), and stirred at RT for 16 hours. The mixture was evaporated to give compound 11 (1.8 g, 71% yield). ¹H NMR (400 MHz, CDCl₃) δ 4.39 (q, 2H), 4.14 (s, 3H), 4.05 (s, 2H), 2.62 (d, 3H), 1.41 (t, 3H). LCMS ES m/z 276/278 [M+H]⁺.

Step 3:
Compound 11 (1.8 g, 6.5 mmol) was dissolved in dichloromethane (20 mL), and the mixture cooled to 0° C. A solution of di(tert-butyl)dicarbonate (1.75 g, 8 mmol) in dichloromethane (17.5 mL) was added dropwise. The ice bath was removed and the mixture stirred for 18 hours at room temperature. The mixture was diluted to 100 mL with dichloromethane, and washed with water (2×50 mL). Organic extracts were dried over magnesium sulfate, and evaporated to give compound 12 (1.8 g, 72% yield). ¹H NMR (400 MHz, CDCl₃) δ 4.48-4.44 (m, 2H), 4.41 (q, 2H), 4.12 (s, 3H), 2.82-2.79 (m, 3H), 1.47 (s, 9H), 1.41 (t, 3H). LCMS ES m/z 376/378 [M+H]⁺ and 276/278 [M-BOC]⁺.

Step 4:
Compound 12 (4 g, 11 mmol) was dissolved in dioxane (43 mL). Sodium amide (1 g, 27 mmol) was added in one portion. The reaction mixture was stirred at 100° C. for 24 h. After this time, the solvent was removed under reduced pressure to give a white solid. The material was suspended in EtOAc (100 mL) and washed with 5% citric acid solution (100 mL). The organic phase was separated and washed with water (100 mL), dried over MgSO₄, filtered and the solvent removed in vacuo to give compound 13 as a yellow gum (3.1 g, 84% yield). ¹H NMR (400 MHz, DMSO-d₆) δ 4.27 (s, 2H), 3.92 (s, 3H), 2.70 (s, 3H), 1.40 (s, 9H). LCMS ES m/z 348/350 [M+H]⁺ and 248/250 [M-BOC]+.

Step 5:
Compound 13 (3 g, 8.6 mmol) was dissolved in DMF (43 mL, 0.2 M). HOBt (1.2 g, 8.6 mmol) was added, followed by ammonium chloride (0.9 g, 17.2 mmol). EDCl (2.5 g, 13 mmol) was then added, followed by TEA (2.4 mL, 17 mmol). The reaction mixture was stirred at room temperature. After 18 h, the solvent was removed under reduced pressure to give a yellow oil (8.0 g). The residue was dissolved in EtOAc (75 mL). The organic phase was washed with NaHCO$_3$ (sat. solution, 70 mL) and then brine (100 mL). The combined organic layers were dried over MgSO$_4$ and the solvent removed in vacuo to give compound 14 as a dark yellow oil (2.7 g, 91% yield). This material was used directly in the next step without further purification. $^1$H NMR (400 MHz, CDCl$_3$) δ 6.74 (br s, 1H), 5.95 (br s, 1H), 4.49 (br s, 2H), 4.16 (s, 3H), 2.81 (br s, 3H), 1.47 (s, 9H). LCMS ES m/z 347/349 [M+H]$^+$ and 247/249 [M-BOC]$^+$.

Step 6:

Compound 14 (2.7 g, 7.9 mmol) was dissolved in DCM (80 mL, 0.1 M). TEA (3.3 mL, 23.8 mmol) was then added and the reaction mixture cooled down to −5° C. Trifluoroacetic anhydride (2.2 mL, 15.8 mmol) in DCM (15 mL) was added dropwise over 30 min. After addition, the reaction mixture was stirred at 0° C. for 1 h. After this time, the solvents were removed under reduced pressure to give a dark yellow oil. This residue was diluted in DCM (100 mL), washed with 5% citric acid, sat. NaHCO$_3$ and brine, dried over MgSO$_4$, filtered and the solvents removed in vacuo to give a dark yellow oil (2.6 g). The crude product was purified by reverse phase chromatography to give compound 15 as a yellow oil (2.3 g, 87% yield). $^1$H NMR (400 MHz, CDCl$_3$) δ 4.46 (br s, 2H), 4.01 (s, 3H), 2.83 (br s, 3H), 1.47 (s, 9H). LCMS ES m/z 331/329 [M+H]$^+$ and 229/231 [M-BOC]$^+$ as the base ion.

Preparation of 1-methyl-3-((methylamino)methyl)-1H-pyrazole-5-carbonitrile (21)

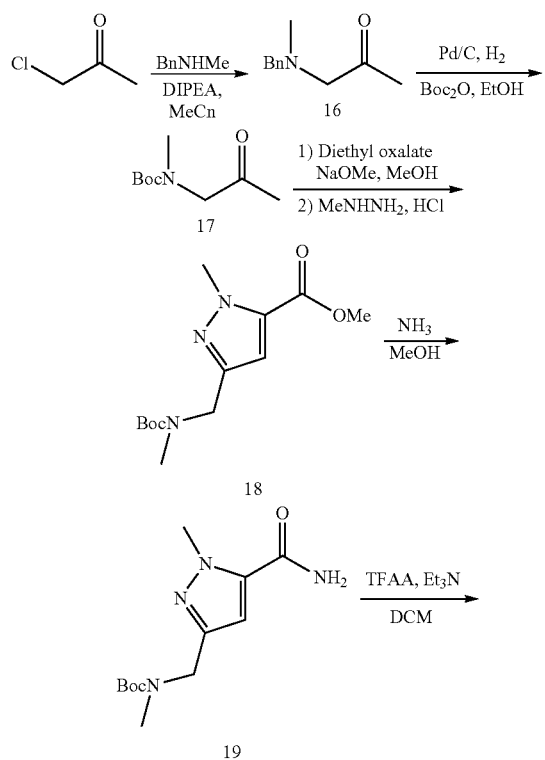

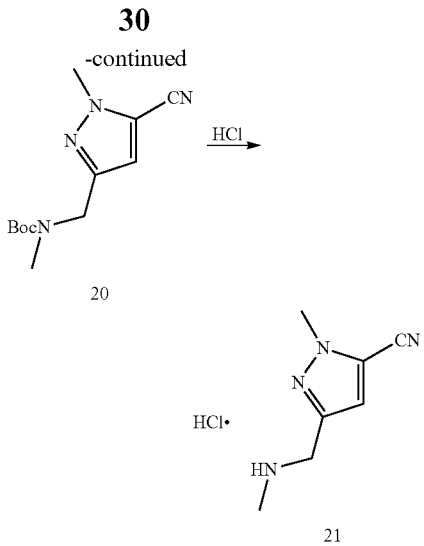

Step 1:

To N-benzylmethylamine (2.40 kg, 19.8 mol) and ethyldiisopropylamine (2.61 kg, 20.2 mol) in acetonitrile (6 L) at 16° C. was added chloroacetone (1.96 kg, 21.2 mol) over 60 mins [exothermic, temp kept <30° C.]. The mixture was stirred at 22° C. for 18 hours then concentrated to an oily solid. The residue was triturated with MTBE (5 L), and then filtered through a pad of CELITE® (600 g, top) and silica (1.5 kg, bottom), washing with MTBE (8 L). The filtrate was evaporated to afford compound 16 (3.35 kg, 18.9 mol, 95%) as a brown oil.

Step 2:

Compound 16 (1.68 kg, 9.45 mol), Boc-anhydride (2.1 kg, 9.6 mol) and 20 wt % Pd/C (50% H$_2$O, 56 g) in ethanol (5 L) were hydrogenated in an 11-L autoclave at 50 psi [exotherm to 40° C. with 20° C. jacket]. The atmosphere became saturated with carbon dioxide during the reaction and so needed to be vented and de-gassed twice to ensure sufficient hydrogen uptake and completion of the reaction. The total reaction time was ~1.5 hours. Two runs (for a total of 18.9 mol) were combined and filtered through a pad of SOLKA-FLOC®, washing with methanol. The filtrate was treated with DMAP (45 g, 0.37 mol) and stirred at room temperature overnight to destroy the excess Boc-anhydride. The mixture was then concentrated to dryness, dissolved in MTBE (6 L) and filtered through a pad of magnesol (1 kg), washing with MTBE (4 L). The filtrate was evaporated to afford compound 17 (3.68 kg, ~95 wt %, 18.7 mol, 99%) as an orange-brown oil.

Step 3:

To compound 17 (3.25 kg, ~95 wt %, 16.5 mol) and diethyl oxalate (4.71 kg, 32.2 mol) in methanol (12 L) at 15° C. was added 25 wt % sodium methoxide in methanol (6.94 kg, 32.1 mol) over 25 mins [temp kept <25° C.]. The mixture was stirred at 20° C. for 16 hours then cooled to −37° C. and 37% hydrochloric acid (3.1 kg, 31 mol) was added over 5 mins [temp kept <−10° C.]. The mixture was cooled to −40° C. and methylhydrazine (1.42 kg, 30.8 mol) was added over 7 mins [temp kept <−17° C.]. The mixture was warmed to 5° C. over 90 minutes, then re-cooled to 0° C. and quenched by addition of 2.4M KHSO$_4$ (6.75 L, 16.2 mol) in one portion [exotherm to 27° C.]. The mixture was diluted with water (25 L) and MTBE (15 L), and the layers separated. The organic layer was washed with brine (7 L) and the aqueous layers then sequentially re-extracted with MTBE (8 L). The combined organics were evaporated and azeotroped with toluene (2 L) to afford crude compound 18. Chromatography (20 kg silica, 10-40% EtOAc in hexane) afforded compound 18 (3.4 kg, ~95 wt %, 11.4 mol, 69%) as an orange oil.

Step 4:

Ammonia (3 kg, 167 mol) was bubbled in to cooled methanol (24 L) [temp kept <18° C.]. A solution of compound 18 (4.8 kg, ~95 wt %, 16.1 mol) in methanol (1.5 L) was added over 30 minutes and the mixture stirred at 25° C. for 68 hours and then at 30° C. for 24 hours. Two runs (from a total of 9.68 kg of ~95 wt % Step 3) were combined and concentrated to ~13 L volume. Water (30 L) was slowly added over 80 minutes, keeping the temperature 30 to 40° C. The resulting slurry was cooled to 20° C., filtered, washed with water (12 L) and pulled dry on the filter overnight. The solids were triturated in MTBE (8 L) and hexane (8 L) at 45° C. then re-cooled to 15° C., filtered, washed with hexane (4 L) and dried under vacuum to afford compound 19 (7.95 kg, 29.6 mol, 90%) as an off-white solid.

Step 5:

To compound 19 (7.0 kg, 26.1 mol) in DCM (30 L) at 0° C. was added triethylamine (5.85 kg, 57.8 mol). The mixture was further cooled to −6° C. then trifluoroacetic anhydride (5.85 kg, 27.8 mol) added over 90 minutes [temp kept 0 to 5° C.]. TLC assay showed the reaction was incomplete. Additional triethylamine (4.1 kg, 40.5 mol) and trifluoroacetic acid (4.1 kg, 19.5 mol) were added over 2 hours until TLC showed complete reaction. The reaction mixture was quenched in to water (40 L) [temp to 23° C.]. The layers were separated and the aqueous re-extracted with DCM (8 L). The organic layers were sequentially washed with brine (7 L), filtered through a pad of silica (3 kg) and eluted with DCM (10 L). The filtrate was evaporated and chromatographed (9 kg silica, eluent 10-30% EtOAc in hexane). Product fractions were evaporated and azeotroped with IPA to afford compound 20 (6.86 kg, ~94 wt %, 25.8 mol, 99%) as an orange oil.

Step 6:

To compound 20 (6.86 kg, ~94 wt %, 25.8 mol) in IPA (35 L) at 17° C. was added 37% hydrochloric acid (6.4 L, 77.4 mol). The mixture was heated to 35° C. overnight then concentrated to a moist solid and residual water azeotroped with additional IPA (8 L). The resulting moist solid was triturated with MTBE (12 L) at 45° C. for 30 minutes then cooled to 20° C. and filtered, washing with MTBE (5 L). The solids were dried under vacuum at 45° C. to afford compound 21 (4.52 kg, 24.2 mol, 94%) as a white solid. $^1$H-NMR was consistent with desired product; mp 203-205° C.; HPLC 99.3%. $^1$H NMR (CD$_3$OD, 400 MHz) δ 7.12 (1H, s), 4.28 (2H, s), 4.09 (3H, s), 2.77 (3H, s). $^{13}$C NMR (CD$_3$OD, 100 MHz) δ 144.5, 177.8, 114.9, 110.9, 45.9, 39.0, 33.2. LCMS (M$^+$+1) 151.1, 138.0, 120.0.

Comparative Example 1A

Preparation of (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetradecine-3-carbonitrile (amorphous)

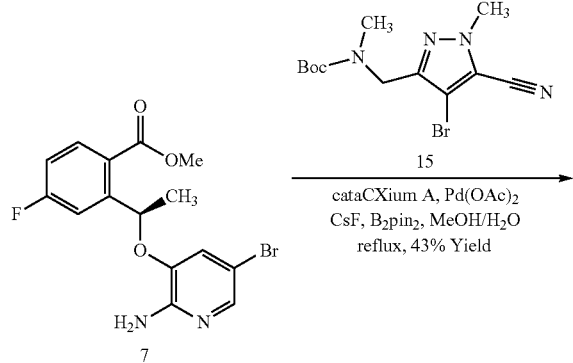

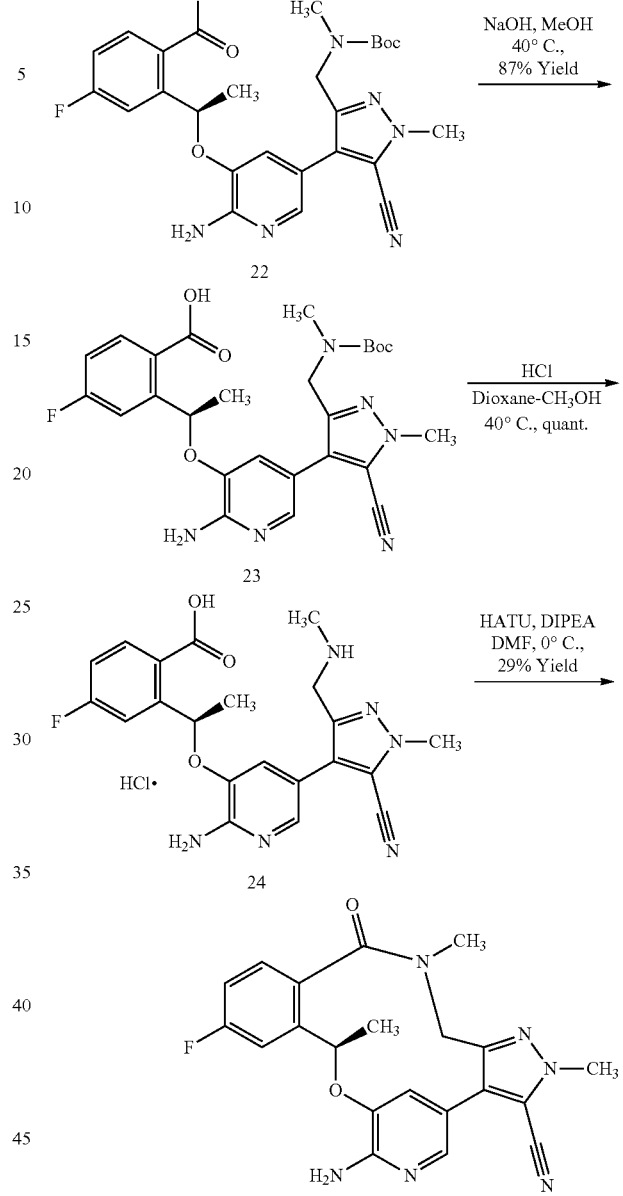

Step 1:

Palladium (II) acetate (53 mg, 0.24 mmol) and CataCXium® A (180 mg, 0.5 mmol) were mixed together in toluene (1.5 mL, de-gassed) and the resulting solution was added via pipette to a stirred solution of compound 7 (0.9 g, 2.4 mmol), compound 15 (1.0 g, 3.0 mmol) bis-pinacolato diboron (0.9 g, 3.6 mmol) and CsF (1.9 g, 12.6 mmol) in MeOH/H$_2$O (9:1, 12 mL, de-gassed) at 60° C. The resulting mixture was then stirred at reflux for 3 hrs. A further portion of Palladium (II) acetate (26 mg, 0.12 mmol) and CataCXium® A (90 mg, 0.25 mmol) in toluene (1.5 mL, de-gassed) was added, and the yellow reaction mixture stirred at 60° C. overnight. After cooling to room temperature, the mixture was diluted with EtOAc (150 mL) and filtered through CELITE®. The filtrate was washed with water (100 mL), then brine (100 mL), dried (Na$_2$SO$_4$) and evaporated. The residue was purified by flash chromatography over silica gel, which was eluted with 1:1 EtOAc/cyclohexane, to give compound 22 as a yellow oil (570 mg, 43% yield). TLC (Rf=0.40, 1:1 EtOAc/cyclohexane). $^1$H NMR (400 MHz, CDCl$_3$) δ 8.03 (m, 1H), 7.65 (s, 1H), 7.27 (dd, 1H, J=9.9, 2.7 Hz), 7.01 (m, 1H), 6.68 (m, 1H), 6.40 (m, 1H), 4.90 (br s, 2H), 4.20-4.30 (m, 2H), 3.96 (s, 3H), 3.94 (s, 3H), 2.55-2.85 (m, 3H), 1.68 (d, 3H, J=6.6 Hz), 1.24 (s, 9H). LCMS ES m/z 539 [M+H]$^+$.

Step 2:

To a solution of compound 22 (69% purity, 0.95 g, assumed 1.05 mmol) in MeOH (20 mL) was added a solution NaOH (1.0 g, 25 mmol) in water (2 mL). The mixture was stirred at 40° C. for 3.5 hours. The reaction was diluted with water (80 mL), concentrated by 20 mL to remove MeOH on the rotary evaporator, and washed with MTBE (100 mL). The aqueous layer was then acidified carefully with 1 M aq HCl to approx. pH 2 (pH paper). Sodium chloride (15 g) was added to the mixture and the mixture was extracted with EtOAc (100 mL). The organic layer was separated, dried (Na$_2$SO$_4$) and evaporated to give compound 23 as a pale yellow solid (480 mg, 87% yield). $^1$H NMR (400 MHz, CD$_3$OD) δ 8.05 (m, 1H), 7.45 (s, 1H), 7.37 (dd, 1H, J=10.4, 2.8 Hz), 7.10 (dt, 1H, J=8.5, 2.4 Hz), 6.50-6.60 (m, 2H), 4.05-4.30 (m, 2H), 3.99 (s, 3H), 2.60-2.80 (m, 3H), 1.72 (d, 3H, J=6.5 Hz). LCMS ES m/z 525 [M+H]$^+$.

Step 3:

A solution of HCl in dioxane (4 M, 6.0 mL) was added to a solution of compound 23 (480 mg, 0.91 mmol) in MeOH (methanol) (6 mL) and the reaction was stirred at 40° C. for 2.5 hours. The reaction mixture was then concentrated to dryness under reduced pressure. The residue was taken-up in MeOH (50 mL) and acetonitrile (100 mL) was added and the mixture was then again evaporated to dryness, to give compound 24 as an off white solid (400 mg, 87% yield). $^1$H NMR (400 MHz, CD$_3$OD) δ 8.07 (dd, 1H, J=8.9. 5.9 Hz), 7.51 (d, 1H, J=1.7 Hz), 7.42 (dd, 1H, J=9.8, 2.6 Hz), 7.23 (d, 1H, J=1.6 Hz), 7.16 (dt, 1H, J=8.5, 2.7 Hz), 6.73 (dd, 1H, J=11.9, 6.9 Hz), 4.22 (d, 1H, J=14.7 Hz), 4.14 (d, 1H, J=14.7 Hz), 4.07 (s, 3H), 2.75 (s, 3H), 1.75 (d, 3H, J=5.5 Hz). LCMS ES m/z 425 [M+H]$^+$.

Step 4:

A solution of compound 24 (400 mg, assumed 0.91 mmol) as the HCl salt and DIPEA (diisopropylethylamine) (1.17 g, 9.1 mmol) in DMF (dimethylformamide) (5.0 mL) and THF (0.5 mL) was added drop-wise to a solution of HATU (2-(1H-7-azabenzotriazol-1-yl)-1,1,3,3-tetramethyl uronium hexafluorophosphate methanaminium) (482 mg, 1.27 mmol) in DMF (10.0 mL) at 0° C. over 30 minutes. After complete addition, the mixture was stirred at 0° C. for a further 30 mins. Water (70 mL) was added and the mixture was extracted into EtOAc (2×60 mL). The combined organics were washed with saturated aqueous NaHCO$_3$ (2×100 mL), brine (100 mL), dried over Na$_2$SO$_4$, and evaporated. The residue was purified by column chromatography over silica gel, which was eluted with 70% EtOAc/cyclohexane giving 205 mg of a pale yellow residue (semi-solid). The solids were dissolved in MTBE (7 mL) and cyclohexane (20 mL) was added slowly with good stirring to precipitate the product. After stirring for 30 minutes, the mixture was filtered, and Example 1A was collected as an amorphous white solid (110 mg, 29% yield). TLC (Rf=0.40, 70% EtOAc in cyclohexane). $^1$H NMR (400 MHz, CDCl$_3$) δ 7.83 (d, 1H, J=2.0 Hz), 7.30 (dd, 1H, J=9.6, 2.4 Hz), 7.21 (dd, 1H, J=8.4, 5.6 Hz), 6.99 (dt, 1H, J=8.0, 2.8 Hz), 6.86 (d, 1H, J=1.2 Hz), 5.75-5.71 (m, 1H), 4.84 (s, 2H), 4.45 (d, 1H, J=14.4 Hz), 4.35 (d, 1H, J=14.4 Hz), 4.07 (s, 3H), 3.13 (s, 3H), 1.79 (d, 3H, J=6.4 Hz). LCMS ES m/z 407 [M+H]$^+$.

Example 1

Preparation of crystalline hydrate of (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetradecine-3-carbonitrile (Form 1)

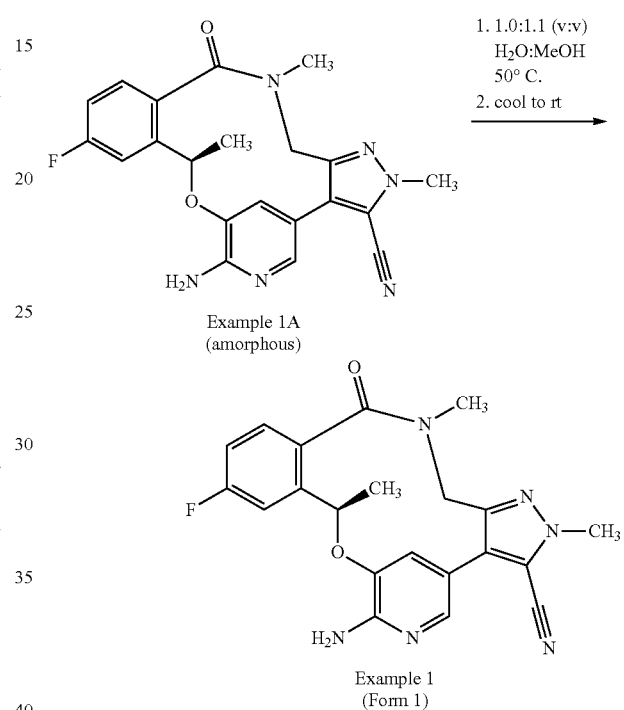

Amorphous (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetradecine-3-carbonitrile free base, prepared as described in Example 1A (and Example 2 of United States Patent Publication No. 2013/0252961), was dissolved in 1.0:1.1 (v:v) H$_2$O:MeOH at a concentration of 22 mg/mL at 50° C., then allowed to cool to room temperature. This slurry was granulated for approximately 72 hours. The solids were isolated by filtration and vacuum dried overnight at 60° C. to produce crystalline hydrate Form 1 of (10R)-7-amino-12-fluoro-2,10,16-trimethyl-15-oxo-10,15,16,17-tetrahydro-2H-8,4-(metheno) pyrazolo[4,3-h][2,5,11]benzoxadiazacyclotetradecine-3-carbonitrile.

Characterization of Crystalline Hydrate Form 1

PXRD Data

FIG. 1 shows PXRD data for the crystalline hydrate Form 1 of (10R)-7-amino-12-fluoro-2,10,16-trimethyl-15-oxo-10, 15,16,17-tetrahydro-2H-8,4-(metheno)pyrazolo[4,3-h][2,5, 11]benzoxadiazacyclotetradecine-3-carbonitrile free base, collected according to General Method 1.

A list of PXRD peaks at diffraction angles 2-Theta ° (°2θ)±0.2 °2θ and their relative intensities is provided in Table 1. Characteristic PXRD peaks distinguishing crystalline hydrate Form 1 from standard excipients are provided in Table 2 °2θ±0.2 °2θ.

TABLE 1

PXRD Peak List for Crystalline Hydrate Form 1 (2-Theta °)

| Angle °2θ ± 0.2 °2θ | Intensity % % |
|---|---|
| 6.7 | 15 |
| 8.4 | 47 |
| 8.9 | 71 |
| 10.4 | 100 |
| 12.3 | 16 |
| 14.3 | 15 |
| 17.9 | 11 |
| 18.3 | 21 |
| 19.9 | 16 |
| 20.9 | 17 |
| 23.5 | 12 |
| 28.6 | 13 |

TABLE 2

Unique PXRD Peak List for Crystalline Hydrate Form 1 (2-Theta °)

| Angle °2θ ± 0.2 °2θ | Intensity % % |
|---|---|
| 8.4 | 47 |
| 8.9 | 71 |
| 10.4 | 100 |

FT-Raman Data

FIG. 4 shows FT-Raman pattern of crystalline Form 1 of (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetradecine-3-carbonitrile, collected according to General Method 2.

A list of FT-Raman peaks (cm$^{-1}$) and qualitative intensities is provided in Table 3 in cm$^{-1}$±2 cm$^{-1}$. Characteristic FT-Raman peaks (cm$^{-1}$) peaks distinguishing crystalline Form 1 from standard excipients are provided in Table 4 in cm$^{-1}$±2 cm$^{-1}$. Normalized peak intensities are indicated as follows: W=weak; M=medium; S=strong.

TABLE 3

FT Raman Peak List for Crystalline Hydrate Form 1 (cm$^{-1}$)

| Wave number cm$^{-1}$ ± 2 cm$^{-1}$ | Normalized peak intensity |
|---|---|
| 119 | S |
| 255 | M |
| 277 | W |
| 287 | W |
| 307 | M |
| 322 | M |
| 380 | W |
| 410 | W |
| 422 | W |
| 443 | W |
| 459 | W |
| 477 | W |
| 490 | W |
| 540 | W |
| 559 | W |
| 571 | W |
| 589 | W |
| 623 | W |
| 638 | W |
| 661 | W |
| 692 | W |
| 703 | W |
| 732 | M |
| 777 | W |
| 805 | W |
| 860 | W |
| 888 | W |
| 906 | W |
| 937 | W |
| 948 | W |
| 972 | W |
| 1070 | W |
| 1142 | W |
| 1203 | W |
| 1218 | W |
| 1236 | W |
| 1261 | W |
| 1301 | M |
| 1332 | W |
| 1353 | W |
| 1367 | M |
| 1420 | M |
| 1443 | M |
| 1554 | S |
| 1624 | M |
| 2228 | M |
| 2945 | W |
| 2995 | W |
| 3063 | W |
| 3335 | W |

TABLE 4

Unique FT Raman Peak List for Crystalline Hydrate Form 1 (cm$^{-1}$)

| Wave number cm$^{-1}$ ± 2 cm$^{-1}$ | Normalized peak intensity |
|---|---|
| 703 | W |
| 777 | W |
| 805 | W |
| 1554 | S |
| 2228 | M |
| 3063 | W | ssNMR Data

FIG. 7 shows the carbon CPMAS spectrum of crystalline Form 1 of (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetradecine-3-carbonitrile, which was collected according to General Method 3. Chemical shifts are expressed in parts per million (ppm) and are referenced to external sample of solid phase adamantane at 29.5 ppm.

A list of ssNMR $^{13}$C chemical shifts (ppm) for crystalline Form 1 is provided in Table 5 in ppm±0.2 ppm. Characteristic ssNMR $^{13}$C chemical shifts (ppm) distinguishing crystalline Form 1 from standard excipients are provided in Table 6 in ppm±0.2 ppm.

TABLE 5 ssNMR $^{13}$C Chemical Shifts for Crystalline Hydrate Form 1 (ppm)

$^{13}$C Chemical Shifts [ppm ± 0.2 ppm]

| |
|---|
| 22.1 |
| 23.8 |

TABLE 5-continued ssNMR $^{13}$C Chemical Shifts for Crystalline Hydrate Form 1 (ppm)
$^{13}$C Chemical Shifts
[ppm ± 0.2 ppm]

| |
|---|
| 24.4 |
| 25.1 |
| 29.9 |
| 31.3 |
| 32.0 |
| 37.9 |
| 47.3 |
| 48.4 |
| 72.3 |
| 111.2 |
| 113.6 |
| 115.5 |
| 117.7 |
| 119.4 |
| 126.0 |
| 128.4 |
| 130.2 |
| 131.4 |
| 132.4 |
| 133.6 |
| 135.1 |
| 136.2 |
| 138.0 |
| 138.7 |
| 141.8 |
| 143.1 |
| 144.1 |
| 150.6 |
| 162.8 |
| 163.9 |
| 164.5 |
| 169.6 |

TABLE 6

Unique ssNMR $^{13}$C Chemical Shifts for Crystalline Hydrate Form 1 (ppm)
$^{13}$C Chemical Shifts
[ppm ± 0.2 ppm]

| |
|---|
| 47.3 |
| 113.6 |
| 133.6 |

FIG. 10 shows the fluorine MAS (ssNMR) spectrum of crystalline Form 1 of (10R)-7-amino-12-fluoro-2,10,16-trimethyl-15-oxo-10,15,16,17-tetrahydro-2H-8,4-(metheno)pyrazolo-[4,3-h][2,5,11]benzoxadiazacyclotetradecine-3-carbonitrile, collected according to General Method 3. Chemical shifts are expressed in parts per million (ppm) and are referenced to an external sample of trifluoroacetic acid (50% V/V in H$_2$O) at −76.54 ppm.

The ssNMR $^{19}$F chemical shift (ppm) for crystalline Form 1 is provided in Table 7 in ppm±0.2 ppm. The characteristic ssNMR $^{19}$F chemical shifts (ppm) distinguishing crystalline Form 1 from standard excipients are provided in Table 8 in ppm±0.2 ppm.

TABLE 7 ssNMR $^{19}$F Chemical Shifts for Crystalline Hydrate Form 1 (ppm)
$^{19}$F Chemical Shifts
[ppm ± 0.2 ppm]

| |
|---|
| −122.5 |
| −116.4 |
| −109.2 |
| −107.2 |
| −103.1 |

TABLE 8

Unique ssNMR $^{19}$F Chemical Shifts for Crystalline Hydrate Form 1 (ppm)
$^{19}$F Chemical Shifts
[ppm ± 0.2 ppm]

| |
|---|
| −116.4 |
| −109.2 |

Example 2

Preparation of crystalline hydrate of (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetradecine-3-carbonitrile (Form 2)

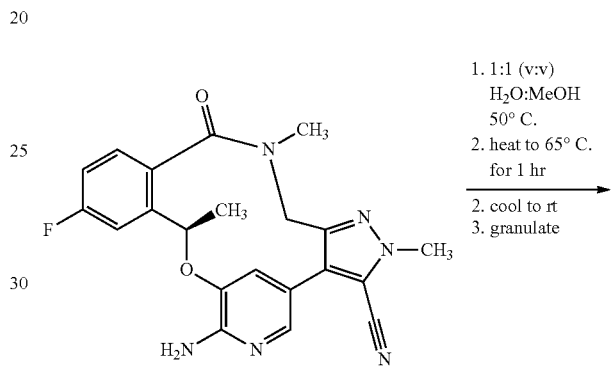

Example 1A
(amorphous)

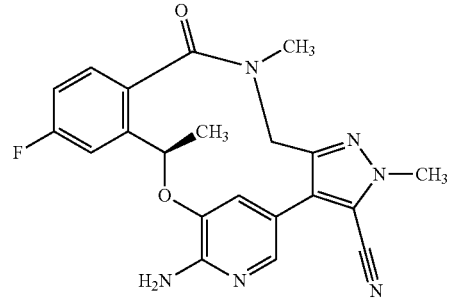

Example 2
(Form 2)

Amorphous (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetradecine-3-carbonitrile free base prepared as described in Example 1A, was dissolved in 1:1 (v:v) H$_2$O:MeOH at a concentration of 25 mg/mL, heated to 65° C. for 1 hr, then allowed to cool to room temperature, resulting in a slurry after 2 hrs with gentle stirring. This slurry was granulated for approximately 72 hrs. The solids were isolated by filtration and vacuum dried at room temperature for 4 hrs to produce the crystalline hydrate Form 2 of (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetradecine-3-carbonitrile. The crystalline material was isolated as a hydrate containing a non-stoichiometric amount of methanol.

Characterization of Crystalline Hydrate Form 2

PXRD Data

FIG. 2 shows PXRD data for the crystalline hydrate Form 2 of (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetradecine-3-carbonitrile free base, collected according to General Method 1.

A list of PXRD peaks at diffraction angles 2-Theta ° (°2θ)±0.2 °2θ and their relative intensities is provided in Table 9. Characteristic PXRD peaks distinguishing crystalline hydrate Form 1 from standard excipients are provided in Table 11 °2θ±0.2 °2θ.

TABLE 9

PXRD Peak List for Crystalline Hydrate Form 2 (2-Theta °)

| Angle °2θ ± 0.2 °2θ | Intensity % % |
|---|---|
| 5.1 | 27 |
| 5.6 | 43 |
| 6.2 | 15 |
| 7.6 | 100 |
| 9.5 | 63 |
| 10.2 | 73 |
| 11.5 | 15 |
| 11.7 | 28 |
| 12.4 | 18 |
| 12.6 | 18 |
| 13.6 | 66 |
| 13.9 | 27 |
| 15.4 | 17 |
| 15.6 | 12 |
| 16.9 | 20 |
| 17.1 | 36 |
| 17.7 | 20 |
| 18.6 | 35 |
| 18.8 | 35 |
| 19.3 | 18 |
| 19.8 | 14 |
| 20.6 | 10 |
| 21.3 | 47 |
| 22.8 | 43 |
| 23.6 | 20 |
| 23.9 | 23 |
| 24.7 | 13 |
| 24.9 | 19 |
| 25.2 | 11 |
| 29.0 | 19 |

TABLE 10

Unique PXRD Peak List for Crystalline Hydrate Form 2 (2-Theta °)

| Angle °2θ ± 0.2 °2θ | Intensity % % |
|---|---|
| 5.6 | 43 |
| 7.6 | 100 |
| 9.5 | 63 |
| 10.2 | 73 |
| 13.6 | 66 |

FT-Raman Data

FIG. 5 shows FT-Raman pattern of crystalline Form 2 of (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetradecine-3-carbonitrile, collected according to General Method 2.

A list of FT-Raman peaks ($cm^{-1}$) and qualitative intensities is provided in Table 11 in $cm^{-1}$±2 $cm^{-1}$. Characteristic FT-Raman peaks ($cm^{-1}$) peaks distinguishing crystalline Form 2 from standard excipients are provided in Table 12 in $cm^{-1}$±2 $cm^{-1}$. Normalized peak intensities are indicated as follows: W=weak; M=medium; S=strong.

TABLE 11

FT Raman Peak list for Crystalline Hydrate Form 2 ($cm^{-1}$)

| Wave number $cm^{-1}$ ± 2 $cm^{-1}$ | Normalized peak intensity |
|---|---|
| 120 | S |
| 142 | M |
| 219 | W |
| 240 | W |
| 253 | M |
| 278 | W |
| 287 | W |
| 309 | M |
| 321 | M |
| 366 | W |
| 378 | W |
| 410 | W |
| 422 | W |
| 444 | W |
| 457 | W |
| 474 | W |
| 491 | W |
| 537 | W |
| 560 | W |
| 572 | W |
| 589 | W |
| 600 | W |
| 624 | W |
| 637 | W |
| 661 | W |
| 692 | W |
| 705 | W |
| 731 | W |
| 764 | W |
| 777 | W |
| 804 | W |
| 859 | W |
| 887 | W |
| 906 | W |
| 936 | W |
| 948 | W |
| 973 | W |
| 1052 | W |
| 1141 | W |
| 1157 | W |
| 1203 | W |
| 1218 | W |
| 1235 | W |
| 1259 | W |
| 1299 | M |
| 1331 | W |
| 1354 | W |
| 1368 | M |
| 1419 | M |
| 1443 | M |
| 1493 | W |
| 1553 | S |
| 1611 | M |
| 1623 | S |
| 2229 | M |
| 2926 | W |
| 2944 | M |
| 2991 | W |
| 3004 | W |
| 3061 | W |
| 3215 | W |
| 3325 | W |

TABLE 12

Unique FT Raman Peak list for Crystalline Hydrate Form 2 (cm$^{-1}$)

| Wave number cm$^{-1}$ ± 2 cm$^{-1}$ | Normalized peak intensity |
|---|---|
| 705 | W |
| 731 | W |
| 777 | W |
| 804 | W |
| 1611 | M |
| 2229 | M |
| 3061 | W | ss-NMR Data

FIG. 8 shows the carbon CPMAS spectrum of crystalline Form 2 of (10R)-7-amino-12-fluoro-2,10,16-trimethyl-15-oxo-10,15,16,17-tetrahydro-2H-8,4-(metheno)pyrazolo-[4,3-h][2,5,11]benzoxadiazacyclotetradecine-3-carbonitrile, which was collected according to General Method 3. Chemical shifts are expressed in parts per million (ppm) and are referenced to external sample of solid phase adamantane at 29.5 ppm.

A list of ssNMR $^{13}$C chemical shifts (ppm) for crystalline Form 2 is provided in Table 13 in ppm±0.2 ppm. Characteristic ssNMR $^{13}$C chemical shifts (ppm) distinguishing crystalline Form 2 from standard excipients are provided in Table 14 in ppm±0.2 ppm.

TABLE 13 ssNMR $^{13}$C Chemical Shifts for Crystalline Hydrate Form 2 (ppm)
$^{13}$C Chemical Shifts
[ppm ± 0.2 ppm]

| |
|---|
| 22.7 |
| 24.2 |
| 24.6 |
| 26.2 |
| 30.2 |
| 31.1 |
| 32.4 |
| 32.9 |
| 36.3 |
| 37.0 |
| 38.6 |
| 39.4 |
| 45.9 |
| 47.9 |
| 48.3 |
| 71.7 |
| 72.6 |
| 110.9 |
| 112.6 |
| 114.1 |
| 114.6 |
| 117.2 |
| 118.0 |
| 118.9 |
| 125.4 |
| 126.1 |
| 126.7 |
| 128.3 |
| 129.9 |
| 131.0 |
| 133.0 |
| 134.4 |
| 135.2 |
| 136.8 |
| 138.8 |
| 139.5 |
| 141.6 |
| 142.4 |
| 143.0 |
| 143.8 |
| 144.9 |

TABLE 13-continued ssNMR $^{13}$C Chemical Shifts for Crystalline Hydrate Form 2 (ppm)
$^{13}$C Chemical Shifts
[ppm ± 0.2 ppm]

| |
|---|
| 145.5 |
| 150.4 |
| 162.6 |
| 163.8 |
| 165.8 |
| 168.2 |
| 169.7 |

TABLE 14

Unique ssNMR $^{13}$C Chemical Shifts for Crystalline Hydrate Form 2 (ppm)
$^{13}$C Chemical Shifts
[ppm ± 0.2 ppm]

| |
|---|
| 48.3 |
| 118.9 |
| 168.2 |

FIG. 11 shows the fluorine MAS (ssNMR) spectrum of crystalline Form 2 of (10R)-7-amino-12-fluoro-2,10,16-trimethyl-15-oxo-10,15,16,17-tetrahydro-2H-8,4-(metheno)pyrazolo-[4,3-h][2,5,11]benzoxadiazacyclotetradecine-3-carbonitrile, collected according to General Method 3. Chemical shifts are expressed in parts per million (ppm) and are referenced to an external sample of trifluoroacetic acid (50% V/V in H$_2$O) at −76.54 ppm.

The ssNMR $^{19}$F chemical shift (ppm) for crystalline Form 2 is provided in Table 15 in ppm±0.2 ppm. The characteristic ssNMR $^{19}$F chemical shifts (ppm) distinguishing crystalline Form 2 from standard excipients are provided in Table 16 in ppm±0.2 ppm.

TABLE 15 ssNMR $^{19}$F Chemical Shifts for Crystalline Hydrate Form 2 (ppm)
$^{19}$F Chemical Shifts
[ppm ± 0.2 ppm]

| |
|---|
| −112.4 |
| −110.0 |
| −108.3 |

TABLE 16

Unique ssNMR $^{19}$F Chemical Shifts for Crystalline Hydrate Form 2 (ppm)
$^{19}$F Chemical Shifts
[ppm ± 0.2 ppm]

| |
|---|
| −108.3 |

Example 3

Preparation of crystalline acetic acid solvate of (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetradecine-3-carbonitrile (Form 3)

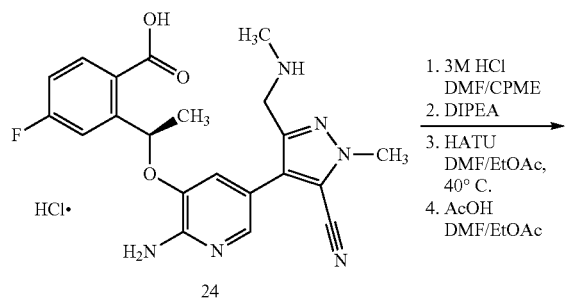

24

1. 3M HCl DMF/CPME
2. DIPEA
3. HATU DMF/EtOAc, 40° C.
4. AcOH DMF/EtOAc

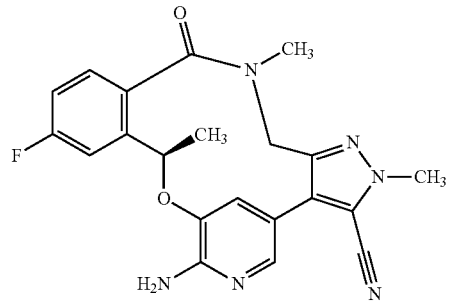

Example 3
(Form 3)

A solution of (R)-2-(1-((2-amino-5-(5-cyano-1-methyl-3-((methylamino)-methyl)-1H-pyrazol-4-yl)pyridin-3-yl)oxy)ethyl)-4-fluorobenzoic acid hydrochloride (compound 24) (10 g, 21.6 mmol), prepared as described in step 3 of Example 1A, in dimethylformamide (50 mL) was treated with 3 M HCl solution in cyclopentyl methyl ether (CPME) (8.65 mL, 25.95 mmol). After stirring for 5 min, diisopropylethylamine (11.31 mL, 64.8 mmol) was added. The resulting mixture was then slowly (over a period of 12-16 h) transferred to another flask containing HATU (12.33 g, 32.4 mmol) in a solvent mixture of DMF (50 mL) and EtOAc (50 mL) at 40° C. Water (200 mL) was added, followed by addition of 1 M $Na_2CO_3$ aqueous solution (50 mL). After separating the layers, the aqueous phase was extracted with EtOAc (100 mL). The combined organic phase was successively washed with 1 M $Na_2CO_3$ aqueous solution (50 mL) and saturated NaCl aqueous solution (50 mL). The organic solution was then concentrated under reduced pressure to approximately 100 mL in volume and confirmed the water content at 0.1% or lower using standard techniques. The resulting mixture was filtered to render a particle free solution. The filtrate was further concentrated under reduced pressure to approximately 30 mL in volume.

Acetic acid (1.95 g, 32.4 mmol) was added, the resulting mixture was stirred for 3 h. The product was collected by filtration and the filter cake rinsed with n-heptane. Upon drying (40° C., 50 mmHg) to constant weight, the product of Example 3 was isolated as an off-white crystalline solid (4.35 g, 43% yield). The crystalline material was isolated as an acetic acid solvate containing about 1 molecule of acetic acid per one molecule of (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetradecine-3-carbonitrile as determined by solution NMR spectroscopy.

Characterization of Crystalline Acetic Acid Solvate Form 3

PXRD Data

FIG. 3 shows PXRD data for the crystalline Form 3 (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetradecine-3-carbonitrile (free base), collected according to General Method 1.

A list of PXRD peaks at diffraction angles 2-Theta ° (°2θ)±0.2 °2θ and their relative intensities is provided in Table 17. Characteristic PXRD peaks distinguishing crystalline Form 3 from standard excipients are provided in Table 18 °2θ±0.2 °2θ.

TABLE 17

PXRD Peak list for Crystalline Acetic Acid Solvate Form 3 (2-Theta °)

| Angle °2θ ± 0.2 °2θ | Intensity % |
|---|---|
| 10.5 | 17 |
| 11.4 | 20 |
| 12.9 | 53 |
| 14.5 | 30 |
| 15.3 | 17 |
| 17.2 | 15 |
| 17.9 | 36 |
| 18.3 | 17 |
| 20.0 | 16 |
| 21.1 | 32 |
| 22.5 | 37 |
| 23.1 | 100 |
| 23.4 | 14 |
| 23.8 | 13 |
| 25.9 | 52 |
| 26.2 | 15 |
| 27.0 | 18 |
| 27.2 | 16 |
| 29.3 | 13 |
| 30.2 | 15 |
| 30.3 | 12 |

TABLE 18

Unique PXRD peaks for Crystalline Acetic Acid Solvate Form 3 (2-Theta °)

| Angle °2θ ± 0.2 °2θ | Intensity % |
|---|---|
| 10.5 | 17 |
| 11.4 | 20 |
| 12.9 | 53 |
| 14.5 | 30 |
| 15.3 | 17 |

FT-Raman Data

FIG. 6 shows FT-Raman pattern of crystalline Form 3 of (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetradecine-3-carbonitrile, collected according to General Method 2.

A list of FT-Raman peaks (cm$^{-1}$) and qualitative intensities is provided in Table 19 in cm$^{-1}$±2 cm$^{-1}$. Characteristic FT-Raman peaks (cm$^{-1}$) peaks distinguishing crystalline Form 3 from standard excipients are provided in Table 20 in cm$^{-1}$±2 cm$^{-1}$. A list of unique and highly characteristic FT-Raman peaks (cm$^{-1}$) distinguishing crystalline Form 3 are provided in Table 21 in cm$^{-1}$±2 cm$^{-1}$. Normalized peak intensities are indicated as follows: W=weak; M=medium; S=strong.

TABLE 19

FT Raman Peak list for Crystalline Acetic Acid Solvate Form 3 (cm$^{-1}$)

| Wave number cm$^{-1}$ ± 2 cm$^{-1}$ | Normalized peak intensity |
|---|---|
| 113 | M |
| 130 | M |
| 158 | M |
| 185 | W |
| 198 | W |
| 253 | W |
| 262 | W |
| 290 | W |
| 310 | W |
| 321 | W |
| 362 | W |
| 383 | W |
| 420 | W |
| 442 | W |
| 450 | W |
| 478 | W |
| 492 | W |
| 560 | W |
| 574 | W |
| 594 | W |
| 622 | W |
| 632 | W |
| 646 | W |
| 668 | W |
| 695 | W |
| 708 | W |
| 733 | W |
| 763 | W |
| 774 | W |
| 809 | W |
| 862 | W |
| 888 | W |
| 910 | W |
| 936 | W |
| 950 | W |
| 977 | W |
| 1046 | W |
| 1071 | W |
| 1087 | W |
| 1142 | W |
| 1157 | W |
| 1211 | W |
| 1249 | W |
| 1265 | W |
| 1305 | W |
| 1325 | M |
| 1345 | W |
| 1351 | W |
| 1369 | M |
| 1395 | W |
| 1423 | M |
| 1444 | M |
| 1511 | W |
| 1552 | S |
| 1573 | W |
| 1587 | W |
| 1613 | M |
| 1643 | M |
| 2181 | W |
| 2234 | S |
| 2923 | W |
| 2942 | W |
| 2994 | W |
| 3011 | W |
| 3055 | W |
| 3194 | W |

TABLE 20

Unique FT Raman Peak list for Crystalline Acetic Acid Solvate Form 3 (cm$^{-1}$)

| Wave number cm$^{-1}$ ± 2 cm$^{-1}$ | Normalized peak intensity |
|---|---|
| 3055 | W |
| 2234 | S |
| 1613 | M |
| 1643 | M |
| 1552 | S |
| 1573 | W |
| 733 | W |
| 774 | W |
| 809 | W |

TABLE 21

Unique & highly characteristic FT- Raman Peak list for Crystalline Acetic Acid Solvate Form 3 (cm$^{-1}$)

| Wave number cm$^{-1}$ ± 2 cm$^{-1}$ | Normalized peak intensity |
|---|---|
| 2234 | S |
| 1613 | M |
| 1643 | M |
| 1552 | S | ss-NMR Data

FIG. 9 shows the carbon CPMAS spectrum of crystalline Form 3 of (10R)-7-amino-12-fluoro-2,10,16-trimethyl-15-oxo-10,15,16,17-tetrahydro-2H-8,4-(metheno)pyrazolo-[4,3-h][2,5,11]benzoxadiazacyclotetradecine-3-carbonitrile, which was collected according to General Method 3. Chemical shifts are expressed in parts per million (ppm) and are referenced to an external sample of solid phase adamantane at 29.5 ppm.

A list of ssNMR $^{13}$C chemical shifts (ppm) for crystalline Form 3 is provided in Table 22 in ppm±0.2 ppm. Characteristic ssNMR $^{13}$C chemical shifts (ppm) distinguishing crystalline Form 3 from standard excipients are provided in Table 23 in ppm±0.2 ppm.

TABLE 22 ssNMR $^{13}$C chemical shifts for Crystalline Acetic Acid Solvate Form 3 (ppm)
$^{13}$C Chemical Shifts
[ppm ± 0.2 ppm]

| |
|---|
| 21.1 |
| 22.8 |
| 33.0 |
| 37.4 |
| 49.9 |
| 73.1 |
| 110.9 |
| 111.7 |
| 115.2 |
| 115.9 |
| 117.0 |
| 126.3 |
| 128.6 |
| 131.1 |
| 131.8 |
| 140.7 |
| 142.9 |
| 144.1 |
| 151.3 |
| 163.8 |
| 165.9 |
| 170.3 |
| 175.0 |

TABLE 23

Unique ssNMR $^{13}$C chemical shifts for Crystalline
Acetic Acid Solvate Form 3 (ppm)

| $^{13}$C Chemical Shifts [ppm ± 0.2 ppm] |
|---|
| 22.8 |
| 140.7 |
| 170.3 |

FIG. 12 shows the fluorine MAS (ssNMR) spectrum of crystalline Form 3 of (10R)-7-amino-12-fluoro-2,10,16-trimethyl-15-oxo-10,15,16,17-tetrahydro-2H-8,4-(metheno)pyrazolo-[4,3-h][2,5,11]benzoxadiazacyclotetradecine-3-carbonitrile, collected according to General Method 3. Chemical shifts are expressed in parts per million (ppm) and are referenced to an external sample of trifluoroacetic acid (50% V/V in H$_2$O) at −76.54 ppm.

The ssNMR $^{19}$F chemical shift (ppm) for crystalline Form 3 is provided in Table 24 in ppm±0.2 ppm. This peak distinguishes crystalline Form 3 from standard excipients.

TABLE 24

Unique ssNMR $^{19}$F chemical shifts for Crystalline Acetic Acid Solvate Form 3 (ppm)

| $^{19}$F Chemical Shifts [ppm ± 0.2 ppm] |
|---|
| −107.2 |

Example 4

Alternative preparation of crystalline acetic acid solvate of (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetradecine-3-carbonitrile (Form 3)

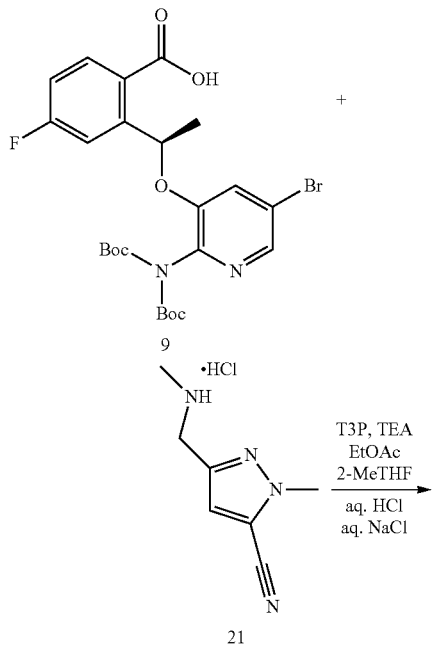

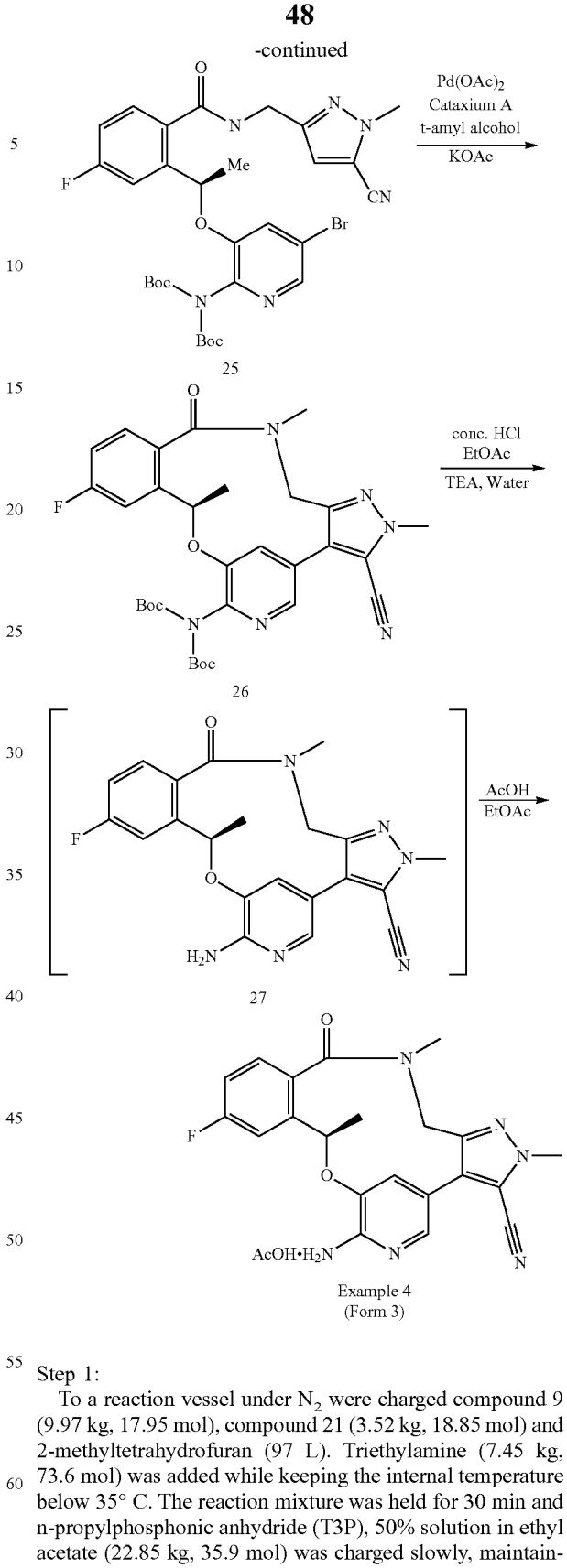

Example 4
(Form 3)

Step 1:

To a reaction vessel under N$_2$ were charged compound 9 (9.97 kg, 17.95 mol), compound 21 (3.52 kg, 18.85 mol) and 2-methyltetrahydrofuran (97 L). Triethylamine (7.45 kg, 73.6 mol) was added while keeping the internal temperature below 35° C. The reaction mixture was held for 30 min and n-propylphosphonic anhydride (T3P), 50% solution in ethyl acetate (22.85 kg, 35.9 mol) was charged slowly, maintaining the internal temperature below 25° C. The reaction mixture was held at 20° C. for at least 2 h until reaction was deemed complete. Ethyl acetate (35 L) and water (66 L) were added followed by 0.5N Hydrochloric acid solution (80 L). The aqueous layer was removed and the organic layer was washed with brine solution (80 L). The organic layer was concentrated and solvent exchanged with 2-methyl-2-butanol (80 L) give compound 25 (23 wt/wt %) solution in 2-methyl-2-butanol. This solution was carried forward to the next step directly in three batches, assuming 12.00 kg (100% yield) from this step.

Step 2:

2-Methyl-2-butanol (100 L) was combined with potassium acetate (1.8 kg, 18.34 mol), palladium(II) acetate (0.10 kg, 0.46 mol) and water (0.10 kg, 5.73 mol). The resulting mixture was purged with nitrogen. Di(1-adamantyl)n-butylphosphine (0.23 kg, 0.43 mol) was added. An amount of 20% of compound 25 (3.97 kg active or 17.3 L of step 1 solution in 2-methyl-2-butanol) was added, and the resulting reaction mixture was heated at reflux for 2 h. The remaining solution of compound 25 in 2-methyl-2-butanol was subsequently added to the reaction over a period of 5 h. The resulting mixture was heated until the reaction was deemed complete (typically 16-20 h). This reaction step was processed in three batches, and the isolation was done in one single batch. Thus, the combined three batches were filtered through CELITE® to remove insoluble materials. The filtrate was concentrated to a low volume (approximately 20 L). Acetonitrile (60 L) was added. The resulting mixture was heated to reflux for 2-4 h, then cooled to RT for granulation. The resulting slurry was filtered to give compound 26 as a crude product. The crude product was combined with ethyl acetate (80 L) and Silicycle thiol (5 kg). The resulting mixture was heated for 2 h, cooled to RT and filtered. The filtrate was concentrated to approx. 20 L, and the resulting slurry was granulated and filtered. The filter cake was rinsed with ethyl acetate (4 L) and dried in a vacuum oven to give compound 26 as a pure product (4.74 kg, 43.5% overall last two steps). $^1$H NMR (CDCl$_3$) δ 8.25-8.23 (m, 1H), 7.28 (1H, dd, 2.76 and 9.79 Hz), 7.22 (1H, dd, 5.52 and 8.53 Hz), 7.18 (1H, d, J=1.76 Hz), 7.01 (1H, dt, J=2.50 and 8.03 Hz), 5.78-5.70 (m, 1H), 4.76 (1H, d, J=14.3 Hz), 4.13 (s, 3H), 3.16 (s, 3H), 1.78 (d, 3H, J=6.02 Hz), 1.45 (s, 18H); 13C NMR (CDCl$_3$) δ 167.0, 162.9, 160.4, 148.7, 146.3, 143.0, 140.7, 139.9, 135.5, 129.9, 129.8, 126.1, 123.8, 123.5, 119.7, 113.8, 113.5, 111.6, 108.1, 81.1, 70.1, 45.5, 37.0, 29.7, 26.0, 20.7; LCMS (M+1)$^+$607.3, 507.1, 451.2.

Step 3:

To a rector under N$_2$ was added compound 26 (4.74 kg, 7.82 mol) and ethyl acetate (54 L). Hydrochloric acid 37% (5.19 L, 63.2 mol) was charged slowly while keeping the internal temperature below 25° C. The reaction mixture was stirred for 24-48 h until the reaction was complete. Ethyl acetate (54 L) and water (54 L) were added. The reaction mixture was then treated with triethylamine until pH 8-9 was reached. The aqueous layer was removed and then the organic layer was washed water (2×54 L). The organic layer was concentrated under reduced pressure to approx. 54 L to give compound 27 (unisolated).

Step 4:

Acetic acid (1.0 kg, 16.6 mol) was added to the organic layer containing compound 27. The reaction mixture was concentrated and then held for at least 3 h with stirring at RT. The resulted slurry was filtered. The filter cake was washed with ethyl acetate (2 L) and dried under vacuum to give 3.20 kg (87.8% yield) of Example 4 acetic acid solvate (Form 3). The spectroscopic data of this material was identical to that of an authentic sample of the crystalline acetic acid Form 3 of (10R)-7-amino-12-fluoro-2,10,16-trimethyl-15-oxo-10, 15,16,17-tetrahydro-2H-8,4-(metheno)pyrazolo[4,3-h][2,5, 11]-benzoxadiazacyclotetradecine-3-carbonitrile prepared according to Example 3.

Example 5

Representative drug product formulation comprising crystalline acetic acid solvate of (10R)-7-amino-12-fluoro-2,10,16-trimethyl-15-oxo-10,15,16, 17-tetrahydro-2H-8,4-(metheno)pyrazolo[4,3-h][2,5, 11]-benzoxadiazacyclotetradecine-3-carbonitrile (Form 3)

Immediate release (IR) tablets comprising a crystalline solvate of (10R)-7-amino-12-fluoro-2,10,16-trimethyl-15-oxo-10,15,16,17-tetrahydro-2H-8,4-(metheno)pyrazolo[4, 3-h][2,5,11]-benzoxadiazacyclotetradecine-3-carbonitrile may be prepared using conventional excipients commonly used in tableted formulations.

Tablets typically contain from 1-30% of (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetradecine-3-carbonitrile on a w/w basis. Microcrystalline cellulose and dibasic calcium phosphate may be used as tablet fillers, and sodium starch glycolate may be used as a disintegrant. Magnesium stearate may be used as a lubricant and can be incorporated into the tablet or added externally during compression.

A typical immediate release formulation of crystalline acetic acid solvate of (10R)-7-amino-12-fluoro-2,10,16-trimethyl-15-oxo-10,15,16,17-tetrahydro-2H-8,4-(metheno) pyrazolo[4,3-h][2,5,11]-benzoxadiazacyclotetradecine-3-carbonitrile (Form 3) is provided in Table 26. The compound of Formula I can also be formulated using lactose as a tablet filler, and croscarmellose sodium as a disintegrant. Comparable compositions may be prepared using the hydrates Form 1 and the hydrate Form 2.

TABLE 25

Typical Composition of IR Tablet

| | | % composition |
| --- | --- | --- |
| compound of Formula I | Active Ingredient | 1-30 |
| Microcrystalline Cellulose | Filler | 35-60 |
| Dibasic Calcium Phosphate Anhydrous | Filler | 10-35 |
| Sodium Starch Glycolate | Disintegrant | 2-5 |
| Magnesium Stearate | Lubricant | 0.5-1.5 |
| Total Tablet Weight | | 100.0 |

Immediate release (IR) tablets of the crystalline acetic acid solvate of (10R)-7-amino-12-fluoro-2,10,16-trimethyl-15-oxo-10,15,16,17-tetrahydro-2H-8,4-(metheno)pyrazolo [4,3-h][2,5,11]-benzoxadiazacyclotetradecine-3-carbonitrile (Form 3) were manufactured using a dry granulation process prior to compression. In this process the crystalline material was blended with some proportion of the excipients falling within the ranges outline above and the blend was dry granulated using a roller compactor. The granule was milled as part of this process. The granules were blended with remainder of any of the excipients (e.g., magnesium stearate) prior to compression.

Figure 13:
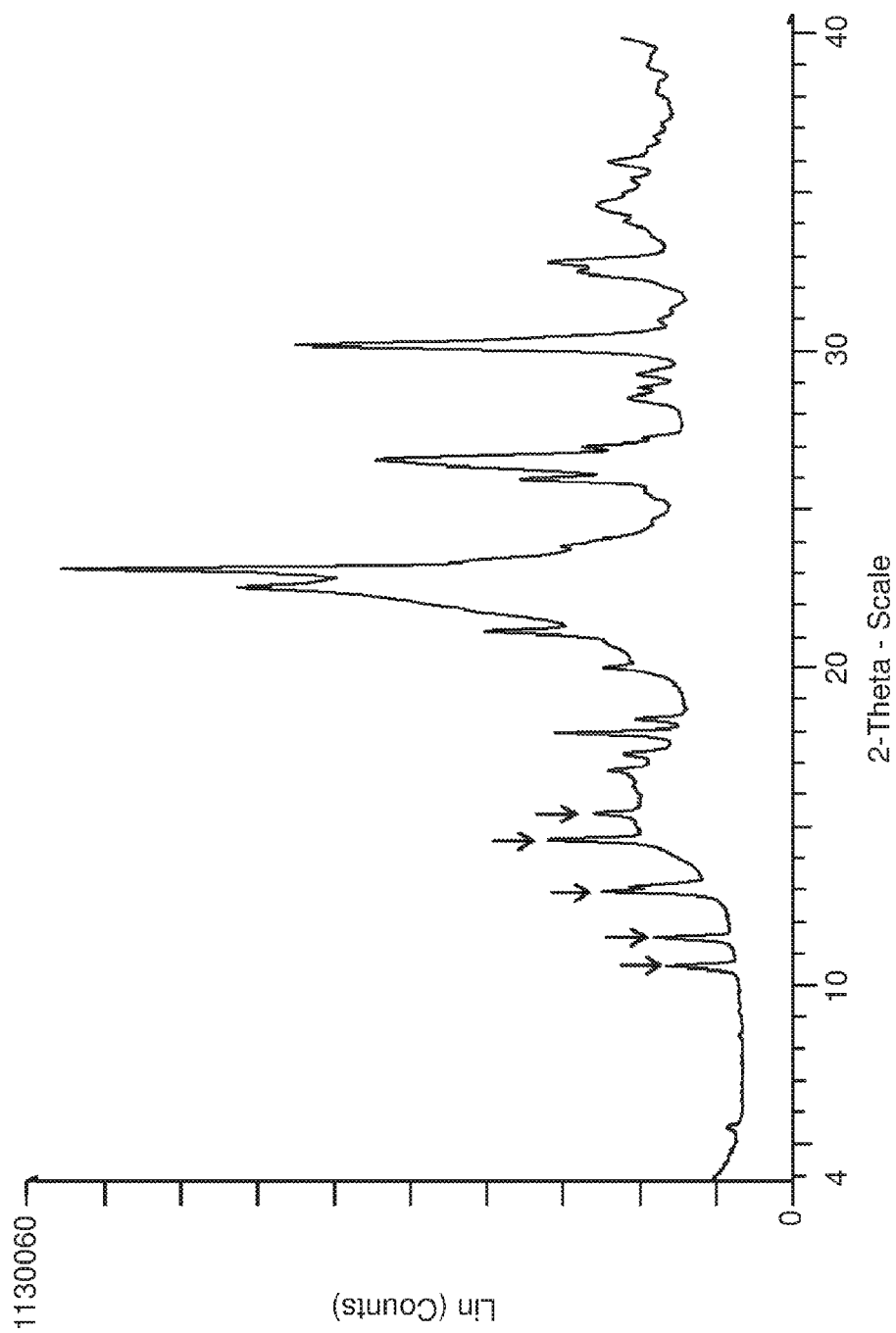
FIG. 13: PXRD pattern of a prototype drug product comprising crystalline acetic acid solvate of (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetradecine-3-carbonitrile (Form 3). Characteristic peaks are indicated with arrows.

FIG. 13 shows the PXRD pattern of a prototype drug product comprising the crystalline acetic acid solvate Form 3 of (10R)-7-amino-12-fluoro-2,10,16-trimethyl-15-oxo-10, 15,16,17-tetrahydro-2H-8,4-(metheno)pyrazolo[4,3-h][2,5, 11]-benzoxadiazacyclotetradecine-3-carbonitrile.

Figure 14:
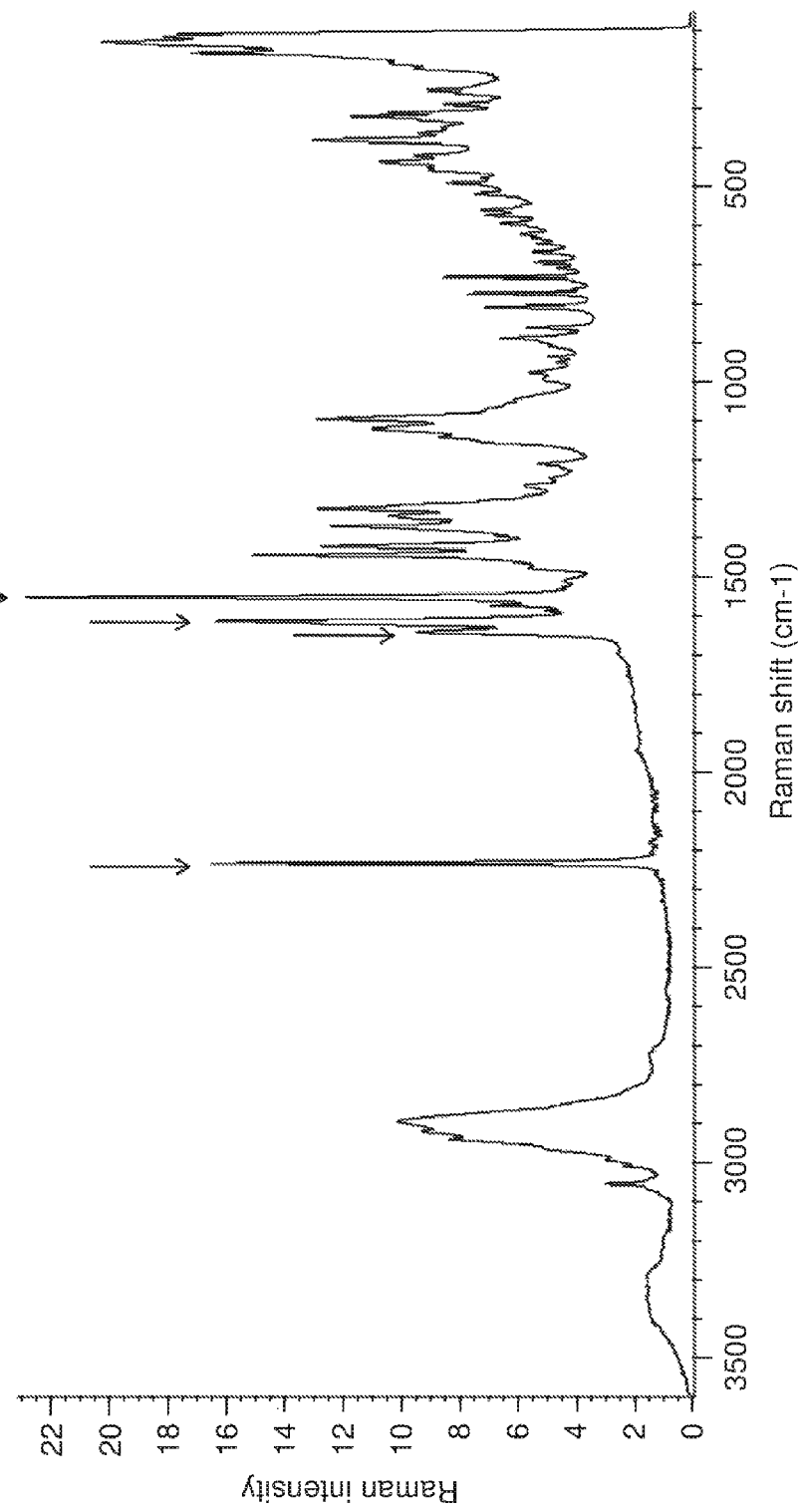
FIG. 14: FT-Raman pattern of a prototype drug product comprising crystalline acetic acid solvate of (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetradecine-3-carbonitrile (Form 3). Characteristic peaks are indicated with arrows.

FIG. 14 shows the FT-Raman pattern of a prototype drug product comprising the crystalline acetic acid solvate Form 3 of (10R)-7-amino-12-fluoro-2,10,16-trimethyl-15-oxo-10, 15,16,17-tetrahydro-2H-8,4-(metheno)pyrazolo[4,3-h][2,5, 11]benzoxadiazacyclotetradecine-3-carbonitrile.

Figure 15:
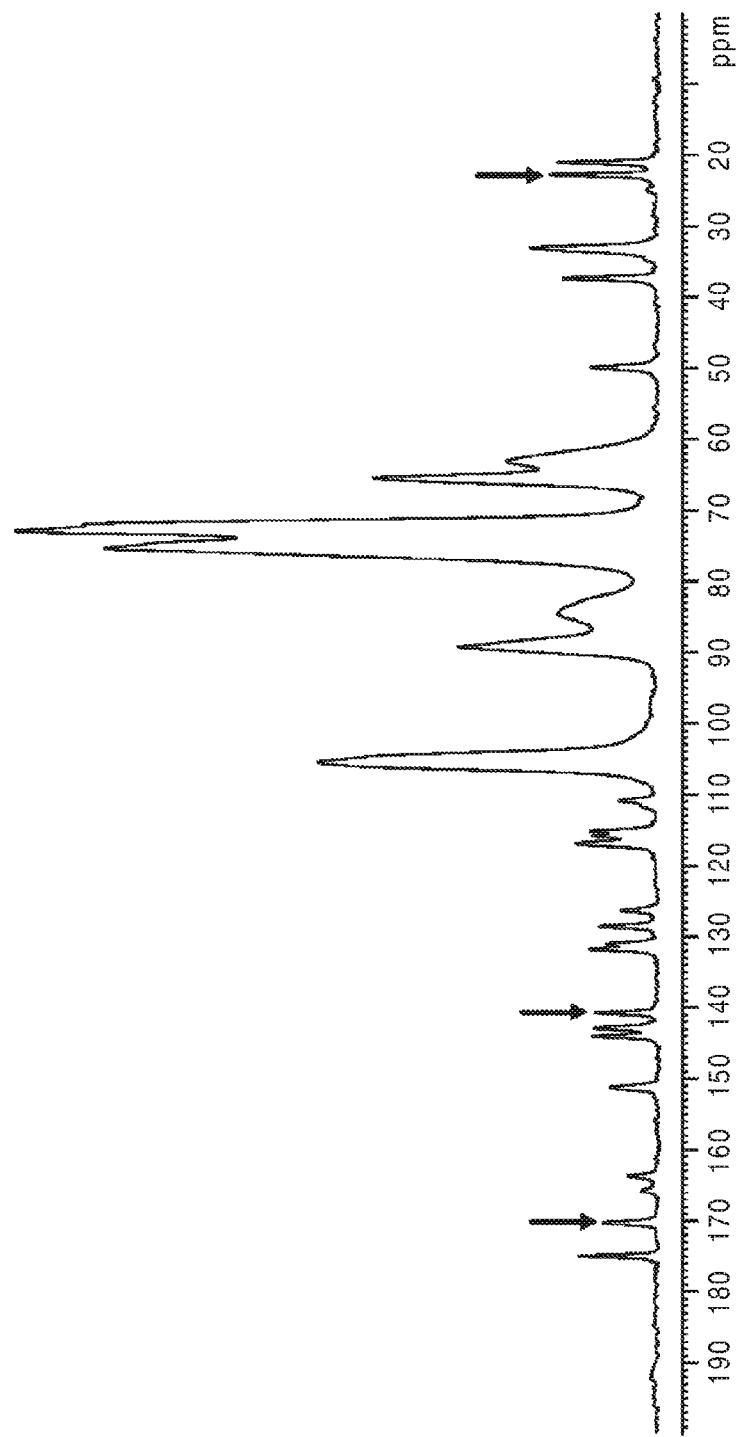
FIG. 15: Carbon CPMAS spectrum of a prototype drug product comprising crystalline acetic acid solvate of (10R)-7-amino-12-fluoro-2,10,16-trimethyl-15-oxo-10,15,16,17-tetrahydro-2H-8,4-(metheno)pyrazolo[-4,3-h][2,5,11]benzoxadiazacyclotetradecine-3-carbonitrile (Form 3). Characteristic peaks are indicated with arrows.

FIG. 15 shows the carbon CPMAS (ssNMR) spectrum of a prototype drug product comprising the crystalline acetic acid solvate Form 3 of (10R)-7-amino-12-fluoro-2,10,16-trimethyl-15-oxo-10,15,16,17-tetrahydro-2H-8,4-(metheno) pyrazolo[4,3-h][2,5,11]benzoxadiazacyclotetradecine-3-carbonitrile.

Figure 16:
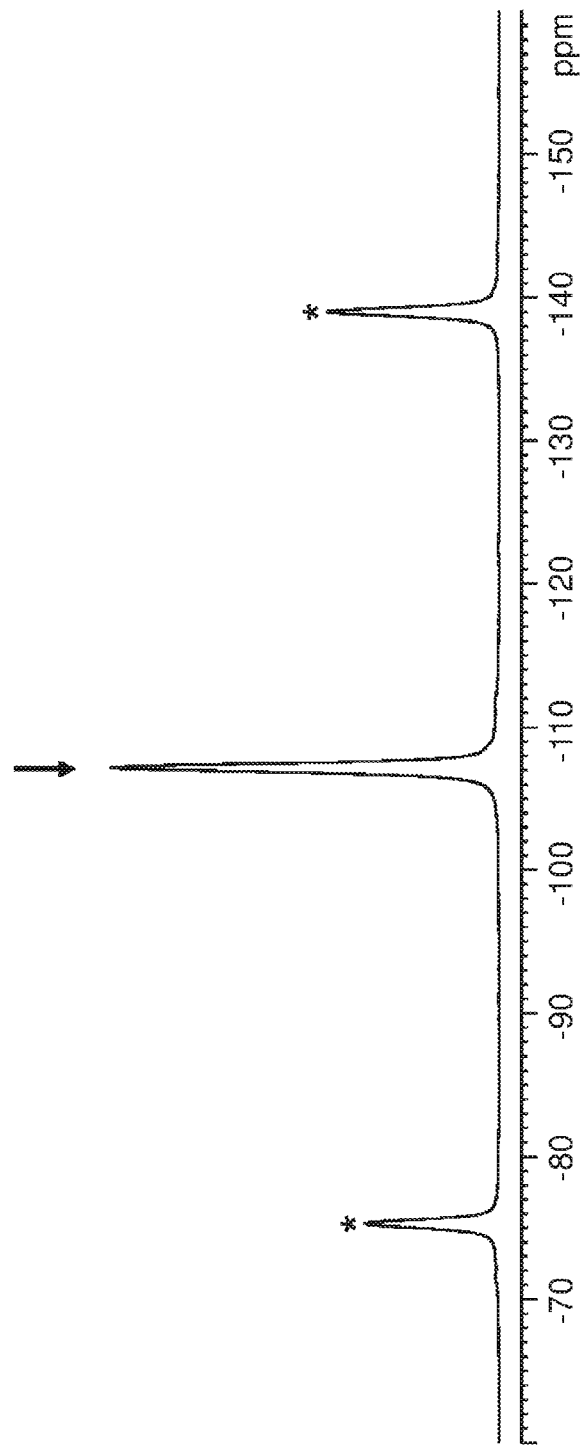
FIG. 16: Fluorine MAS spectrum of prototype drug product comprising crystalline acetic acid solvate of (10R)-7-amino-12-fluoro-2,10,16-trimethyl-15-oxo-10,15,16,17-tetrahydro-2H-8,4-(metheno)pyrazolo[4,3-h][2,5,11]benzoxadiazacyclotetradecine-3-carbonitrile (Form 3). Characteristic peaks are indicated with arrows. The peaks marked by asterisks are spinning sidebands.

FIG. 16 shows the fluorine MAS (ssNMR) spectrum of a prototype drug product comprising the crystalline acetic acid solvate Form 3 of (10R)-7-amino-12-fluoro-2,10,16-trimethyl-15-oxo-10,15,16,17-tetrahydro-2H-8,4-(metheno) pyrazolo[4,3-h][2,5,11]benzoxadiazacyclotetradecine-3-carbonitrile.

Characteristic PXRD (2θ±0.2°), FT-Raman (±2 cm$^{-1}$), and $^{13}$C and $^{19}$F ppm ssNMR (±0.2 ppm) peaks distinguishing crystalline Form 1 of (10R)-7-amino-12-fluoro-2,10,16-trimethyl-15-oxo-10,15,16,17-tetrahydro-2H-8,4-(metheno) pyrazolo[4,3-h][2,5,11]benzoxadiazacyclotetradecine-3-carbonitrile from standard formulation excipients when present in a representative drug product formulation are provided in Tables 2, 4, 6, and 8 herein.

Characteristic PXRD (2θ±0.2°), FT-Raman (±2 cm$^{-1}$), and $^{13}$C and $^{19}$F ppm ssNMR (±0.2 ppm) peaks distinguishing crystalline Form 2 of (10R)-7-amino-12-fluoro-2,10,16-trimethyl-15-oxo-10,15,16,17-tetrahydro-2H-8,4-(metheno) pyrazolo[4,3-h][2,5,11]benzoxadiazacyclotetradecine-3-carbonitrile from standard formulation excipients when present in a representative drug product formulation are provided in Tables 10, 12, 14 and 16 herein.

Characteristic PXRD (2θ±0.2°), FT-Raman (±2 cm$^{-1}$), and $^{13}$C and $^{19}$F ppm ssNMR (±0.2 ppm) peaks distinguishing crystalline Form 3 of (10R)-7-amino-12-fluoro-2,10,16-trimethyl-15-oxo-10,15,16,17-tetrahydro-2H-8,4-(metheno) pyrazolo[4,3-h][2,5,11]benzoxadiazacyclotetradecine-3-carbonitrile from standard formulation excipients when present in a representative drug product formulation are provided in Tables 18, 20, 21, 23 and 24 herein.

Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application, and yet these modifications and improvements are within the scope and spirit of the invention.

We claim:

1. A crystalline acetic acid solvate of (10R)-7-amino-12-fluoro-2,10,16-trimethyl-15-oxo-10,15,16,17-tetrahydro-2H-8,4-(metheno)pyrazolo[4,3-h][2,5,11]benzoxadiaza-cyclotetradecine-3-carbonitrile, having a powder X-ray diffraction pattern comprising a peak at a 2θ value of: 12.9° 2θ±0.2° 2θ.

2. The crystalline solvate of claim 1, having a powder X-ray diffraction pattern comprising peaks at 2θ values of: 12.9 and 14.5° 2θ±0.2° 2θ.

3. The crystalline solvate of claim 1, having a powder X-ray diffraction pattern comprising peaks at 2θ values of: 11.4, 12.9 and 14.5° 2θ±0.2° 2θ.

4. The crystalline solvate of claim 1, having a powder X-ray diffraction pattern comprising peaks at 2θ values of: 10.5, 11.4, 12.9 and 14.5° 2θ±0.2° 2θ.

5. The crystalline solvate of claim 1, having a powder X-ray diffraction pattern comprising peaks at 2θ values of: 10.5, 11.4, 12.9, 14.5 and 15.3° 2θ±0.2° 2θ.

6. The crystalline solvate of claim 1, having a Raman spectrum comprising wavenumber (cm$^{-1}$) values of: 2234 cm$^{-1}$+2 cm$^{-1}$.

7. The crystalline solvate of claim 1, having a Raman spectrum comprising wavenumber (cm$^{-1}$) values of: 809 and 2234 cm$^{-1}$±2 cm$^{-1}$.

8. The crystalline solvate of claim 1, having a Raman spectrum comprising wavenumber (cm$^{-1}$) values of: 809, 2234 and 3055 cm$^{-1}$+2 cm$^{-1}$.

9. The crystalline solvate of claim 1, having: (a) a $^{19}$F solid state NMR spectrum comprising the resonance (ppm) value of: −107.2 ppm±0.2 ppm; (b) a $^{13}$C solid state NMR spectrum comprising the resonance (ppm) value of: 140.7 ppm±0.2 ppm; or (c) both (a) and (b).

10. The crystalline solvate of claim 1, having a $^{13}$C solid state NMR spectrum comprising resonance (ppm) values of: 22.8, 140.7 and 170.3 ppm±0.2 ppm.

11. A pharmaceutical composition comprising a crystalline acetic acid solvate of claim 1, and a pharmaceutically acceptable excipient.

* * * * *

UNITED STATES PATENT AND TRADEMARK OFFICE
CERTIFICATE OF CORRECTION

PATENT NO. : 9,637,500 B2  
APPLICATION NO. : 14/898582  
DATED : May 2, 2017  
INVENTOR(S) : Andrew James Jensen, Suman Luthra and Paul Francis Richardson Page 1 of 1

It is certified that error appears in the above-identified patent and that said Letters Patent is hereby corrected as shown below:

Column 52, Line 27 in Claim 6 change "+ 2 $cm^{-1}$" to -- ± 2 $cm^{-1}$ --

Column 52, Line 33 in Claim 8 change "+ 2 $cm^{-1}$" to -- ± 2 $cm^{-1}$ --

Signed and Sealed this  
Eighth Day of August, 2017

Joseph Matal  
*Performing the Functions and Duties of the*  
*Under Secretary of Commerce for Intellectual Property and*  
*Director of the United States Patent and Trademark Office*